US011702654B2

United States Patent
Belton et al.

(10) Patent No.: US 11,702,654 B2
(45) Date of Patent: Jul. 18, 2023

(54) METHODS AND COMPOSITIONS FOR ADDRESSING INEFFICIENCIES IN AMPLIFICATION REACTIONS

(71) Applicant: ILLUMINA INC., San Diego, CA (US)

(72) Inventors: Jon-Matthew Belton, San Diego, CA (US); Johann Felix Schlesinger, San Diego, CA (US); Siarhei Manakou, San Diego, CA (US); Amanda Garfinkel Young, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 551 days.

(21) Appl. No.: 16/622,798

(22) PCT Filed: Jun. 13, 2018

(86) PCT No.: PCT/US2018/037203
§ 371 (c)(1),
(2) Date: Dec. 13, 2019

(87) PCT Pub. No.: WO2018/236631
PCT Pub. Date: Dec. 27, 2018

(65) Prior Publication Data
US 2020/0190510 A1 Jun. 18, 2020

Related U.S. Application Data

(60) Provisional application No. 62/522,543, filed on Jun. 20, 2017.

(51) Int. Cl.
*C12N 15/10* (2006.01)
*G16B 30/00* (2019.01)
*G16B 30/20* (2019.01)
*C40B 40/06* (2006.01)

(52) U.S. Cl.
CPC ......... *C12N 15/1093* (2013.01); *G16B 30/00* (2019.02); *G16B 30/20* (2019.02); *C40B 40/06* (2013.01)

(58) Field of Classification Search
None
See application file for complete search history.

(56) References Cited

U.S. PATENT DOCUMENTS

2009/0099040 A1   4/2009   Ward et al.
2016/0355879 A1   12/2016  Kamberov et al.

FOREIGN PATENT DOCUMENTS

| CN | 106282353 A | 1/2017 | |
|---|---|---|---|
| WO | 2014/028778 A1 | 2/2014 | |
| WO | 2015/126766 A1 | 8/2015 | |
| WO | WO-2015126766 A1 * | 8/2015 | ........... C12Q 1/6806 |
| WO | 2017/117541 A1 | 7/2017 | |
| WO | 2018/236631 A1 | 12/2018 | |

OTHER PUBLICATIONS

PCT/US2018/037203, "International Search Report", dated Aug. 2, 2018.
Yoon, H., et al., "PrimerDesign-M: a multiple-alignment based multiple-primer design tool for walking across variable genomes", Bioinformatics 31(9), Dec. 17, 2014, 1472-1474.

* cited by examiner

*Primary Examiner* — Kaijiang Zhang
(74) *Attorney, Agent, or Firm* — Fletcher Yoder P.C.

(57) ABSTRACT

Methods and systems for decreasing amplification bias and primer-dimer formation in amplification reactions and for amplifying a plurality of target polynucleotides from a sample in a single reaction and for sequencing the target polynucleotides where samples can include forensic samples and where target polynucleotides can include identity- or ancestry-informative markers, short tandem repeats (STRs) and single nucleotide polymorphisms (SNPs). Methods of determining a nucleotide spacer sequence for disrupting primer dimer formation can include: receiving a set of primer sequences; determining a plurality of candidate spacers between an adapter sequence and a gene-specific portion of the primer sequence, the determined plurality of candidate spacers comprises sequences that disrupt stable interactions between sequences of the set of primer sequences; ranking candidate spacers that meet a predetermined threshold value of stable interactions in the extension sequences; and outputting a set of the ranked spacers that meet the predetermined threshold.

23 Claims, 15 Drawing Sheets

Specification includes a Sequence Listing.

FIG. 3

A) Unmodified QCS Sequence

```
        adaptor sequence              QCS      gene-specific sequence
5'-TACACGACGCTCTTCCGATCTNNNNNGCARCTAGAATATAAGCAGGCAGGA    Forward primer
                       |||||||||||
   <<<<<<<<<<<<<<<<<AGACTCCCCGTGACTCTGGTATTTACCTTAAGAGCCCACGGTTC-5'
   Reverse primer      gene-specific sequence         adaptor sequence
```

B) Modification example #1: not so random QCS sequence (NSR-QCS)

```
        adaptor sequence         NSR-QCS   gene-specific sequence
5'-TACACGACGCTCTTCCGATCTHBHHHGCARCTAGAATATAAGCAGGCAGGA   Forward primer
                       |||xxxxx|||
        Reverse primer   AGACTCCCCGTGACTCTGGTATTTACCTTAAGAGCCCACGGTTC-5'
                          gene-specific sequence         adaptor sequence
```

C) Modification example #2: QCS plus spacer sequences

```
                                  aSpacer  gSpacer
        adaptor sequence             QCS            gene-specific sequence
5'-TACACGACGCTCTTCCGATCTACANNNNNAGCGGCARCTAGAATATAAGCAGGCAGGA   Forward primer
                       |||xxx||||xxxx
        Reverse primer   AGACTCCCCGTGACTCTGGTATTTACCTTAAGAGCCCACGGTTC-5'
                          gene-specific sequence         adaptor sequence
```

D) Combination example: not so random QCS sequence with spacers

```
                                   aSpacer gSpacer
        adaptor sequence             NSR-QCS      gene-specific sequence
5'-TACACGACGCTCTTCCGATCTACAHNNNBAGCGGCARCTAGAATATAAGCAGGCAGGA   Forward primer
                       |||xxxx|||xxxxx
        Reverse primer   AGACTCCCCGTGACTCTGGTATTTACCTTAAGAGCCCACGGTTC-5'
                          gene-specific sequence         adaptor sequence
```

FIG. 6

A) QCS Amelogenin-forward primer

```
                              QCS
5'-TACACGACGCTCTTCCGATCTNNNNNCCCTGGGCTCTGTAAAGAA
                       |||||||||||||
                  CACTGGGACCCGTCAAGGAATACCTTAAGAGCCCACGGTTC-5'
                                              rs1805009-reverse primer
```

B) QCS+ES Amelogenin-forward primer

```
                           aES  QCS  gES
5'-TACACGACGCTCTTCCGATCTACGBNNNDCGCTCCCTGGGCTCTGTAAAGAA
                       |||||x||xxxx
                        CACTGGGACCCGTCAAGGAATACCTTAAGAGCCCACGGTTC-5'
                                                rs1805009-reverse primer
```

FIG. 9
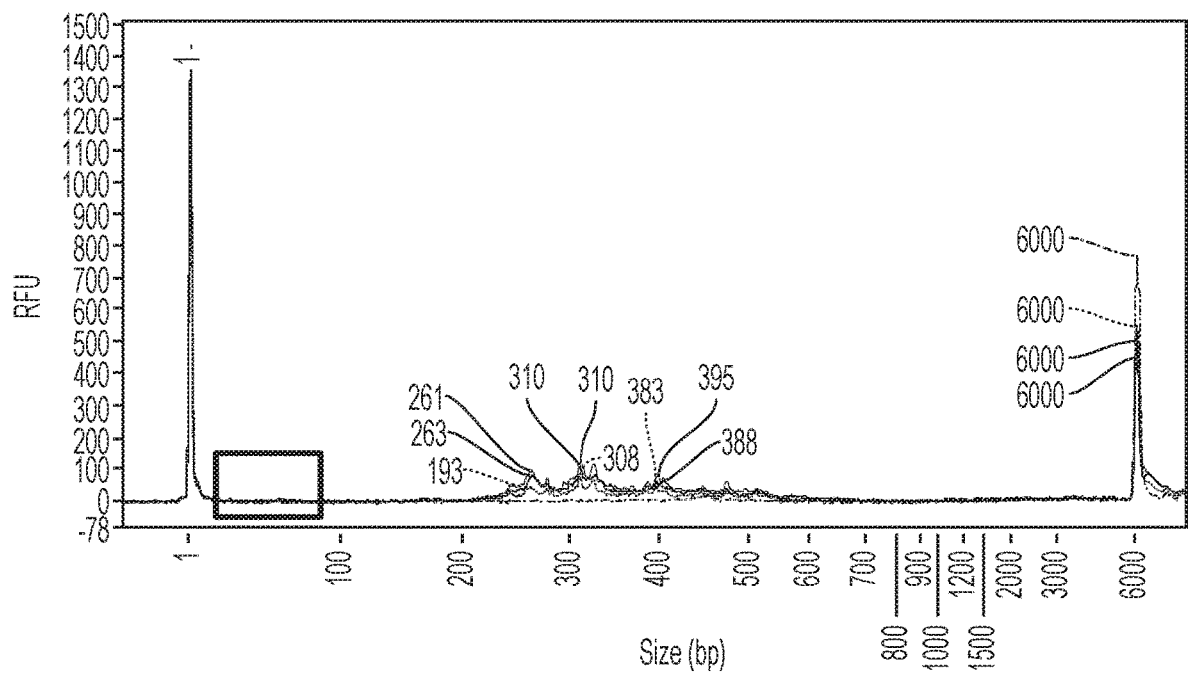
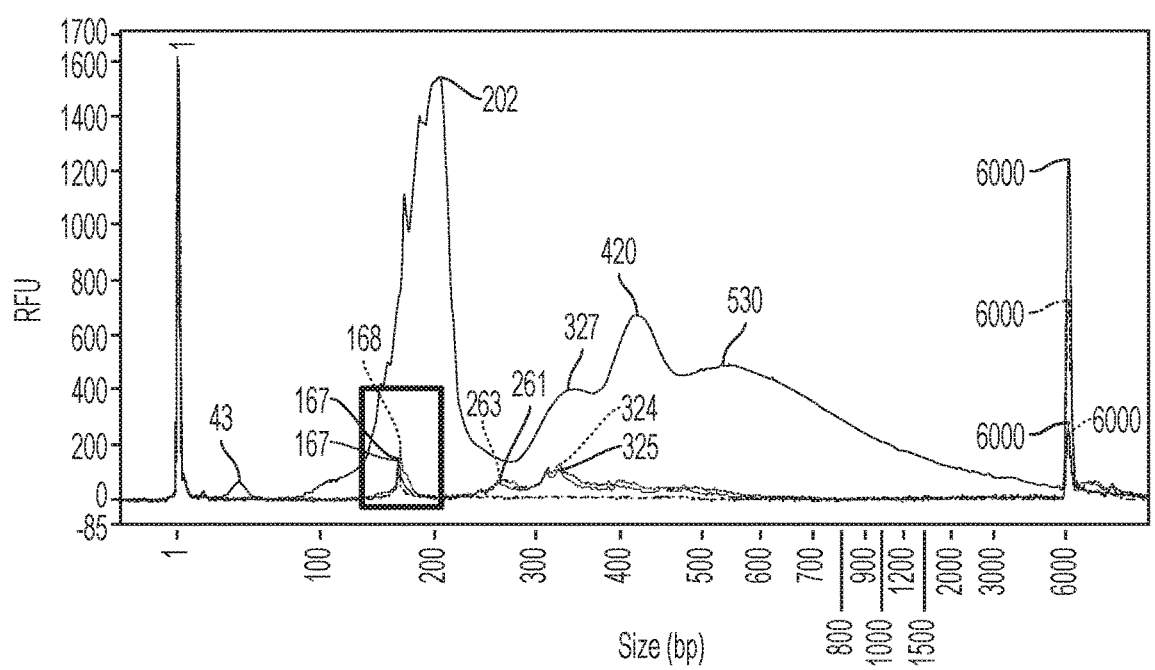

QCS with genomic side ES or gES

METHODS AND COMPOSITIONS FOR ADDRESSING INEFFICIENCIES IN AMPLIFICATION REACTIONS

CROSS-REFERENCE TO RELATED APPLICATIONS

This application is a National Stage Application claiming the priority of PCT Application No. PCT/US2018/037203, filed on Jun. 13, 2018, which claims priority to U.S. Provisional Patent Application No. 62/522,543, filed on Jun. 20, 2017, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jun. 7, 2018, is named IP-1448-PCT_SL.txt and is 121,820 bytes in size.

BACKGROUND

During amplification reactions, for example polymerase chain reaction or PCR reactions, bias can be introduced into the reactions. For example, some of the amplification primers may interact with each other causing primer-dimers to form. Primer-dimers form because of complementary bases shared by primers which hybridize to each other instead of their target sequence. Primer-dimers will also amplify during an amplification reaction thereby competing for amplification reagents and, in a worst-case scenario, inhibiting the target from being amplified. When primer-dimers form during a quantitative PCR, or qPCR, this will greatly affect the accuracy that is strived for when running theses types of amplification reactions.

Some of the primers may not be 100% homologous with the sequences they are targeting, for example there is one or more sequence mismatches between the primer and where it binds on the nucleic acid sequence. As amplification efficiency is sequence dependent, mismatches can cause bias amplification and lead to a shift in target amplification to the point of a target not even being detectably amplified. As such, amplification bias can greatly affect the accuracy of an amplification reaction.

DNA profiling is commonly performed in the analysis of samples collected at a crime scene or for determining the DNA profile of a population of individuals. Traditional DNA profiling methods involve size separation techniques, such as distinguishing and comparing genomic fragments containing STRs or ITRs on an electrophoresis system. More recently, DNA profiling methods have been introduced that involve PCR amplification of DNA from a sample followed by next-generation sequencing as found in PCT patent publication number WO2015/126766. Generating sequencable libraries can be very complex when dealing with a multitude of amplification products, each product representing one target. For example, if interrogation of 200 targets is desired then amplification of 200 targets takes place, each amplification requiring a set of primers so 400 different amplificiation primers together. Such a complex system could lead to adverse reactions that could decrease the efficiency of amplification reaction and therefore the resultant library for sequencing. Further, adverse reactions could result in desired targets being minimally or not amplified at all, therefore a target critical to interrogation could be lost or decreased to the point of non-confidence of results. One of the adverse reactions that could occur when large numbers of primers are present in an amplification reaction such as that described above for DNA profiling is the formation of primer-dimers.

The following disclosure describes methods and compositions to correct or minimize primer-dimer adverse reactions that could result in an amplification reaction, for example a complex multiplex amplification reaction. The result of correcting or minimizing the primer-dimers provides for a more efficient and robust target specific amplification system, for example for DNA forensics, fingerprinting needs, qPCR and other amplification reactions where a high degree of amplification accuracy is desired.

SUMMARY

The details of one or more embodiments are set forth in the accompanying drawings and the description below. Other features, objects, and advantages will be apparent from the description, drawings, and claims.

The present disclosure relates to methods, compositions, and kits for decreasing amplification bias and primer-dimer formation in amplification reactions. Methods for amplifying a plurality of target polynucleotides from a sample in a single reaction and for sequencing the target polynucleotides are also provided herein.

The disclosure provides for an oligonucleotide composition, comprising a plurality of primers, each primer comprising a target nucleic acid specific sequence (TS) and wherein the plurality of primers comprises two or more quality control sequence (QCS) selected from the group consisting of a first QCS (QCS1), wherein each nucleic acid position is fully randomized, a second QCS (QCS2), wherein one or more nucleic acid positions are partially randomized, a third QCS (QCS3), wherein one or more nucleic acid positions are fixed, a fourth QCS (QCS4), wherein all nucleic acid positions are fixed, a fifth QCS (QCS5), wherein one or more nucleic acid positions are fully randomized and one or more nucleic acid positions are partially randomized, a sixth QCS (QCS6), wherein one or more nucleic acid positions are fully randomized and one or more nucleic acid positions are fixed, a seventh QCS (QCS7), wherein one or more nucleic acid positions are partially randomized and one or more nucleic acid position are fixed, and an eighth QCS (QCS8), wherein one or more nucleic acid positions are fully randomized, one or more nucleic acid positions are partially randomized, and one or more nucleic acid positions are fixed.

The disclosure further provides an oligonucleotide composition, wherein the plurality of primers comprises 3, 4, 5, 6, 7, or 8 QCSs selected from the group consisting of QCS1, QCS2, QCS3, QCS4, QCS5, QCS6, QCS7, and QCS8, wherein the QCS of one or more primers is flanked by one or two extension sequences (ES).

In some embodiments, the compositions further comprise an adaptor sequence (AS) on the 5'-end of the QCS. The composition of the disclosure further comprises one or more primers with an extension sequence (ES) between the AS and QCS or between QCS and target sequence (TS).

The disclosure further provides an oligonucleotide composition wherein the ES is a fixed sequence comprising a sequence of between 1 and 10 bases. In a preferred embodiment the ES comprises a sequence of between 2 and 5 bases.

The disclosure further provides an oligonucleotide composition, wherein the plurality of primers comprises between about 4 primers and about 5000 primers. In a preferred embodiment the plurality of primers comprises between about 4 primers and about 550 primers.

The disclosure further provides an oligonucleotide composition, wherein at least one forward primer of the plurality of primer pairs comprises a QCS selected from the group consisting of QCS1, QCS2, QCS3, QCS4, QCS5, QCS6, QCS7, and QCS8, and wherein at least one reverse primer of the plurality of primer pairs comprises a QCS selected from the group consisting of QCS1, QCS2, QCS3, QCS4, QCS5, QCS6, QCS7, and QCS8.

The disclosure further provides a method of assembling an oligonucleotide composition comprising:
a) providing an initial primer pool including a plurality of primers wherein each primer includes a target sequence;
b) amplifying target polynucleotides from a sample using the initial primer pool;
c) identifying a subgroup of primers in the initial primer pool wherein the products of amplification result in an inaccurate allelic ratio or increased formation of primer dimers;
d) modifying one or more primers in the subgroup of primers, wherein modifying comprises modifying one or more primers to include a quality control sequence (QCS) and modifying one or more QCS to include one or more extension sequences (ES);
e) repeating steps b-d with modified primers until the products of amplification result in a accurate allelic ratio or decreased formation of primer dimers thereby producing an optimized primer pool.

The disclosure further provides a kit for analyzing a genomic DNA sample, comprising an optimized oligonucleotide primer pool. In a preferred embodiment, the DNA sample is a forensic sample.

A computer-implemented method of determining a nucleotide spacer sequence for disrupting primer dimer formation, can include: receiving a set of primer sequences; determining, using at least one microprocessor, a plurality of candidate spacers between an adapter sequence and a gene-specific portion of the primer sequence, the determined plurality of candidate spacers comprises sequences that disrupt stable interactions between sequences of the set of primer sequences; computing, using at least one microprocessor, a set of candidate spacers that meet a predetermined threshold value of stable interactions in the extension sequences; and outputting a set of the ranked spacers that meet the predetermined threshold.

BRIEF DESCRIPTION OF THE DRAWINGS

FIG. 2 discloses SEQ ID NOS 449-456, respectively, in order of appearance.

FIG. 3 illustrates exemplary modifications of QCS sequence incorporating primers to reduce QCS-mediated primer dimerization. A) non-modified primer dimer that results from incorporation of a random QCS sequence into an amplicon (SEQ ID NOS 457-458), B) example of one modification for reducing QCS mediated primer dimer formation (SEQ ID NOS 459-460), C) example of a second modification for reducing QCS mediated primer dimer formation (SEQ ID NOS 461-462), and D) example of combining the first and second modifications for reducing QCS based primer dimer formation (SEQ ID NOS 463-464). "N" can be any nucleotide base (e.g., A, C, T, G or U), "H" can be A, C or T, "B" can be C, T or G, "D" can be A, G or T.

FIG. 6 exemplifies interactions between primers A) when the forward amelogenin primer has a random QCS included and a primer dimer is formed with the rs1805009 reverse primer (SEQ ID NOS 465-466), and B) the disruption of the primer-dimer when a modified QCS and ES sequences are included in the amelogenin forward primer (SEQ ID NOS 467-468).

Figure 1:
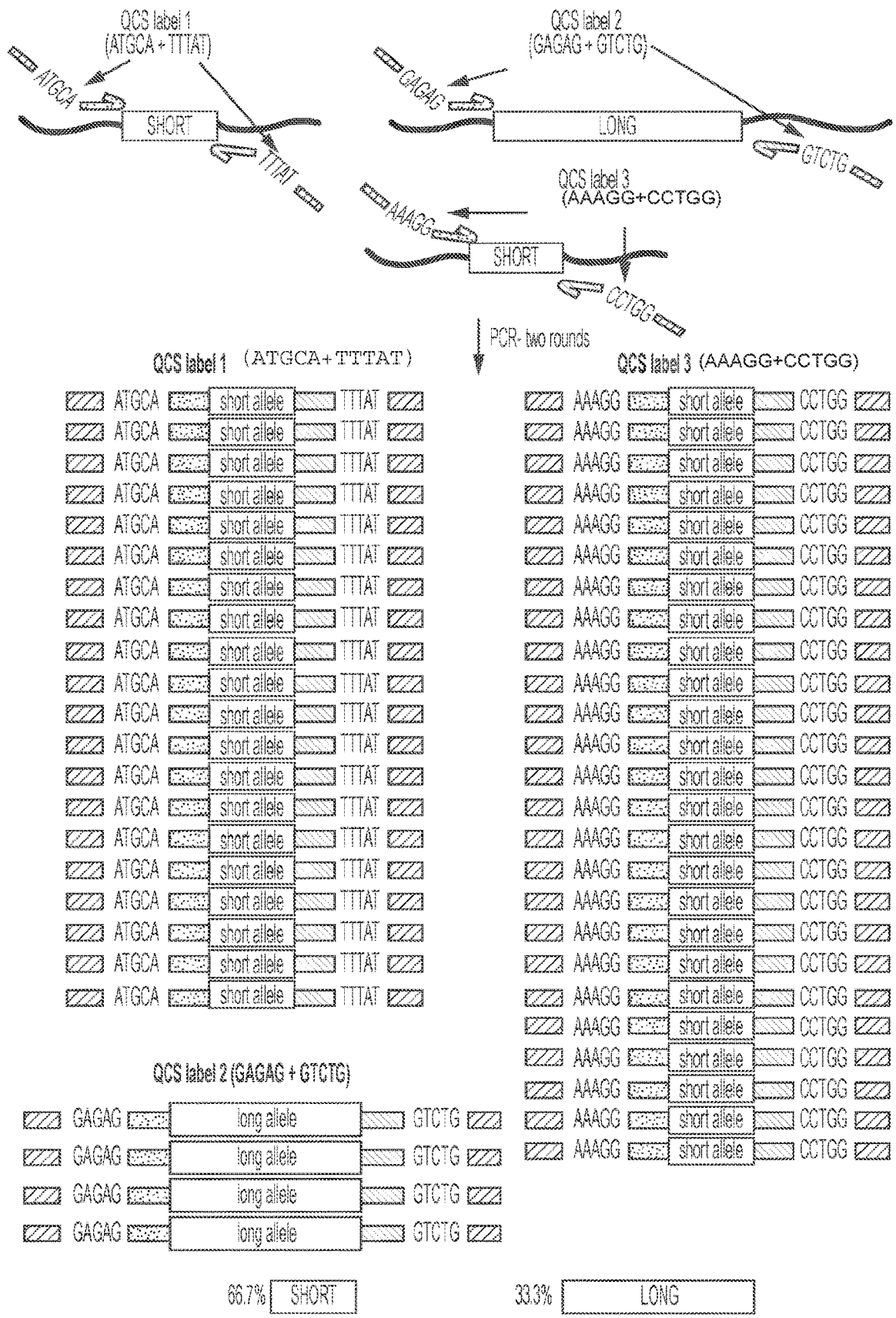
FIG. 1 illustrates the use of QCS-labeled primers in a multiplexed PCR reaction which results in amplicons more characteristic of a normal allele ratio despite PCR bias.

Additional features, advantages, and embodiments of the invention are set forth or apparent from consideration of the following detailed description, drawings and claims. Moreover, it is to be understood that both the foregoing summary of the invention and the following detailed description are examples and intended to provide further explanation without limiting the scope of the invention as claimed.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Several biological applications involve the amplification of nucleic acid molecules within a population. For such applications, it can be useful to increase the total number of targets that can be selectively amplified from a population within a single amplification reaction. Such amplification is typically achieved through the use of one or more primers that can hybridize to, or promote the amplification of, a particular target nucleic acid molecule. Such amplification can be complicated by the formation of amplification artifacts, such as primer-dimers and the like. The formation of such amplification artifacts (also referred to herein as non-specific amplification products) can consume critical amplification reagents, e.g., nucleotides, polymerase, primers, etc. Furthermore, such artifacts can frequently have shorter length relative to the intended product and can amplify more efficiently than the intended products and dominate the reaction output. The formation of such artifacts in amplification reactions, even when only a single pair of primers is employed, can complicate downstream applications such as qPCR, cloning, gene expression analysis and sample preparation for next-generation sequencing. In some downstream applications, including several next-generation sequencing methods, this problem can be compounded by the requirement to practice a secondary amplification step, since the artifacts can be further amplified during the secondary amplification.

Nucleic acid molecules amplified in a multiplex PCR reaction can be used in many downstream analysis or assays with, or without, further purification or manipulation. For example, the products of a multiplex PCR reaction (amplicons) when obtained in sufficient yield can be used for single nucleotide polymorphism (SNP) analysis, genotyping, copy number variation analysis, epigenetic analysis, gene expression analysis, hybridization arrays, analysis of gene mutations including but not limited to detection, prognosis and/or diagnosis of disease states, detection and analysis of rare or low frequency allele mutations, nucleic acid sequencing including but not limited to de novo sequencing or targeted resequencing, and the like. Multiplex target amplification is used in many molecular biology appllfications including, but not limited to detection of inherited diseases, congenital disorders, mutation detection associated with cancer, newborn disorders, pathogen identification, single cell genomics, forensic science and human identification.

One of the advantages and strengths of utilizing next generation sequencing (NGS) technology for DNA fingerprinting is that many targets can be interrogated simultaneously. The standard DNA fingerprinting gel electrophoretic system is limited in its ability to resolve multiple forensic DNA targets of different sizes using different fluorescent tags, further it is unable to differentiate single nucleotide changes. Next generation sequencing methods are not so limited and sequences can be obtained and targets identified regardless of the amplicon target size with no need for fluorescence tags, including single nucleotide changes. As such, NGS forensic DNA fingerprinting technologies can interrogate hundreds of targets simultaneously, quite the differentiator over the gel electrophoretic systems which currently can differentiate only a handful of targets, all of them either STR or ITR target. Next generation sequencing DNA forensic technologies can identify single nucleotide polymorphisms, or SNPs, which can be tied to ethnic, ancestry and phenotypic types of DNA fingerprints. For example, NGS DNA forensics methodologies can not only identify STRs and ITRs that differ from person to person, or animal to animal, but SNP identification can provide insight into a person's ancestral and ethnic heritage, their eye color, hair color, etc. This type of powerful resolution is not performed by the current gel electrophoresis systems.

However, great strides forward in technology are very rarely clean and tidy. For example, in order to sequence hundreds of DNA forensic targets oftentimes a DNA fragment library has to be created and it is the library of targets that is sequenced. One method of library preparation is to amplify targets, for example by polymerase chain reaction or PCR. Polymerase chain reaction creates exponential copies of the target being amplified thereby provided many copies for sequencing. Multiple sequences of a same region provides a robust, reproducible sequencing output that can be used with confidence in DNA databanking, criminal casework, etc.

PCR methodologies have their own challenges especially when there are potentially tens or hundreds of targets being amplified simultaneously. For example, for a multiplex amplification reaction resulting in differentially lengthed amplicons, amplification bias could occur wherein a normal ratio of long to short amplicons could be skewed such that either longer amplicons or shorter amplicons could be favored, thereby skewing an expected amplicon ratio. As such, bias can affect downstream sequencing as it would provide a skewed ratio of allelic target amplicons.

Another challenge is the interaction of primer to primer binding known as primer-dimerism that can occur even under normal amplification conditions, for example when only a set or a few sets of primers are present in one amplification reaction. Primer-dimers occur when the primers in a pair anneal to each other because of complementary sequences, or primers from different primer pairs anneal to each other, thereby taking them out of the amplification reaction altogether or they are extended and become unwanted templates themselves. These adverse primer-dimer reactions can have significant effects on the PCR reaction and resultant downstream library target pool that is used for sequencing. The unwanted primer-dimers could become unwanted templates, primer-dimers could result in desired targets being unamplified or minimally amplified, etc.

All of these unwanted events consume valuable reagent resources when they are used to sequence off target DNA fragments, consume valuable time and can lead to a low number of sequencing reads for a particular target or target sequence that is totally missing or dropped out.

Methods and compositions described in this disclosure are provided to minimize or eliminate primer-dimerism thereby increasing the efficiency and on read confidence of sequencing a sample as any off target sequencing reads waste reagents, time and more importantly might allow for a target not being sequenced deeply enough or not at all.

Provided herein are oligonucleotide compositions and methods for amplifying and sequencing a plurality of target polynucleotides from a sample. Also provided are methods for assembling the oligonucleotide compositions provided herein.

The compositions and methods provided herein are useful in many molecular biology appllfications including, but not limited to detection of inherited diseases, congenital disorders, mutation detection associated with cancer, newborn disorders, pathogen identification, single cell genomics, forensic science and human identification. In some embodiments, the compositions and methods provided herein are useful to perform DNA profiling analyses, e.g., for purposes of determining a person's identity or to determine familial relationships, e.g., in the context of paternity testing or ancestry related research. In some embodiments, the compositions and methods provided herein can be used, for example, as forensic methods to analyze a DNA sample from a crime scene. The compositions and methods are not limited to DNA profiling of humans, but could be equally applicable for identifying lineage and ancestry for non-human animals, for example equine, canine, bovine, porcine, feline and other animals where lineage and parentage determinations might be of use. Additionally, the compositions and methods could be equally applicable for identifying lineage, ancestry, etc. for crop or plant species. The compositions and methods herein could therefore be applicable to human, non-human animals, plants, etc. where lineage and ancestry determinations might be desired. Additionally, the compositions and methods described here can be used wherever primer-dimer reactions are problematic, such as in amplifying cancer or disease related targets, or amplification of targets of any kind.

Definitions

As used in this specification and the appended claims, the singular forms "a", "an" and "the" include plural referents unless the content clearly dictates otherwise. Thus, for example, reference to "a biomarker" includes a mixture of two or more biomarkers, and the like.

The term "about," particularly in reference to a given quantity, is meant to encompass deviations of plus or minus five percent.

As used herein, the terms "includes," "including," "includes," "including," "contains," "containing," and any variations thereof, are intended to cover a non-exclusive inclusion, such that a process, method, product-by-process, or composition of matter that includes or contains an element or list of elements does not include only those elements but can include other elements not expressly listed or inherent to such process, method, product-by-process, or composition of matter.

As used herein, "amplify", "amplifying" or "amplification reaction" and their derivatives, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art.

In some embodiments, the amplification reaction includes polymerase chain reaction (PCR). As used herein, the term "polymerase chain reaction" ("PCR") refers to the method described in U.S. Pat. Nos. 4,683,195 and 4,683,202, hereby incorporated by reference, which describe a method for increasing the concentration of a segment of a polynucleotide of interest in a mixture of genomic DNA without cloning or purification.

As used herein "multiplex PCR" or "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher.

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and themocycling conditions. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ and can also include various modifiers of ionic strength.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, and fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the polymerase can be optionally reactivated, for example through the use of heat, chemicals or re-addition of new amounts of polymerase into a reaction mixture. In some embodiments, the polymerase can include a hot-start polymerase or an aptamer based polymerase that optionally can be reactivated.

As used herein, the term "primer" and its derivatives refer generally to any polynucleotide that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may comprise ribonucleotides, deoxyribonucleotides, analogs thereof, or mixtures thereof.

As used herein, the term "Quality Control Sequence" or "QCS" refers to a nucleic acid sequence that is inserted in a primer and allows for an increase in the abundance of amplification products from (e.g., in a multiplexed PCR) a target polynucleotide of interest. Introduction of a QCS into one or more primers of a primer pool can be useful to determine accurate allele ratios for target polynucleotides in a sample, even in a case where an amplification reaction, e.g., a multiplexed PCR, is biased to overamplify a certain subset of alleles. Introduction of a QCS can also reduce or eliminate primer dimer formation, e.g., in a primer pool solution or in the course of a multiplexed PCR reaction. Additionally, a "Quality Control Sequence" refers to a nucleic acid sequence that is inserted into a primer, thereby incorporating the sequence into an amplification product, for purposes of improving the accuracy of quantifying the abundance of original template molecules from sequence PCR products.

As used herein, the term "QCS primer" refers to a primer including a QCS sequence. In some embodiments, a QCS primer is capable of amplifying a target polynucleotide of interest to detectable levels, whereas a primer that lacks the QCS but is otherwise essentially identical to the QCS primer is not capable of amplifying the target polynucleotide of interest to a detectable level, or is only capable of amplifying the target polynucleotide of interest to very low levels, e.g., to levels close to the detection limit of an assay analyzing the target polynucleotide (e.g., qPCR). A QCS incorporated into a primer can include, e.g., fully randomized, partially randomized, or fixed sequence, or the QCS can have a combination of fully randomized, partially randomized, or fixed nucleic acid positions in its sequence. In some embodiments, a QCS primer including one or more partially randomized or fixed positions in its sequence, or a combination thereof, is capable of amplifying a target polynucleotide of interest to detectable levels, whereas an otherwise essentially identical primer that includes a fully randomized QCS is not capable of amplifying the target polynucleotide of interest to a detectable level, or is only capable of amplifying the target polynucleotide of interest to very low levels, e.g., to levels close to the detection limit of an assay analyzing the target polynucleotide.

A QCS generally does not include a sequence that is a part of, or complementary to, an adapter sequence, a universal sequencing primer (e.g., Illumina®'s P5 or P7 primers), or a sequence of the primer's target polynucleotide. In some embodiments, the QCS of a QCS primer, or a combination of two QCSs in a primer pair, can include so many possible sequences that it is unlikely that different copies of the same target polynucleotide in a sample are labeled by the same QCS sequence, e.g., during amplification of the target polynucleotide using the QCS primers. For example, a sample can include about 100 copies of a genome or a target polynucleotide of interest and the QCS sequence of each primer in a QCS primer pair has five fully randomized positions and one fixed position. In this example, the QCS primer pair can include $45*2=1,048,575$ possible QCS sequences and the chance that any two of the 100 target polynucleotides of interest in the sample share the same QCS sequence, e.g., following 2 PCR cycles, is >1:10,000.

As used herein, the term "extension sequence" or "ES" refers to a sequence added to the QCS of a QCS primer to further improve the primer's ability to amplify (e.g., in a multiplexed PCR) a target polynucleotide of interest. For example, in some experimental results the QCS in a primer also contributed to primer-dimer formation. Addition of an ES to a QCS primer can, e.g., reduce a primer dimer formation, e.g., in a primer pool solution or in the course of a multiplexed PCR reaction. In some embodiments, a QCS-ES primer is capable of amplifying a target polynucleotide of interest to detectable levels, whereas a QCS primer that lacks the ES but is otherwise essentially identical to the QCS-ES primer is not capable of amplifying the target polynucleotide of interest to a detectable level, or is only capable of amplifying the target polynucleotide of interest to very low levels, e.g., to levels close to the detection limit of an assay analyzing the target polynucleotide (e.g., qPCR). An ES in a QCS-ES primer is generally a fixed sequence. In some embodiments, the ES is shorter than the QCS in the QCS-ES primer. An ES generally does not include a sequence that is a part of, or complementary to, an adapter sequence, a universal sequencing primer (e.g., Illumina®'s P5 or P7 primers), or a sequence of the primer's target polynucleotide.

As used herein, the term "plurality" refers to a population of two or more, such as two or more primers or other referenced molecules. In some embodiments, the two or more molecules of a plurality of molecules are the same molecules. For example, a plurality of primers can include two or more primers having the same nucleic acid sequence. In some embodiments, the two or more of a plurality of molecules are different molecules. For example, a plurality of primers can include two or more primers having different nucleic acid sequences. A plurality includes 2, 3, 4, 5, 6, 7, 8, 9, 10, 20, 30, 40, 50, 60, 70, 80, 90 or a 100 or more different members. A plurality can also include 200, 300, 400, 500, 1000, 5000, 10000, 50000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$ or $1\times10^7$ or more different molecules. A plurality includes all integer numbers in between the above exemplary plurality numbers.

As used herein, the term "target polynucleotide" is intended to mean a polynucleotide that is the object of an analysis or action. The analysis or action includes subjecting the polynucleotide to copying, amplification, sequencing and/or other procedure for nucleic acid interrogation.

As used herein, the term "target specific" or "target nucleic acid specific" or "TS" when used in reference to a primer or other oligonucleotide is intended to mean a primer or other oligonucleotide that includes a nucleotide sequence specific to a target polynucleotide sequence, namely a sequence of nucleotides capable of selectively annealing to an identifying region of a target polynucleotide.

As used herein, the term "adaptor" or "adaptor sequences" and its derivatives refers to nucleic acid sequences that are appended to another nucleic acid sequence. For example, in this disclosure forward and reverse primers are used in amplification of a target sequence. Those primers comprise target specific sequences (TS), optionally a quality control sequence (QCS) with or without one or more adjacent extension sequences (ES), and an adaptor sequence. Adaptor sequences are not required, but in the examples herein adaptor sequences are present. The adaptor is substantially non-complementaty to the 3' end or the 5' end of any target sequence present in a sample. Suitable lengths are in the range of about 10-100 nucleotides, preferably about 15-50 nucleotides. An adaptor can include any combination of nucleotides or nucleic acids. In some aspects, an adaptor can include one or more cleavage groups. An adaptor can include a sequence that is substantially identical, or substantially complementary, to at least a portion of a primer such as a universal primer for use in amplification of a nucleic acid. An adaptor can include one or more of a barcode or tag to assist with downstream capture, counting, error correction, sample identification, or sequences specific to a particular sequencing platform. One or more primers of the plurality of primers described herein include an adapter sequence (AS). In some embodiments, the AS is located on the 5'-end of a quality control sequence. Exemplary adaptor sequences can be found in the FORENSEQ DNA Signature Prep Reference guide from Illumina. The current disclosure is not limited to the types of adaptors that could be incorporated into an oligonucleotide.

As used herein, "quality control sequence 1" or "QCS1" refers to a nucleic acid sequence in which each nucleic acid position is fully randomized. A fully randomized nucleic acid position can, e.g., include any one of the four naturally occurring nucleobases adenine (A), guanine (G), cytosine (C), or thymine (T). A TS linked to a 5-mer QCS1 including A, G, C, and T can, for example, be linked to any one of $4^5=1,024$ possible QCS1 sequences. In some embodiments, a fully randomized nucleic acid position can include a nucleic acid including additional naturally occurring or synthetic nucleobases, such as idenosine, uracil, and the like. In some embodiments, different nucleic acids in a fully randomized nucleic acid position can be present in approximately equimolar ratios (e.g., 1:1:1:1 ratios for A, G, C and T). In some embodiments, the ratios of different nucleic acids in a fully randomized nucleic acid position can differ from equimolar ratios. For example, in some embodiments, one or more nucleic acids in a fully randomized nucleic acid position can be more abundant than one or more other nucleic acids in the fully randomized nucleic acid position (e.g., 2:1:1:1 ratios for A, G, C and T).

As used herein, "quality control sequence 2" or "QCS2" refers to a nucleic acid sequence in which one or more nucleic acid positions are partially randomized. A partially randomized nucleic acid position can include a subset of nucleic acids found in a fully randomized position, such as a fully randomized position in QCS1. In some embodiments, a partially randomized position includes nucleic acids including two or three of the nucleobases A, G, C, T. For example, a TS linked to a 5-mer QCS2 in which one position is partially randomized and includes for example A or G, and in which the remaining four positions are fully randomized to any one of $2*4^4=512$ possible QCS2 sequences. When one position is only partially random, where the partially random bases takes on one of two possibilities (instead of four): $2*4^4=2*4*4*4*4=512$.

In some embodiments, a partially randomized position can be A or G, A or C, A or T, G or C, G or T, or C or T. In some embodiments, a partially randomized position can be A, G, or C; A, G, or T; A, C or T; or G, C or T. In some embodiments, two or more (but not all) nucleic acid positions in QCS2 are partially randomized. The two or more partially randomized nucleic acid positions in QCS2 can include the same combinations of nucleic acids, or different combinations of nucleic acids. In some embodiments, different nucleic acids in a partially randomized nucleic acid position can be present in approximately equimolar ratios (e.g., 1:1:1 ratios for A, G, and C). In some embodiments, the ratios of different nucleic acids in a partially randomized nucleic acid position can differ from equimolar ratios. For example, in some embodiments, one or more nucleic acids in a partially randomized nucleic acid position can be more abundant than one or more other nucleic acids in the partially randomized nucleic acid position (e.g., 2:1:1 ratios for A, G, and C).

As used herein, "quality control sequence 3" or "QCS3" refers to a nucleic acid sequence in which one or more, but less than all, nucleic acid positions are fixed. A fixed nucleic acid position can include one of A, C, T and G. For example, a TS linked to a 5-mer QCS3, in which one position is fixed and in which the remaining four positions are fully randomized can be linked to any one of $1*4^4=256$ possible QCS3 sequences. That is, when one position is completely fixed, where the non-random base takes a single predefined possibility: $1*4^4=1*4*4*4*4=256$.

As used herein, "quality control sequence 4" or "QCS4" refers to a nucleic acid sequence in which all nucleic acid positions are fixed (e.g., as A, G, C, or T). For example, a TS linked to a QCS4 is linked to only one possible sequence.

As used herein, "quality control sequence 5" or "QCS5" refers to a nucleic acid sequence in which one or more nucleic acid positions are fully randomized and one or more nucleic acid positions are partially randomized. Different fully randomized positions in QCS5 can include the same sets of nucleic acids (e.g., all positions include A, G, C or T), or different sets of nucleic acids (e.g., one position includes A, G, C, or T and another position includes A, G, C, or U). Different partially randomized positions in QCS5 can include the same sets of nucleic acids (e.g., all positions include A, G, or C), or different sets of nucleic acids (e.g., one position includes A, G, and C and another position includes A, C, or T).

As used herein, "quality control sequence 6" or "QCS6" refers to a nucleic acid sequence in which one or more nucleic acid positions are fully randomized and one or more nucleic acid positions are fixed. Different fully randomized positions in QCS6 can include the same sets of nucleic acids (e.g., all positions include A, G, C or T), or different sets of nucleic acids (e.g., one position includes A, G, C, or T and another position includes A, G, C, or U). Different fixed nucleic acid positions in QCS6 can include the same nucleic acid (e.g., all positions are "A"), or different nucleic acids (e.g., one position is "A" and another position is "G").

As used herein, "quality control sequence 7" or "QCS7" refers to a nucleic acid sequence in which one or more nucleic acid positions are partially randomized and one or more nucleic acid position are fixed. Different partially randomized positions in QCS7 can include the same sets of nucleic acids (e.g., all positions include A, G, or C), or different sets of nucleic acids (e.g., one position includes A, G, or C and another position includes A, G, or T). Different fixed nucleic acid positions in QCS7 can include the same nucleic acid (e.g., all positions are "A"), or different nucleic acids (e.g., one position is "A" and another position is "G").

As used herein, "quality control sequence 8" or "QCS8" refers to a nucleic acid sequence in which one or more nucleic acid positions are fully randomized, one or more nucleic acid positions are partially randomized, and one or more nucleic acid positions are fixed. Different fully randomized positions in QCS8 can include the same sets of nucleic acids (e.g., all positions include A, G, C or T), or different sets of nucleic acids (e.g., one position includes A, G, C, or T and another position includes A, G, C, or U). Different partially randomized positions in QCS8 can include the same sets of nucleic acids (e.g., all positions include A, G, or C), or different sets of nucleic acids (e.g., one position includes A, G, or C and another position includes A, G, or T). Different fixed nucleic acid positions in QCS7 can include the same nucleic acid (e.g., all positions are "A"), or different nucleic acids (e.g., one position is "A" and another position is "G").

The following Table 1 compares the different potential sequences for a QCS.

TABLE 1

Quality Control Sequences

| Quality Control Sequence | Content |
| --- | --- |
| QCS1 | All nucleotides are fully randomized |
| QCS2 | One or more nucleotides are partially randomized |
| QCS3 | One or more, but less than all, nucleotides are fixed |
| QCS4 | All nucleotides are fixed |
| QCS5 | One or more nucleotides are fully randomized, one or more are partially randomized |
| QCS6 | One or more nucleotides are fully randomized, one or more are fixed |
| QCS7 | One or more nucleotides are partially randomized, one or more nucleotides are fixed |
| QCS8 | One or more nucleotides are fully randomized, one or more are partially randomized, and one or more are fixed |

As used herein, "detectable amplification," refers to a level of amplification of a target polynucleotide that is detectable by a method for nucleic acid detection known in the art, such as (quantitative) PCR, gel electrophoresis, LC-MS, HPLC, microarray, or the like. In some embodiments, detectable expression includes a level of expression resulting in an assay signal intensity (e.g., in a qPCR assay) that is at least two standard deviations (2□□or at least three standard deviations (3□□□above a background or negative control signal of the assay (e.g., an assay signal observed in the absence of a nucleic acid).

As used herein, "no detectable amplification" refers to a level of amplification of a target polynucleotide that is either not detectable by a method for nucleic acid detection known in the art, such as (quantitative) PCR, gel electrophoresis, LC-MS, HPLC, microarray, or the like. In some embodiments, "low-level amplification" refers to a level of expression resulting in an assay signal intensity (e.g., in a qPCR assay) that is within or close to the background noise of an assay, e.g., an assay signal intensity of less than two standard deviations (2□□from an average, median or mean background or negative control signal of the assay (e.g., an assay signal observed in the absence of a nucleic acid).

In some embodiments, the disclosure relates generally to human identification methods using one or more target specific primers disclosed herein or one or more target specific primers designed using the primer design criteria outlined herein. In one embodiment, a forensic or human identification sample containing at least one target sequence can be amplified using any one or more of the target-specific primers disclosed herein or using the primer criteria outlined herein.

Target Polynucleotides

In another aspect, provided herein are methods for amplifying or sequencing a plurality of target polynucleotides in a sample including using an oligonucleotide composition provided herein.

In some embodiments, the method includes providing a sample. As defined herein, "sample" and its derivatives, is used in its broadest sense and includes any specimen, culture and the like that is suspected of including a target nucleic acid. The sample can include any biological, clinical, surgical, agricultural, atmospheric or aquatic-based specimen containing one or more nucleic acids. The term also includes any isolated nucleic acid sample such as genomic DNA (gDNA), cell free DNA (cfDNA), circulating tumor DNA (ctDNA), complementary DNA (cDNA), mitochondrial DNA (mtDNA), or DNA from a single cell, formalin-fixed paraffin-embedded DNA (FFPE DNA), complementary DNA (cDNA), mitochondrial DNA (mtDNA) or DNA from a single cell. In some embodiments, the sample includes cell debris. In some embodiments, the sample includes a cell lysate.

In another embodiment, low molecular weight nucleic acid includes enzymatically or mechanically fragmented DNA. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample.

In some embodiments, the sample is a mammalian sample. In some embodiments, the sample is a human or ape (e.g., chimpanzee, gorilla, orangutan, gibbon, and the like) sample. In some embodiments, the sample is from a farm animal (e.g., pig, sheep, cow, horse, chicken, turkey, fish, and the like), pet (e.g., cat, dog, hamster, mouse, rat, and the like), or animal model (e.g., transgenic mouse or knock-out mouse). In another embodiment, the sample can include nucleic acid molecules obtained from a non-mammalian source such as a plant, bacteria, virus or fungus. In some embodiments, the source of the nucleic acid molecules may be an archived or extinct sample or species.

In some embodiments, the sample is a bodily fluid. In some embodiments, the bodily fluid includes, e.g., without limitation, amniotic fluid, aqueous humour and vitreous humour, bile, blood serum, breast milk, cerebrospinal fluid, cerumen (earwax), chyle, chime, endolymph and perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion and vomit.

In some embodiments, the sample is a forensic sample. In some embodiments, the forensic sample includes a hair, a fingernail, a scraping, a swab (e.g., friction swab, pillbox swab), a rope, dirt, a fabric or fiber, and the like. In some embodiments, the forensic sample was collected at a crime scene. In some embodiments, the forensic sample was collected from a witness, a victim, or a suspect. In one embodiment, forensic samples can include nucleic acids obtained from a laboratory associated with a forensic investigation or include forensic samples obtained by law enforcement agencies, one or more military services or any such personnel.

In some embodiments, the sample is a plant sample. In some embodiments, the plant sample is derived from a vegetable. In some embodiments, the plant sample is derived from a fruit.

In some embodiments, the method includes contacting the sample with an oligonucleotide composition provided herein.

In some embodiments, the method includes amplifying one or more target polynucleotides of interest from the sample, e.g., by PCR, using an oligonucleotide composition provided herein. In some embodiments, one or more of the target polynucleotides include an autosomal, Y- or X-chromosome STR. In some embodiments, one or more of the target polynucleotides include an identity-informative SNP. In some embodiments, one or more of the target polynucleotides include an ancestry-informative or a phenotype-informative SNP. In some embodiments, one or more of the target polynucleotides include an autosomal, Y- or X-chromosome STR, an identity-informative SNP, an ancestry-informative SNP or a phenotype-informative SNP.

Amplification Bias

Without wishing to be bound by theory, the present application is based, in part, on the observation that when performing multiplexed PCR to amplify a plurality of target polynucleotides of interest in a single reaction, e.g., from a genomic DNA sample, the amplification of at least some target polynucleotides can be biased such that target polynucleotide ratios are distorted in the PCR product relative to the ratios in the original sample. For example, it was observed that target polynucleotides containing certain STR alleles are frequently over-amplified in multiplexed PCR. Overamplification of some STR alleles in a sample can result in "inaccurate allele ratio" estimation. For example, an allele comprising a region containing a repeated sequence wherein that repeated sequence is repeated only a few times (a short STR) is amplified more during a multiplexed PCR than an allele comprising a a region containing a repeated sequence wherein that repeated sequence is repeated a large number of times (a long STR). Such biased PCR amplification results in inaccurate STR allelic ratios in the amplification product (e.g., 90% short STRs to 10% long STRs, as determined by counts of sequencing reads) relative to "accurate STR allelic ratios" present in a normal non-amplified genomic DNA sample (e.g., 66.7% short STR alleles to 33.3% long STR alleles).

The present application is further based, in part, on the observation that incorporation of random (not-predefined) nucleotide sequences into the primers of a multiplexed PCR reaction can enable correct allele ratio evaluation even in cases where the PCR reaction is biased. Such random nucleotide sequences incorporated into PCR primers provide one example of "quality control sequences" (QCSs) provided herein. FIG. 1 illustrates an example in which random 5-mer nucleotide sequences (QCS) are incorporated into each primer of a PCR primer pair. The QCS-labeled primers are incorporated into target nucleotide amplification products during the early cycles of a multiplexed PCR reaction, such that each target nucleotide in a sample can be identified by its specific QCS combination. An accurate STR allele ratio can be determined for target polynucleotides of interest in the original sample by counting QCS labels in the PCR product, rather than sequencing reads. An accurate STR allele ratio can be determined by counting QCS sequence instances, even though target polynucleotides with short STR sequences are overamplified in the PCR reaction.

If a QCS is sufficiently long it can uniquely label individual primer molecules. In practice a QCS can be designed to be of such a length that the probability of encountering two primer-molecules with the same QCS is small. In practice, DNA input for PCR frequently consists of only a few hundred copies of the genomic sample. Therefore, the probability of labeling copies of the same target polynucleotide with the same QCS is less than 1 in about 1,000. The number of QCS sequences, nQCS, per original target molecule depends on the experimental protocol, however generally if both the forward and reverse primers each comprise a 5nt random QCS then approximately 1,048,576 different possible QCS could be generated and the chance for any two random molecules having the same QCS is approximately 1/1,000,000. If we assume there are 300 target molecules then we might expect that (1−1/nQCSn−1)=99.97% of the targets molecules should have a unique QCS.

Primer-Dimer Events

Figure 2:
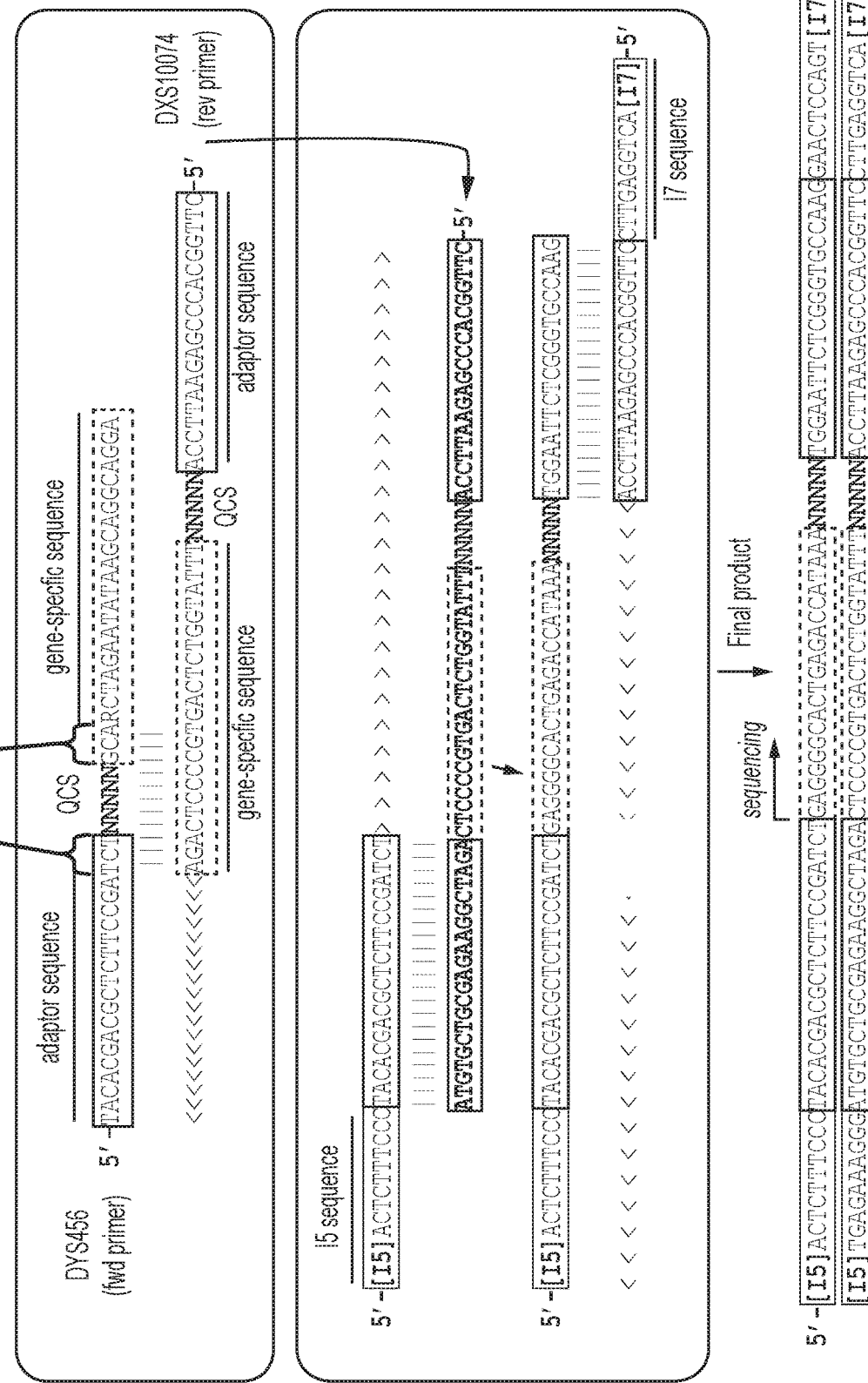
FIG. 2 illustrates an exemplary QCS-mediated example of primer dimerization for QCS containing primers.

The present application is further based, in part, on the observation that QCSs in PCR primers can promote primer dimerization. FIG. 2 illustrates examples for primer dimer formation in primers that do have a QCS. As known in the art, in the absence of a QCS in a PCR primer, primer-dimers can form, for example if a sequence of one primer and a sequence in another primer are partly complementary. In primers that include a QCS, the QCS itself can form part of a nucleotide sequence that is complementarity to a sequence in another primer ("complementary sequence stretch"), and thereby promote primer dimerization in a QCS-mediated fashion.

Primer dimers formed during a multiplex PCR can be extended to form sequenceable products. This can reduce the quality and quantity of sequencing data obtained from the PCR products of interest. For example, an abundance of sequenceable primer dimers can use up valuable surface area on the flowcell in a next-generation sequencing system and thereby reduce the capacity available to sequence target polynucleotides of interest in a sample. In addition, a flow cell surface that a large percentage of off target reads or reads of lower quality and quantity can lower the availability of pooling multiple samples in a sequencing reaction because a certain percentage of the sequencing data is expected to be of no interest, thereby increasing overall sequencing costs. Under certain PCR conditions primer dimers can become so abundant, or even dominant a PCR reaction especially in late PCR cycles, that the capacity of a DNA polymerase to amplify target polynucleotides of interest is negatively affected. Reduced efficiency of the PCR reaction can reduce the yield of correct on-target reads for target-polynucleotides.

The present application is further based on the observation that dimerization of PCR primers that include a randomized QCS can be reduced by introducing certain modifications in the QCS to disrupt complementarity stretches in primer dimers and prevent or reduce primer dimer formation. Shown in FIG. 3A is an example of a completely randomized, un-modified QCS sequence. To disrupt complementarity stretches in primer dimers, rather than incorporating a randomized QCS into a PCR primer as shown in FIG. 3A, the QCS sequence can be modified to be only partially randomized or to have defined nucleic acids in one or more positions in the sequence (FIG. 3B). A QCS can also be modified to add an extension sequence (ES), e.g., on the 5'-end (also called aSpacer on FIG. 3C), the 3'-end (also called gSpacer on FIG. 3C), or both ends of the QCS, and the extension sequence can disrupt complementarity stretches (FIG. 3C). In another embodiment, a QCS can be both modified to be only partially randomized or to have defined nucleic acids in one or more positions in its sequence and include an ES, e.g., on the 5'-end, the 3'-end, or both ends of the QCS to disrupt a complementarity stretch (FIG. 3D).

The present application is further based on the observation that primer pools including primers with or without a QCS, or including primers with different types of QCSs, such as a fully randomized QCS, a partially randomized QCS, a fully defined QCS, an extended QCS (QCS-ES), or combinations thereof can be used to amplify (e.g., in a multiplex PCR) and to sequence (e.g., by next-generation sequencing) target polynucleotides of interest from a sample. Target polynucleotide amplification and sequencing using the oligonucleotide compositions provided herein can yield improved sequencing data (e.g., in terms of % aligned reads) relative to data obtained, e.g., with primers that do not include a QCS or that only include one type of QCS (e.g., a fully randomized QCS).

Primer dimer formation in an oligonucleotide composition provided herein can be determined using any method known in the art, such as HPLC or LC-MS. In some embodiments, primer dimer yields are determined by size-exclusion chromatography, capillary electrophoresis, gel electrophoresis, bioanalyzer, HPLC, LC-MS or sequencing.

Quality Control Sequences

In one aspect, provided herein is an oligonucleotide composition, including a plurality of primers, each primer including a target nucleic acid specific sequence (TS) and a quality control sequence (QCS), wherein the plurality of primers includes two or more QCSs selected from the group consisting of a first QCS (QCS1), wherein each nucleic acid position is fully randomized, a second QCS (QCS2), wherein one or more nucleic acid positions are partially randomized, a third QCS (QCS3), wherein one or more nucleic acid positions are fixed, a fourth QCS (QCS4), wherein all nucleic acid positions are fixed, a fifth QCS (QCS5), wherein one or more nucleic acid positions are fully randomized and one or more nucleic acid positions are partially randomized, a sixth QCS (QCS6), wherein one or more nucleic acid positions are fully randomized and one or more nucleic acid positions are fixed, a seventh QCS (QCS7), wherein one or more nucleic acid positions are partially randomized and one or more nucleic acid position are fixed, and an eighth QCS (QCS8), wherein one or more nucleic acid positions are fully randomized, one or more nucleic acid positions are partially randomized, and one or more nucleic acid positions are fixed, wherein each of the two or more QCSs is located on a different primer of the plurality of primers.

In some embodiments, the oligonucleotide composition includes one or more primers including a TS and not including a QCS. In some embodiments, the plurality of primers include one or more primers including a TS and not including a QCS or an ES. The final determination of which primers are in need of a QCS and/or and ES sequence(s) is dependent on the degree of primer-dimer interations and which primers are engaging in primer-dimerization.

In some embodiments, the primers of a plurality of primers including the same TS also include the same QCS. For example, each primer in a plurality of primers including a first TS (TS1), can include the same QCS2 (QCS2(1)).

In some embodiments, primers of different pluralities of primers include different QCSs. In some embodiments, the different QCSs can be of different QCS categories (e.g., QCS1, QCS2, QCS3, QCS4, QCS5, QCS6, QCS7, or QCS8). For example, primers of a first plurality of primers can include a QCS2, and primers of a second plurality of primers can include a QSC3. In some embodiments, the different QCSs can be of the same QCS category. For example, primers of a first plurality of primers include a QCS2(1) in which one nucleic acid position is partially randomized and primers of a second plurality of primers include a QCS2(2) in which two nucleic acid positions are partially randomized.

In some embodiments, primers of different pluralities of primers include different TSs and the same QCS. For example, the primers of a first plurality of primers can include a TS1 and a QCS2(1), and the primers of a second plurality of primers can include a TS2 and the same QCS2 (1).

Extension Sequences

In some instances the inclusion of a QCS in a primer can lead to the QCS participating in primer-dimer formation. In this instance, the inclusion of extension sequences or ES can additionally be included in a primer to minimize or eliminate the created primer-dimer (FIG. 2). In some embodiments of the compositions provided herein, the QCS of one or more primers in the plurality of primers is further flanked by an extension sequence (ES), on one or both sides of the QCS. In some embodiments, the QCS flanked by an extension sequence is a QCS1, QCS2, QCS3, QCS4, QCS5, QCS6, QCS7, or QCS8. In some embodiments, the QCS is flanked by one ES. In some embodiments, the QCS is flanked by the ES on the 5'-end of the QCS, also called the "aSpacer". In some embodiments, the QCS is flanked by the ES on the 3'-end of the QCS, also called the "gSpacer". In some embodiments, the QCS is flanked by an ES at the 5'-end and at the 3'-end, thereby having the configuration of "aSpacer-QCS-gSpacer".

In some embodiments, the ES on the 5'-end of the QCS is the same as the ES on the 3'-end of the QCS. In some embodiments, the ES on the 5'-end of the QCS is different from the ES on the 3'-end of the QCS. In some embodiments, two or more ESs linked to different QCSs in a plurality of primers have different nucleic acid sequences. In some embodiments, two or more ESs linked to different QCSs in a plurality of primers have the same nucleic acid sequences.

In some embodiments, the QCS of one or more primers in the plurality of primers is not flanked by an ES and the QCS of one or more different primers is flanked by an ES. In some embodiments, the QCS is flanked by the ES on the 5'-end of the QCS. In some embodiments, the QCS is flanked by the ES on the 3'-end of the QCS. In some embodiments, the QCS is flanked by an ES on the 5'-end of the QCS and on the 3'-end of the QCS.

In some embodiments, the QCS of one or more primers in the plurality of primers is not flanked by an ES, the QCS of one or more primers is flanked by one ES (e.g., on the 5'-end or the 3'-end of the QCS), and the QCS of one or more primers is flanked by two ES (e.g., on the 5'-end and the 3'-end of the QCS).

In some embodiments, the QCS of one or more primers is flanked by one ES (e.g., on the 5'-end or the 3'-end of the QCS), and the QCS of one or more primers is flanked by two ES (e.g., on the 5'-end and the 3'-end of the QCS).

In some embodiments, one or more primers of the plurality of primers includes an ES that is located between the AS and the QCS (AES). In some embodiments, one or more primers of the plurality of primers includes an ES that is located between the QCS and the TS (TES). In some embodiments, one or more primers of the plurality of primers includes an AES and a TES. In some embodiments, one or more primers of the plurality of primers includes an AES or a TES, and one or more primers of the plurality of primers includes an AES and a TES.

In some embodiments, the ES is a fixed sequence. In some embodiments, the ES includes between 2 and 10 nucleotides. In a preferred embodiment, the ES sequence is 3 to 5 nucleotides long.

In some embodiments, the oligonucleotide compositions provided herein include only a decreased amount, if any, primer dimers, e.g., when the compositions are dissolved in an aqueous buffer (e.g., PCR reaction buffer). In some embodiments, an oligonucleotide composition including one or more QCS primers or one or more QCS-ES primers, in which the QCS or QCS-ES primers include two or more QCS of QCS1, QCS2, QCS3, QCS4, QCS5, QCS6, QCS7, or QCS8, include less than 50%, less than 40%, less than 30%, less than 20%, less than 10%, less than 5%, less than 3%, less than 1%, or less than 0.1% of primer dimers compared to an oligonucleotide composition including primers that lack the QCS or QCS-ES of the QCS primers or QCS-ES primers, and that otherwise have the same nucleotide sequences, (e.g., same ADs, same TSs).

In some embodiments, the oligonucleotide compositions provided herein include only a decreased amount, if any, primer dimers, e.g., when the compositions are dissolved in an aqueous buffer (e.g., PCR reaction buffer). In some embodiments, an oligonucleotide composition including one or more QCS primers or one or more QCS-ES primers, in which the QCS or QCS-ES primers include two or more QCS of QCS1, QCS2, QCS3, QCS4, QCS5, QCS6, QCS7, or QCS8, include less than 50%, less than 40%, less than 30%, less than 20%, less than 10%, less than 5%, less than 3%, less than 1%, or less than 0.1% of primer dimers compared to an oligonucleotide composition including QCS or QCS-ES primers including only one type of QCS (e.g., QCS1), and which otherwise have the same nucleotide sequences (e.g., same ADs, same TSs).

Target Sequences

The plurality of primers in the oligonucleotide compositions provided herein can include a plurality of different TSs. In some embodiments, the plurality of different TSs includes between about 20 and about 1000 TSs. In some embodiments, the plurality of different TSs includes between 100 and 400 TSs. In some embodiments, the plurality of different TSs includes between 200-300 TSs. In some embodiments, the different TSs are specific for different STRs in a genome. In some embodiments, the different TSs are specific for different single nucleotide polymorphisms (SNPs) in a genome. In some embodiments, the different TSs are specific for one or more STRs and one or more SNPs in a genome.

In some embodiments, the TSs of one or more primers are complementary to a region flanking a STR region. In some embodiments, the plurality of primers includes a primer including the nucleotide sequence of one or more primers, (FIG. 5) which includes primers for amplifying the STRs D16S359, D61043, DYS570, D19S433, PentaD, DYS576, AmelPP, DXS10135, D13S317, DYS389, D20S482, DXS10074 and SNPs rs1805009, rs10776839, rs2831700, rs1042602, and rs1058083. In some embodiments, the plurality of primers includes a primer including the nucleotide sequence of one or more primers, (FIG. 5) which includes primers for amplifying the STRs DYS392, D22S1045, DYS19, DYS456, DYS439, and DYS635.

In some embodiments, the plurality of primers includes a primer including the nucleotide sequence of one or more STR or ITR-targeted primers of WO 2015/126766, which is incorporated below.

TABLE 2

STR targeted primer sequences without tags and the corresponding amplicon sizes

| SEQ ID NO | STR LOCUS PRIMER | EXAMPLES OF STR PRIMERS WITHOUT TAGS | AMPLICON SIZE |
|---|---|---|---|
| 1 | Ame\|PP_F_T | CCCTGGGCTCTGTAAAGAA | 106, 112 |
| 2 | Ame\|PP_R_Sm | ATCAGAGCTTAAACTGGGAAGCTG | |
| 3 | CSF1PO_F1_T | ACAGTAACTGCCTTCATAGATAG | 117 |
| 4 | CSF1PO_R1_Sm | GTGTCAGACCCTGTTCTAAGTA | |
| 5 | D5S818_F2_T | TGATTTTCCTCTTTGGTATCCTTATGTAAT | 112 |
| 6 | D5S818_R2_Sm | ACAACATTTGTATCTTTATCTGTATCCT | |
| 7 | D8S1179_F1_T | TTTGTATTTCATGTGTACATTCGTATC | 110 |
| 8 | D8S1179_R1_Sm | ACCTATCCTGTAGATTATTTTCACTGTG | |
| 9 | D18S51_F1_T | CTCTGAGTGACAAATTGAGACCTT | 184 |
| 10 | D18S51_R1_T | TTAACTTCTCTGGTGTGTGGAGATG | |
| 11 | D19S433_F1_T | TTTGGTGCACCCATTACCCG | 188 |
| 12 | D19S433_R1_Sm | AGGAGGTTGAGGCTGCAAAA | |
| 13 | D7S820_F2_T | CACCAAATATTGGTAATTAAATGTTTACTATAGAC | 167 |
| 14 | D7S820_R2_Sm | TAAAGGGTATGATAGAACACTTGTC | |
| 15 | D16S539_F2_T | CAAAGGCAGATCCCAAGCTCT | 160 |

TABLE 2-continued

STR targeted primer sequences without tags and the corresponding amplicon sizes

| SEQ ID NO | STR LOCUS PRIMER | EXAMPLES OF STR PRIMERS WITHOUT TAGS | AMPLICON SIZE |
|---|---|---|---|
| 16 | D16S539_R2_Sm | TGTGTGTGCATCTGTAAGCAT | |
| 17 | D3S1358_F2_T | TGGTGTGTATTCCCTGTGCC | 170 |
| 18 | D3S1358_R2_Sm | GCAGTCCAATCTGGGTGACA | |
| 19 | D10S1248_F1_T | CCAATCTGGTCACAAACATATTAATGAA | 148 |
| 20 | D10S1248_R1_Sm | TTTCCCTTGTCTTGTTATTAAAGGAAC | |
| 21 | TH01_F1_T | TTCCCATTGGCCTGTTCCTC | 112 |
| 22 | TH01_R1_Sm | CTGTACACAGGGCTTCCGAG | |
| 23 | FGA_F2_T | GCTGAGTGATTTGTCTGTAATTG | 188 |
| 24 | FGA_R2_Sm | GAACTCACAGATTAAACTGTAACCAAAATAAAATTAG | |
| 25 | D6S1043_F1_T | CAATAGTGTGCAAGGATGGGTG | 175 |
| 26 | D6S1043_R1_Sm | TCTGTGGTTCTCCAGCTTAC | |
| 27 | TPOX_F1_T | CTTAGGGAACCCTCACTGAATG | 77 |
| 28 | TPOX_R1_Sm | GTCCTTGTCAGCGTTTATTTGC | |
| 29 | D13S317_F2_T | TTGGGTTGAGCCATAGGCAG | 162 |
| 30 | D13S317_R2_Sm | GCATCCGTGACTCTCTGGAC | |
| 31 | D21S11_F1_T | GTTATGGGACTTTTCTCAGTCTCCAT | 226 |
| 32 | D21S11_R3_Sm | GAGACTAATAGGAGGTAGATAGACTGG | |
| 33 | D12S391_F1_T | GAGACTGTATTAGTAAGGCTTCTC | 253 |
| 34 | D12S391_R2_Sm | CCTGGACTGAGCCATGCTCC | |
| 35 | D1S1656_F2_T | CAGTCCTGTGTTAGTCAGGATTC | 173 |
| 36 | D1S1656_R1_Sm | TCAAGGGTCAACTGTGTGATGT | |
| 37 | D9S1122_F3_T | CTTCTGAAAGCTTCTAGTTTACCT | 120 |
| 38 | D9S1122_R2_Sm | TTGCTTATTTGTGGGGGTATTTCA | |
| 39 | PentaE_F1_T | AAGAATTCTCTTATTTGGGTTATTAATTG | 362 |
| 40 | PentaE_R1_Sm | AAATTGTGGACAGGTGCGGT | |
| 41 | D17S1301_F2_T | CCATGTAAAAATACATGCATGTGTTTATTTATAC | 142 |
| 42 | D17S1301_R2_Sm | TGATTAAAAAGAATGAAGGTAAAAATGTGTATAAC | |
| 43 | D2S441_F2_T | CCAAATGTTTATGATTAATCTTTTAAATTGGAGC | 160 |
| 44 | D2S441_R3_Sm | GTAACAAGGGCTACAGGAATCATGAG | |
| 45 | D4S2408_F3_T | TCATCCACTGAAATGACTGAAAAATAG | 102 |
| 46 | D4S2408_R9_Sm | AGGTACATAACAGTTCAATAGAAAG | |
| 47 | D2S1338_F2_T | GAGTTATTCAGTAAGTTAAAGGATTGCAG | 162 |
| 48 | D2S1338_R2_Sm | GGGAGCCAGTGGATTTGGAAACAG | |
| 49 | PentaD_F3_T | GCATGGTGAGGCTGAAGTAG | 268 |
| 50 | PentaD_R1_Sm | CTAACCTATGGTCATAACGATTTTT | |
| 51 | vWA_F3_T | GATGATAAGAATAATCAGTATGTGACTTGG | 160 |
| 52 | vWA_R3_Sm | ATAGGTTAGATAGAGATAGGACAGATGATA | |
| 53 | SE33_F1_T | CCCTACCGCTATAGTAACTTGC | 380 |

TABLE 2-continued

STR targeted primer sequences without tags and the corresponding amplicon sizes

| SEQ ID NO | STR LOCUS PRIMER | EXAMPLES OF STR PRIMERS WITHOUT TAGS | AMPLICON SIZE |
|---|---|---|---|
| 54 | SE33_R2_Sm | CACGTCTGTAATTCCAGCTCCTA | |
| 55 | D20S482_F3_T | GGAAGCGTGTACTAGAGTTCTTCAG | 145 |
| 56 | D20S482_R2_Sm | GGACAGCCTCCATATCCACATG | |
| 57 | DXS10074_F1_T | TTCCTACTGCCCCACCTTTATTG | 212 |
| 58 | DXS10074_R1_sm | TTTATGGTCTCAGTGCCCCTCAGA | |
| 59 | DXS10103_F1_sm | TCATAATCACATATCACATGAGC | 177 |
| 60 | DXS10103_R1_T | AAACAGAACCAGGGGAATGAA | |
| 61 | DXS10135_F1_T | TGAAACTAAAGTCAAATGGGGCTAC | 268 |
| 62 | DXS10135_R1_sm | TAAGGGGTGACACCTCTCTGGATA | |
| 63 | DXS8377_F2_sm | CCCAGCCTACATCTACCACTTCATG | 276 |
| 64 | DXS8377_R2_T | CTAATGTTCGTATGGACCTTTGGAAAGC | |
| 65 | DXS7423_F1_sm | GTCTCCAGTACCCAGCTAGCTTAG | 191 |
| 66 | DXS7423_R1_T | TCTCCCAACCTGCCCTTTATCA | |
| 67 | DXS8378_F1_sm | TTTGGGCTGACACAGTGGCT | 442 |
| 68 | DXS8378_R1_T | TTGATCAACACAGGAGGTTTGACC | |
| 69 | HPRTB_F1_sm | TATACCACTTTGATGTTGACACTAGTTTAC | 213 |
| 70 | HPRTB_R1_T | CCTGTCTATGGTCTCGATTCAAT | |
| 71 | DXS10148_F3_sm | TGCATGACAGAGGGAGATTCT | 256 |
| 72 | DXS10148_R3_T | AGAGGGGAAATAGTAGAATGAGGATG | |
| 73 | DXS7132_F3_sm | GCCAAACTCTATTAGTCAACGTTC | 204 |
| 74 | DXS7132_R4_T | CTGGTTCTCTAGCTCACATACAGT | |
| 75 | DYF387S1ab_F2_T | TTTACCCCTAACAAGAAAAAAGAAGAA | 227, 231 |
| 76 | DYF387S1ab_R2_Sm | CAGTGTGAGAAGTGTGAGAAGTGC | |
| 77 | DYS385a_b_F1_T | GACACCATGCCAAACAACAAC | 260, 248 |
| 78 | DYS385a_b_R1_Sm | ATCTATCTATTCCAATTACATAGTCC | |
| 79 | DYS3891_II_F3_T | TCATTATACCTACTTCTGTATCCAACTCTC | 183, 303 |
| 80 | DYS3891_II_R3_Sm | GGAACACAATTATCCCTGAGTAGCAG | |
| 81 | DYS390_F2_T | GGTAGCATAATAGAAATTTTATGAGTGGG | 318 |
| 82 | DYS390_R2_Sm | GAAGACAGACTTCAATATCACAGAACATCG | |
| 83 | DYS391_F1_T | GTGTATCTATTCATTCAATCATACACCC | 143 |
| 84 | DYS391_R1_Sm | CTCCCTGGTTGCAAGCAATTGCC | |
| 85 | DYS438_F1_T | CCAAAATTAGTGGGGAATAGTTGAAC | 149 |
| 86 | DYS438_R2_Sm | GTCGAGATCACACCATTGCATTTC | |
| 87 | DYS439_F1_T | GCCTGGCTTGGAATTCTTTTACCC | 195 |
| 88 | DYS439_R1_Sm | TTTAAGTCTTTAATCTATCTTGAATTAATAGATTC | |
| 89 | DYS481_F1_T | CTTTAAGAGGAGTCTGCTAAAAGGAATG | 144 |
| 90 | DYS481_R3_Sm | TCACCAGAAGGTTGCAAGAC | |
| 91 | DYS505_F1_T | TCTGGCGAAGTAACCCAAAC | 174 |

TABLE 2-continued

STR targeted primer sequences without tags and the corresponding amplicon sizes

| SEQ ID NO | STR LOCUS PRIMER | EXAMPLES OF STR PRIMERS WITHOUT TAGS | AMPLICON SIZE |
|---|---|---|---|
| 92 | DYS505_R1_Sm | TCGAGTCAGTTCACCAGAAGG | |
| 93 | DYS522_F2_T | GGAACCAGTGAGAGCCG | 306 |
| 94 | DYS522_R2_Sm | CTCAGAGTGCTGAACCCAG | |
| 95 | DYS533_F2_T | GTATTTATTCATGATCAGTTCTTAACTCAACC | 206 |
| 96 | DYS533_R2_Sm | CTACCTAATATTTATCTATATCATTCTAATTATGTCTCTTC | |
| 97 | DYS549_F1_T | CTCTAAAGGTTTTTTTGGTGGCATAAG | 222 |
| 98 | DYS549_R1_Sm | GATTAATACAACAAAAATTTGGTAATCTGAAA | |
| 99 | DYS570_F1_T | CAACCTAAGCTGAAATGCAGATATTC | 170 |
| 100 | DYS570_R1_Sm | GTTATGAAACGTAAAATGAATGATGACTAG | |
| 101 | DYS576_F2_T | GCAGTCTCATTTCCTGGAGATGAAGG | 191 |
| 102 | DYS576_R1_Sm | CTTGGGCTGAGGAGTTCAATC | |
| 103 | DYS612_F2_T | GCCAGTAAGAATAAAATTACAGCATGAAG | 287 |
| 104 | DYS612_R2_Sm | GAATAATCTACCAGCAACAATGGCT | |
| 105 | DYS635_F4_T | TGCCCAATGGAATGCTCTCT | 274 |
| 106 | DYS635_R2_Sm | GCTCCATCTCAAACAACAAAAACACAAAAAATG | |
| 107 | DYS643_F2_T | GGGTCATTGAACCTCATGCTCTG | 170 |
| 108 | DYS643_R1_Sm | CCCCCCAAAATTCTACTGAAGTAAA | |
| 109 | Y_GATAH4_F2_T | TAACAGGATAAATCACCTATCTATGTAT | 175 |
| 110 | Y_GATAH4_R2_Sm | GCTGAGGAGAATTTCCAAATTTA | |

In some embodiments, the plurality of primers includes a primer including the nucleotide sequence of one or more SNP-targeted primers of of WO 2015/126766, incorporated below.

TABLE 3

SNP targeted primer sequences

| SEQ ID NO | SNP PRIMER | EXAMPLES OF SNP PRIMERS WITHOUT TAGS |
|---|---|---|
| 111 | rs10092491_iSNP\|_T_F2 | CCCGCAAACTAACTAGGATAAATCTCTA |
| 112 | rs1015250_iSNP\|_T_F | CGACATGGGAAATGTCAGATCATAAGAC |
| 113 | rs1024116_iSNP\|_T_F2 | CCAGGGAGTGAAAAATCCTTTTATCATC |
| 114 | rs1028528_iSNP\|_T_F2 | GAGGATGAAGGTTAGAGCCAGACCT |
| 115 | rs1029047_iSNP\|_T_F2 | TGTGGAATAAACTGAAGGCTAAAGAAAA |
| 116 | rs1031825_iSNP\|_T_F2 | CAAGCCCTATGCCAAGGATATAACAATG |
| 117 | rs10488710_iSNP\|_T_F | GAGGTTTTACTGTATTAGGAGTTCCCAC |
| 118 | rs10495407_iSNP\|_T_F | CAGATGTGAGATGATAATTTCGTTCTCC |
| 119 | rs1058083_iSNP\|_T_F | TTGTTCTTCTCCATCCCATTTCACCC |
| 120 | rs10773760_iSNP\|_T_F | CTTGTACATTCCCTTATCTGCTATGTGG |
| 121 | rs1294331_iSNP\|_T_F2 | CTCTCTTTGGAGTTTTATGTGTTGCTAC |
| 122 | rs12997453_iSNP\|_T_F | CTCTGATGATGTGCAAGAAAGGTAGGTA |

TABLE 3-continued

SNP targeted primer sequences

| SEQ ID NO | SNP PRIMER | EXAMPLES OF SNP PRIMERS WITHOUT TAGS |
|---|---|---|
| 123 | rs13182883_iSNP\|_T_F | TCAGACTATGTTTTAAGGAGACTATGAGG |
| 124 | rs13218440_iSNP\|_T_F | CTAAGTATCTACCAATGTGCTACGTACC |
| 125 | rs1335873_iSNP\|_T_F | CACGTGGATGATATGGTTTCTCAAGG |
| 126 | rs1336071_iSNP\|_T_F2 | AGCACCTATATATTATACCTGAAAGCAT |
| 127 | rs1355366_iSNP\|_T_F | CCCATGATTTTCTTGTGGTGAGAATTTC |
| 128 | rs1357617_iSNP\|_T_F | CACCCTCTGTACTTTAATTTGACTTCCC |
| 129 | rs1382387_iSNP\|_T_F | GTTTTTCTTCATTCCCATGTTGTGTAC |
| 130 | rs1413212_iSNP\|_T_F | CACTCTTCTGAATCCTGGTCAACAAC |
| 131 | rs1454361_iSNP\|_T_F | CAAGTTATATCATAGAGTCTACGACCCC |
| 132 | rs1463729_iSNP\|_T_F | CTGCAACTATCAGTCTCTGCCCTTATTC |
| 133 | rs1493232_iSNP\|_T_F | GATGTGTCTCAAACTGTTTATTGTGAGG |
| 134 | rs1498553_iSNP\|_T_F | GAACTCATTTATCCAGAGACCTGTTCTC |
| 135 | rs1523537_iSNP\|_T_F | CATAATACAACCTGTCTTTGGAGTTACT |
| 136 | rs1528460_iSNP\|_T_F | GTGACCAGTAGTTCTATGAGCAAGTATG |
| 137 | rs159606_iSNP\|_T_F | CCACATTGTATGGTTTTTAGGCACCATG |
| 138 | rs1736442_iSNP\|_T_F | CTAATAAGTGGGACAGTTAAGAGAAGGC |
| 139 | rs1821380_iSNP\|_T_F | CAAGACAAGCGATTGAAAGAAGTGGAT |
| 140 | rs1886510_iSNP\|_T_F | CCTTGTCAATCTTTCTACCAGAGGGTAA |
| 141 | rs1979255_iSNP\|_T_F | GAATCATAGCTTGTGTTGGTCAGGG |
| 142 | rs2016276_iSNP\|_T_F | GAATTACAAGTATTTGCATCCCAGCCT |
| 143 | rs2040411_iSNP\|_T_F | GACCAACTTGGCTTTAACAGATGCAAAT |
| 144 | rs2046361_iSNP\|_T_F2 | TCCTTACCTTTAAGACTTTTCCTATTTG |
| 145 | rs2056277_iSNP\|_T_F2 | CATTATCTCGTCATACTTCCCTGTCTTG |
| 146 | rs2076848_iSNP\|_T_F | GCATCAAATTCACCAGTGAAATTATTGA |
| 147 | rs2107612_iSNP\|_T_F | ATGAGTACATTATTCAACTGTTTTGGAG |
| 148 | rs2111980_iSNP\|_T_F | CAGCCATGTTGTAAACATTTTTACGGTC |
| 149 | rs214955_iSNP\|_T_F | GCACATTCTAAGAACTGGTGATTCTATC |
| 150 | rs221956_iSNP\|_T_F | GCTAGAAAAGCTGAGATAGCTGTGAAG |
| 151 | rs2342747_iSNP\|_T_F | CCTTGAAGCTCATTCTTTGTTGTCCC |
| 152 | rs2399332_iSNP\|_T_F | CTGGACACCAGACCAAAAACAAATAACC |
| 153 | rs251934_iSNP\|_T_F | GTAATTAGAGGGCAGTGAGGCTTTTAA |
| 154 | rs279844_iSNP\|_T_F | CTCCAGAAGCTACTGGGATATTAATTAG |
| 155 | rs2830795_iSNP\|_T_F | TGAGCCAAATCAGCAATATAATAGGACT |
| 156 | rs2831700_iSNP\|_T_F | CCTAGAACCACAATTATCTGTCTTTGGC |
| 157 | rs2920816_iSNP\|_T_F2 | CCATTGATTCTCTACAGTTCTGCAGGTA |
| 158 | rs321198_iSNP\|_T_F | CTCCACACTTTATACAGGTGAAATCTGA |
| 159 | rs338882_iSNP\|_T_F | CATTTTCTCTCCTTCTGTCTCACCTTC |
| 160 | rs354439_iSNP\|_T_F | GCTTCTCTTTCCCTTATGTATCTCTCTC |

TABLE 3-continued

SNP targeted primer sequences

| SEQ ID NO | SNP PRIMER | EXAMPLES OF SNP PRIMERS WITHOUT TAGS |
|---|---|---|
| 161 | rs3780962_iSNP\|_T_F | GGCTTTTGAAGAAAAACACTAACCTGTC |
| 162 | rs430046_iSNP\|_T_F | CACCTATGGGCTCTTCTTATTTCTCC |
| 163 | rs4364205_iSNP\|_T_F | CATTTGATAGCCATTTGGGTTGTTTCCA |
| 164 | rs445251_iSNP\|_T_F | CCATCACACTATCCTGACATGAACAAAT |
| 165 | rs4606077_iSNP\|_T_F | GAAGATTTGCATCCCAGTGAAAGCAC |
| 166 | rs560681_iSNP\|_T_F | GCACTTCATAAAGAATCAGTCAGGATGC |
| 167 | rs6444724_iSNP\|_T_F | GGAGAATCAGGAAATAGTCACTTCCTAC |
| 168 | rs6811238_iSNP\|_T_F | CATTTGACCTTCTAGCCAAATGAAGTAC |
| 169 | rs7041158_iSNP\|_T_F | GGAATTTCTGAGAATAACATTGCCTCTC |
| 170 | rs717302_iSNP\|_T_F | CATATGTTGGGGGAGCTAAACCTAATGA |
| 171 | rs719366_iSNP\|_T_F | CACTGTGACCACAGCATCTTTTAACTC |
| 172 | rs722098_iSNP\|_T_F2 | GGGTAAAGAAATATTCAGCACATCCAAA |
| 173 | rs722290_iSNP\|_T_F | GAGTATCCCTTATCTAAAATGCTGGTCC |
| 174 | rs727811_iSNP\|_T_F | CTTTTTCTCTTACCGGAACTTCAACGAC |
| 175 | rs729172_iSNP\|_T_F | CCTCATTAATATGACCAAGGCTCCTCTG |
| 176 | rs733164_iSNP\|_T_F | TGACTCTAATTGGGGATGTGGTAATTAG |
| 177 | rs735155_iSNP\|_T_F | GACCTAACCTGGAGAAAACCGGAGA |
| 178 | rs740598_iSNP\|_T_F | GTTTCTCTTCTCTGAACCTTTGTCTCAG |
| 179 | rs740910_iSNP\|_T_F | GCAAACACACAAAGATAGGTTCGAGTTT |
| 180 | rs763869_iSNP\|_T_F | CATATCAAGTGCTTTCTGTTGACATTTG |
| 181 | rs8037429_iSNP\|_T_F | CTGAAAAGTGCTACGTAAGAGGTCATTG |
| 182 | rs8078417_iSNP\|_T_F | CATCTGAGTGTGAGAAGAGCCTCAA |
| 183 | rs826472_iSNP\|_T_F2 | CCCAGCAAAAACTTCTTTTCTCCAGTAA |
| 184 | rs873196_iSNP\|_T_F | GCTAGGAAAGTTTTCTCTCTGGTTCACA |
| 185 | rs876724_iSNP\|_T_F | GAATATCTATGAGCAGGCAGTTAGCAG |
| 186 | rs891700_iSNP\|_T_F2 | CTAATCAGTGTCACTATGTGTGAGCTAT |
| 187 | rs901398_iSNP\|_T_F | CATCATACAGACTCAAGGAGCTTAGCTG |
| 188 | rs907100_iSNP\|_T_F | CTTTCCAAGCCTTGGAAAACACAGAAAA |
| 189 | rs914165_iSNP\|_T_F | GTACCTTATAAATCACGGAGTGCAGAC |
| 190 | rs917118_iSNP\|_T_F | CAAGTGGTAAGAGATGACTGAGGTCAA |
| 191 | rs938283_iSNP\|_T_F | CTTCTTCTCTTAGAAGGACACTGGTCAG |
| 192 | rs964681_iSNP\|_T_F | GTTATGGAGGATTGGTAAGAACCAGAG |
| 193 | rs987640_iSNP\|_T_F | GAGCTGTTTAAGGGTAAAGGGGTAGTTA |
| 194 | rs9905977_iSNP\|_T_F | GCAGACAAAACCATGACAATGATCTTAG |
| 195 | rs993934_iSNP\|_T_F | CCCATGATGAAACAGTTTGCACTAAATG |
| 196 | rs9951171_iSNP\|_T_F | CTCAATTTTCTTGTCCCTGCTTTCATG |
| 197 | rs10092491_iSNP\|_S_R2 | TTAGAAATTCCAGATAGAGCTAAAACTG |
| 198 | rs1015250_iSNP\|_S_R | GTTAGGAAAAGAACCCAGGTGTTTT |

TABLE 3-continued

SNP targeted primer sequences

| SEQ ID NO | SNP PRIMER | EXAMPLES OF SNP PRIMERS WITHOUT TAGS |
|---|---|---|
| 199 | rs1024116_iSNP\|_S_R2 | GCAAAAGTAAATACAAAGGCATACTTT |
| 200 | rs1028528_iSNP\|_S_R2 | CAATGCAAAAGAAAGGTCCTTACTCGAC |
| 201 | rs1029047_iSNP\|_S_R2 | CATTTCTAAACTCTAAAACAAACATTTG |
| 202 | rs1031825_iSNP\|_S_R2 | GGTCCTTAACCTATTAAATTTTAATGAG |
| 203 | rs10488710_iSNP\|_S_R | GACTTTCAATTTATGTCAGCATTTAAAA |
| 204 | rs10495407_iSNP\|_S_R | CCTCTTGGTTGCATTGGATTCTCATTG |
| 205 | rs1058083_iSNP\|_S_R | TCTCCATGAAACTTGGGTTAATTTTGC |
| 206 | rs10773760_iSNP\|_S_R | TGTCTGGAAGTTCGTCAAATTGCAG |
| 207 | rs1294331_iSNP\|_S_R2 | GTAGCATAAAACATTCCAAAAATTCAAT |
| 208 | rs12997453_iSNP\|_S_R | TGCTTTAAAGATACAGGTTATCTGTATTAC |
| 209 | rs13182883_iSNP\|_S_R | CTCTCCGTTACTTTCTTCCTGCCTTT |
| 210 | rs13218440_iSNP\|_S_R | GATCCTGAGATTCACCTCTAGTCCCT |
| 211 | rs1335873_iSNP\|_S_R | CCGTACCAGGTACCTAGCTATGTACT |
| 212 | rs1336071_iSNP\|_S_R2 | CTTTCTGTTTTGTCCATCTGAAATTCT |
| 213 | rs1355366_iSNP\|_S_R | CAAAGTTAAGTATCACCATCCAGCTGG |
| 214 | rs1357617_iSNP\|_S_R | ATAGGGATAGCTGATAAGAAACATGACC |
| 215 | rs1382387_iSNP\|_S_R | CTTAATAAGACGCTGCATCTGCCCA |
| 216 | rs1413212_iSNP\|_S_R | TCCAGGAGACATTTGTTCATATAAGTGA |
| 217 | rs1454361_iSNP\|_S_R | AGACACTTTTCAGTATCCATTTAGAAAC |
| 218 | rs1463729_iSNP\|_S_R | GTTTCACATGTGCATGCTTTTGGGT |
| 219 | rs1493232_iSNP\|_S_R | CCAAAGCTATTCTCTCTTTTGGGTGC |
| 220 | rs1498553_iSNP\|_S_R | GAAAGTTCACTTCAGATGTTCAAAGCC |
| 221 | rs1523537_iSNP\|_S_R | GGGTTTCAGTCTGCAACAAGATCTTG |
| 222 | rs1528460_iSNP\|_S_R | TGGAGATCAATATTTAGCCTTAACATAT |
| 223 | rs159606_iSNP\|_S_R | GACTGTTTCTCATCCTGTTATTATTTGT |
| 224 | rs1736442_iSNP\|_S_R | AACACACAGAAACATCAAGCTGAGC |
| 225 | rs1821380_iSNP\|_S_R | TTCCTGACATTCTCCTTCTTCTATCTG |
| 226 | rs1886510_iSNP\|_S_R | TATGACGCCTGGATTTTCACAACAAC |
| 227 | rs1979255_iSNP\|_S_R | CAGAGACTATGGATGGTATTTAGGTCAA |
| 228 | rs2016276_iSNP\|_S_R | ACTTTGTGTGGCTGAGAGAGAGAAA |
| 229 | rs2040411_iSNP\|_S_R | TGAGTGTTCTCTGTATTTTCTTACTCTAAG |
| 230 | rs2046361_iSNP\|_S_R2 | ATTTTTGGTCATTGTTGACACTTCACC |
| 231 | rs2056277_iSNP\|_S_R2 | GGTGTTAGGGAGACAGGCATGAATG |
| 232 | rs2076848_iSNP\|_S_R | TGAAACTTTTCAACTCTCCTACCGCC |
| 233 | rs2107612_iSNP\|_S_R | GTTAAAATTGCCACTAATTATGTGTTTT |
| 234 | rs2111980_iSNP\|_S_R | AACTGATCCTATGCAGCAAGATCTTTG |
| 235 | rs214955_iSNP\|_S_R | GATGCTTGCAAACAAAGACTGAAAAGG |
| 236 | rs221956_iSNP\|_S_R | GTCTGTGTGTCCTCTGAGATGATGAATG |

TABLE 3-continued

SNP targeted primer sequences

| SEQ ID NO | SNP PRIMER | EXAMPLES OF SNP PRIMERS WITHOUT TAGS |
|---|---|---|
| 237 | rs2342747_iSNP\|_S_R | GGGAGGAAGAAAACAGAGAGTCTTGA |
| 238 | rs2399332_iSNP\|_S_R | AGTTTGTTGGCTTCTTTTGAGAAGTATC |
| 239 | rs251934_iSNP\|_S_R | GGCAGATGAAGTAGTAGATATCTGGCTG |
| 240 | rs279844_iSNP\|_S_R | GTTCAGTGTCAATTTTGACCAGATATT |
| 241 | rs2830795_iSNP\|_S_R | AGACATAGGACACACCATTTTATTGTCT |
| 242 | rs2831700_iSNP\|_S_R | TCAAAATATTTGGCTAAACTATTGCCGG |
| 243 | rs2920816_iSNP\|_S_R2 | CTGGAGTTATTAATAAATTGGATTATATAGC |
| 244 | rs321198_iSNP\|_S_R | TTACCTGTTTTCCTTTTGTGATTCCAC |
| 245 | rs338882_iSNP\|_S_R | ACCAAGTCAAGAGCTCTGAGAGACAT |
| 246 | rs354439_iSNP\|_S_R | ACAGTGAATGATATTCAGAATATTGTGC |
| 247 | rs3780962_iSNP\|_S_R | GAACAAGGTCAAGATATCAGCTTTCACC |
| 248 | rs430046_iSNP\|_S_R | AGGTCATACAATGAATGGTGTGATGT |
| 249 | rs4364205_iSNP\|_S_R | ATCCACCCATGAGAAATATATCCACAA |
| 250 | rs44525_iSNP\|_S_R | ACAATTCAAATTAATGTAAAAACTGCAAGTG |
| 251 | rs4606077_iSNP\|_S_R | TAGTTCTAGTGTGGGATCTGACTCC |
| 252 | rs560681_iSNP\|_S_R | GAACATCTGTTCAGGTTTCTCTCCATC |
| 253 | rs6444724_iSNP\|_S_R | GAAAGGACTAAATTGTTGAACACTGGT |
| 254 | rs6811238_iSNP\|_S_R | TGTGTGTTTTAAAGCCAGGTTTGTT |
| 255 | rs7041158_iSNP\|_S_R | GATGGACTGGAACTGAGGATTTTCA |
| 256 | rs717302_iSNP\|_S_R | AGCTTTAGAAAGGCATATCGTATTAACTG |
| 257 | rs719366_iSNP\|_S_R | TTATAGTGAGTAAAGGACAGGCCCC |
| 258 | rs722098_iSNP\|_S_R2 | ACACATCTGTTGACAGTAATGAAATATCC |
| 259 | rs722290_iSNP\|_S_R | GTTTAAACTTGGATACCATCCCCAAGAC |
| 260 | rs727811_iSNP\|_S_R | ATGAGATTGCTGGGAGATGCAGATG |
| 261 | rs729172_iSNP\|_S_R | CACATTTCCCTCTTGCGGTTACATAC |
| 262 | rs733164_iSNP\|_S_R | GACAAGCCTCGCTTGAGTTTTCTTT |
| 263 | rs735155_iSNP\|_S_R | TGTGAGAGTGTCACCGAATTCAACG |
| 264 | rs740598_iSNP\|_S_R | AAATAGCAATGGCTCGTCTATGGTTAG |
| 265 | rs740910_iSNP\|_S_R | TGCTAAGTAAGGTGAGTGGTATAATCA |
| 266 | rs763869_iSNP\|_S_R | ATAAATATGATGTGGCTACTCCCTCAT |
| 267 | rs8037429_iSNP\|_S_R | GCTACACCTCCATAGTAATAATGTAAGAG |
| 268 | rs8078417_iSNP\|_S_R | TGAAGCAGCTAGAGAACTCTGTACGT |
| 269 | rs826472_iSNP\|_S_R2 | TTTTGTCTCTGTTATATTAGTCACCTATCTC |
| 270 | rs873196_iSNP\|_S_R | ATAGCCCTGCATTCAAATCCCAAGTG |
| 271 | rs876724_iSNP\|_S_R | TCCATTTTTATACCACTGCACTGAAG |
| 272 | rs891700_iSNP\|_S_R2 | GCAGTAAAACATTTTCATCAAATTTCCA |
| 273 | rs901398_iSNP\|_S_R | TCTGGGTGCAAACTAGCTGAATATCAG |
| 274 | rs907100_iSNP\|_S_R | GAAAATCTGGAGGCAATTCATGATGCC |

TABLE 3-continued

SNP targeted primer sequences

| SEQ ID NO | SNP PRIMER | EXAMPLES OF SNP PRIMERS WITHOUT TAGS |
|---|---|---|
| 275 | rs914165_iSNP\|_S_R | ATACAATGATGATCACACGGGACCCT |
| 276 | rs917118_iSNP\|_S_R | CCATGAAGATGGAGTCAACATTTTACA |
| 277 | rs938283_iSNP\|_S_R | TCCTAACCCCTAGTACGTTAGATGTG |
| 278 | rs964681_iSNP\|_S_R | GAGGTGATTTCTGTGAGGAACGTCG |
| 279 | rs987640_iSNP\|_S_R | GTACATTCACTTAACAGGCTCTCTTTCC |
| 280 | rs9905977_iSNP\|_S_R | AATTCATGAGCTGGTGTCCAAGGAG |
| 281 | rs993934_iSNP\|_S_R | ATAACAGTCTCCAGAGTATATTAGCTTAG |
| 282 | rs9951171_iSNP\|_S_R | GTTCCTCTGGGATGCAACATGAGAG |
| 283 | rs10497191_aSNP\|_T_F | GAAAGGATGAAGAGGGTGGATATTGGAG |
| 284 | rs1079597_aSNP\|_T_F | CCAAACCTCATCATCTCTTACCTGGATT |
| 285 | rs11652805_aSNP\|_T_F | GTCCAAAGTCAAGTGCAAGTATAGTTGG |
| 286 | rs1229984_aSNP\|_T_F | ACAATCTTTTCTGAATCTGAACAGCTTC |
| 287 | rs12439433_aSNP\|_T_F | CAAAGGAAGGCATTTCCTAATGATCTTC |
| 288 | rs12498138_aSNP\|_T_F | CTTTGCTTTGCTTTTCTTCTTCAGGGAA |
| 289 | rs12913832_aSNP\|_NU_T_F | CTGCTTCAAGTGTATATAAACTCACAGT |
| 290 | rs1426654_aSNP\|_T_F | CCTAGGAAAGCAGTAACTAATTCAGGAG |
| 291 | rs1462906_aSNP\|_T_F | GCAATTTGTTCACTTTTAGTTTCGTAGC |
| 292 | rs1572018_aSNP\|_T_F | GGCCTAATATGCATGTGTTCATGTCTCT |
| 293 | rs16891982_aSNP\|_T_F | CAGAGTTTCTCATCTACGAAAGAGGAGT |
| 294 | rs174570_aSNP\|_T_F | ATCCTAGACCTCCAGGTGGAATGATC |
| 295 | rs17642714_aSNP\|_T_F | CTTGGCTGTCTCAATATTTTGGAGTAAG |
| 296 | rs1800414_aSNP\|_T_F | GAGTAAATGAGCTGTGGTTTCTCTCTTA |
| 297 | rs1834619_aSNP\|_T_F | CTTTCCATGTGGACCCTTTAACATTCAG |
| 298 | rs1876482_aSNP\|_T_F | GCATAGTGAGCTGTTGATAGAGCTTTTG |
| 299 | rs1919550_aSNP\|_T_F | CTAGAACAAAATCATTGGCTCTCCTAGT |
| 300 | rs192655_aSNP\|_T_F | GTCTGGTGAGTACTGGCTGAATGTAAA |
| 301 | rs200354_aSNP\|_T_F | CCAGAGGATGCTGCTAAACATTCTACAA |
| 302 | rs2024566_aSNP\|_T_F | GCTCATGCCTGGAATTCACCTTTATTTT |
| 303 | rs2042762_aSNP\|_T_F | CTAACTAGACATTTGGGCCACCTTACTT |
| 304 | rs2166624_aSNP\|_T_F | GTCTATGGTGCCTATAGAATGTACAGGT |
| 305 | rs2196051_aSNP\|_T_F | CCCTCTCAAGTTTGTGAGCAAATATCAC |
| 306 | rs2238151_aSNP\|_T_F | CTCTATCTTGCTGCAATGGACTTTCC |
| 307 | rs260690_aSNP\|_T_F | CCTAGAAACAGATTTTGAAGGGCTCTTG |
| 308 | rs2814778_aSNP\|_T_F | AAATGAGGGGCATAGGGATAAGGGA |
| 309 | rs310644_aSNP\|_T_F | CCTAGAAATCTGATACGTTATCCTATGA |
| 310 | rs3737576_aSNP\|_T_F | AGGAGAGATATATTCAACATGAACCCAA |
| 311 | rs3811801_aSNP\|_T_F | GAACATCTCTGACCAGAAATTTCCAGTA |
| 312 | rs3823159_aSNP\|_T_F | GTGTAGTGAAATCCTTAGACTTAGGTAA |

TABLE 3-continued

SNP targeted primer sequences

| SEQ ID NO | SNP PRIMER | EXAMPLES OF SNP PRIMERS WITHOUT TAGS |
|---|---|---|
| 313 | rs3916235_aSNP\|_T_F | AATACATGAAAAAGTAATACATGGGCA |
| 314 | rs4471745_aSNP\|_T_F | ATTAAATGTTTACTTCTATCTACAAGGA |
| 315 | rs4833103_aSNP\|_T_F | CATTTTGTGAAATGCAAAGGGCAAATCT |
| 316 | rs4891825_aSNP\|_NU_T_F | GCTGAGAGGCTTAATTCCATCAAGATGA |
| 317 | rs4918664_aSNP\|_NU_T_F | CCCATCCTAAACTTAGTTTTATGGGCAG |
| 318 | rs6754311_aSNP\|_T_F | GTAACACATTCTCTTTGGGAAGCTAGC |
| 319 | rs6990312_aSNP\|_NU_T_F | CTTAGCTTCAGTGAAAATGGTTCCTCTC |
| 320 | rs7226659_aSNP\|_NU_T_F | CTTTCTTAGCTCCTCTCCATTTCTCTTC |
| 321 | rs7326934_aSNP\|_NU_T_F | GTCTATGCAGTGCTTCACTGAGGATTAT |
| 322 | rs735480_aSNP\|_NU_T_F | CTCTATCTGCTCAGAGCCTGCTTAAAAG |
| 323 | rs7554936_aSNP\|_NU_T_F | GGAAAGGATACAGTGTTGAGCAAGATAG |
| 324 | rs7657799_aSNP\|_NU_T_F | GCCAACTTGATTCTCTTTCAAATGCTTG |
| 325 | rs7722456_aSNP\|_T_F | AGATGGGGTTTACCATGTTTCCCAG |
| 326 | rs798443_aSNP\|_T_F | GTACAGTAGTTAGTTTCCAGACTGATGA |
| 327 | rs7997709_aSNP\|_T_F | GTAAATATCTAACTGTGTTTCCCTCAGT |
| 328 | rs870347_aSNP\|_T_F | GAACCAAAAGGAATTAAGAGACTAGGGG |
| 329 | rs917115_aSNP\|_T_F | CTGCTTTTACGGCTTCTTCCTTTCTTC |
| 330 | rs10497191_aSNP\|_S_R | CCCACATCCTTCCCATTTATAGGCAA |
| 331 | rs1079597_aSNP\|_S_R | TACATGATCCTAAGGGCAGCAGGAA |
| 332 | rs11652805_aSNP\|_S_R | GTTTGGTGCATCCTCTTTCTCTCTC |
| 333 | rs1229984_aSNP\|_S_R | GACTGTAGTCACCCCTTCTCCAACA |
| 334 | rs12439433_aSNP\|_S_R | AGAGTGAAATACATAGAAAAGAAACTTAAAG |
| 335 | rs12498138_aSNP\|_S_R | ATTTGCGAGAAACAGATAAATATTGAAG |
| 336 | rs12913832_pSNP\|_NU_S_R | ACAGGAACAAAGAATTTGTTCTTCATGG |
| 337 | rs1426654_aSNP\|_S_R | CCTTGGATTGTCTCAGGATGTTGCA |
| 338 | rs1462906_aSNP\|_S_R | CTGGGATGTTTGTTTTGGCTTTGTG |
| 339 | rs1572018_aSNP\|_S_R | ATTGGTAGTACACTAATGGATATATGTGAG |
| 340 | rs16891982_aSNP\|_S_R | GAATAAAGTGAGGAAAACACGGAGTTG |
| 341 | rs174570_aSNP\|_S_R | GAGAGAGGCAGAAAGGAGGGATGAA |
| 342 | rs17642714_aSNP\|_S_R | TACTCTGTCTTCAGTAGCTGTTTCTTGG |
| 343 | rs1800414_aSNP\|_S_R | TTAGACTCACCAAGATCAAGATGAATGC |
| 344 | rs1834619_aSNP\|_S_R | ATCTCAATAAAGCTGTTCAAAACAGAAAG |
| 345 | rs1876482_aSNP\|_S_R | TAAAGAAAATGCCATGGGCTGTACCC |
| 346 | rs1919550_aSNP\|_S_R | ATTGTGCAGCAGAACAGAGTGTAGTG |
| 347 | rs192655_aSNP\|_S_R | ATTCTTTGCATAGCTCACGAAATTTCCC |
| 348 | rs200354_aSNP\|_S_R | AAAATGAGACCTCGTATCTTTGCAGC |
| 349 | rs2024566_aSNP\|_S_R | AAATGCAGAACTGCCAAAAGAAACCC |
| 350 | rs2042762_aSNP\|_S_R | GAGAATCTGTGAATGCCAGGGTCTG |

TABLE 3-continued

SNP targeted primer sequences

| SEQ ID NO | SNP PRIMER | EXAMPLES OF SNP PRIMERS WITHOUT TAGS |
|---|---|---|
| 351 | rs2166624_aSNP\|_S_R | ATGGATTCATGTTTCAGACATCTAATT |
| 352 | rs2196051_aSNP\|_S_R | ATCACTAGAAAGAAAAGAGTTCCTATTC |
| 353 | rs2238151_aSNP\|_S_R | GAAGTTTAAAAGAGTGGGAACATGGGG |
| 354 | rs260690_aSNP\|_S_R | CTACGTAAGCAAAAATGATCACGCAC |
| 355 | rs2814778_aSNP\|_S_R | AACCTGATGGCCCTCATTAGTCCTT |
| 356 | rs310644_aSNP\|_S_R | CACCAGATTTCTAGGAATAGCATGTGAG |
| 357 | rs3737576_aSNP\|_S_R | AAGAGCATAGTGAGGGGTTAGACCT |
| 358 | rs3811801_aSNP\|_S_R | CTTTATATTTAGTGTAGAGATCAGTCTCC |
| 359 | rs3823159_aSNP\|_S_R | TGAGTCCTTTACCTAATCTTGGTTGTC |
| 360 | rs3916235_aSNP\|_S_R | AATCCAAAGCAACTCTCTTTTCACCAC |
| 361 | rs4471745_aSNP\|_S_R | TTTACTGGAACCCTGATTTTGTTGGA |
| 362 | rs4833103_aSNP\|_S_R | TGCCACTGATATATCAGTACCTGAGT |
| 363 | rs4891825_aSNP\|_NU_S_R | ACAATCTCAATCCCCCTTAATGTTTTC |
| 364 | rs4918664_aSNP\|_NU_S_R | GTGGGCAGAGAGAGTAAGAGAACCT |
| 365 | rs6754311_aSNP\|_S_R | CAAACCAGATTCTGGCAGAATAGTTAGC |
| 366 | rs6990312_aSNP\|NU_S_R | CTTCTCTCCCATCCTCCTTCTCCAC |
| 367 | rs7226659_aSNP\|_NU_S_R | AGATCAAGGGATCTGTGGGACAATAAC |
| 368 | rs7326934_aSNP\|_NU_S_R | GGGGAGTGATTTCAAGCATCCTGATT |
| 369 | rs735480_aSNP\|_NU_S_R | CATGAGTTTGAGGTAAGATGAAGGAGA |
| 370 | rs7554936_aSNP\|_NU_S_R | TCTCTCTCATCCTAGTGAATGCCATC |
| 371 | rs7657799_aSNP\|_NU_S_R | GGGTGATGATCTACCTTGCAGGTATA |
| 372 | rs7722456_aSNP\|_S_R | CTCAAGGCCCTGGGTCTGAAATTAC |
| 373 | rs798443_aSNP\|_S_R | ACATCTCCAGTTAATAATTTCCACTAAC |
| 374 | rs7997709_aSNP\|_S_R | TGGATTGCTCAACAAATAGTGCTAAAA |
| 375 | rs870347_aSNP\|_S_R | CATGCGACATCCAGGTAGCTAAAATAC |
| 376 | rs917115_aSNP\|_S_R | ATGGATAAAAATGGAACTTTCAAGAGAA |
| 377 | rs12203592_pSNP\|_T_F | GTTTTATGTAAAGCTTCGTCATATGGCT |
| 378 | rs12821256_pSNP\|_T_F | GTTCCAACTTAGTCATAAAGTTCCCTGG |
| 379 | rs12896399_pSNP\|_T_F | GGGTCTTGATGTTGTATTGATGAGGAAG |
| 380 | rs1393350_pSNP\|_T_F | CCTAACAGAAAGTCACTGTTTGTATCTG |
| 381 | rs1800407_pSNP\|_T_F | TCACTCTGGCTTGTACTCTCTCTGTG |
| 382 | rs2378249_pSNP\|_T_F | GGCTGGTTTCAGTCTGGAGACTTTATTT |
| 383 | rs2402130_pSNP\|_T_F | CTTCACCTCGATGACGATGATGATGAT |
| 384 | rs4959270_pSNP\|_T_F | GACAATAACAGCACAAAGGATGGAAAAG |
| 385 | rs1805009_pSNP\|_T_F | GAACCAGACCACACAATATCACCAC |
| 386 | rs28777_pSNP\|_T_F | TCTACCTCTTTGATGTCCCCTTCGATAG |
| 387 | rs16891982_pSNP\|_T_F | CAGAGTTTCTCATCTACGAAAGAGGAGT |
| 388 | rs683_pSNP\|_T_F | CCCAGCTTTGAAAAGTATGCCTAGAACT |

TABLE 3-continued

SNP targeted primer sequences

| SEQ ID NO | SNP PRIMER | EXAMPLES OF SNP PRIMERS WITHOUT TAGS |
|---|---|---|
| 389 | rs12913832_pSNP\|_T_F | CTGCTTCAAGTGTATATAAACTCACAGT |
| 390 | rs12203592_pSNP\|_S_R | TTGTTTCATCCACTTTGGTGGGTAAAAG |
| 391 | rs12821256_pSNP\|_S_R | TAATTAAGCTCTGTGTTTAGGGTTTTT |
| 392 | rs12896399_pSNP\|_S_R | CAATTCTTTGTTCTTTAGGTCAGTATAT |
| 393 | rs1393350_pSNP\|_S_R | TACTCTTCCTCAGTCCCTTCTCTGC |
| 394 | rs1800407_pSNP\|_S_R | TGAGACAGAGCATGATGATCATGGC |
| 395 | rs2378249_pSNP\|_S_R | GCACAAGTCTAGGAACTACTTTGCAC |
| 396 | rs2402130_pSNP\|_S_R | GAAGTATTTGAACCATACGGAGCCC |
| 397 | rs4959270_pSNP\|_S_R | TGAGGAACACATCCAAACTATGACAC |
| 398 | rs1805009_pSNP\|_S_R | TTTCTCGCCCTCATCATCTGCAATG |
| 399 | rs28777_pSNP\|_SR | TCAGTTGATTTCATGTGATCCTCACAG |
| 400 | rs16891982_pSNP\|_S_R | GAATAAAGTGAGGAAAACACGGAGTTG |
| 401 | rs683_pSNP\|_S_R | ATTACCTTCTTTCTAATACAAGCATATG |
| 402 | rs12913832_pSNP\|_S_R | ACAGGAACAAAGAATTTGTTCTTCATGG |

In some embodiments, the plurality of primers includes one or more primers including the nucleotide sequence of one or more identity informative SNPs and STRs of WO 2015/126766, which is incorporated below.

TABLE 4

Identity informative SNPs and STRs

Identity informative SNPs

| rs1005533 | rs1357617 | rs2076848 | rs4530059 | rs763869 |
| rs10092491 | rs1360288 | rs2107612 | rs4606077 | rs8037429 |
| rs1015250 | rs1382387 | rs2111980 | rs560681 | rs8078417 |
| rs1024116 | rs1413212 | rs214955 | rs576261 | rs826472 |
| rs1028528 | rs1454361 | rs221956 | rs6444724 | rs873196 |
| rs1029047 | rs1463729 | rs2269355 | rs6811238 | rs876724 |
| rs1031825 | rs1490413 | rs2342747 | rs6955448 | rs891700 |
| rs10488710 | rs1493232 | rs2399332 | rs7041158 | rs901398 |
| rs10495407 | rs1498553 | rs251934 | rs717302 | rs907100 |
| rs1058083 | rs1523537 | rs279844 | rs719366 | rs914165 |
| rs10773760 | rs1528460 | rs2830795 | rs722098 | rs917118 |
| rs10776839 | rs159606 | rs2831700 | rs722290 | rs938283 |
| rs1109037 | rs1736442 | rs2920816 | rs727811 | rs964681 |
| rs1294331 | rs1821380 | rs321198 | rs729172 | rs987640 |
| rs12997453 | rs1886510 | rs338882 | rs733164 | rs9905977 |
| rs13182883 | rs1979255 | rs354439 | rs735155 | rs9933934 |
| rs13218440 | rs2016276 | rs3780962 | rs737681 | rs9951171 |
| rs1335873 | rs2040411 | rs430046 | rs740598 | |
| rs1336071 | rs2046361 | rs4364205 | rs740910 | |
| rs1355366 | rs2056277 | rs445251 | rs7520386 | |

Autosomal STRs

| D1S1656 | CSF1PO | vWA | D21S11 | D4S2408 |
| D2S441 | D7S820 | D13S317 | TPOX | D17S1301 |
| D2S1338 | D8S1179 | Penta E | SE33 | D9S1122 |
| D3S1358 | D10S1248 | D16S539 | Penta D | D6S1043 |
| FGA | TH01 | D18S51 | D22S1045 | Amelogenin |
| D5S818 | D12S391 | D19S433 | D20S482 | |

X STRs

| DXS8378 | DXS8377 | DXS10101 | DXS10148 | DXS10146 |
| DXS7132 | DXS10135 | DXS10134 | DXS10079 | |
| HPRTB | DXS10074 | DXS7423 | DXS10103 | |

TABLE 4-continued

Identity informative SNPs and STRs

Y STRs

| DYS456 | DYS393 | DYS437 | DYS533 | DYS449 |
| DYS389I/II | DYS391 | DYS438 | DYS518 | DYS522 |
| DYS390 | DYS439 | DYS448 | DYS570 | DYS505 |
| DYS458 | DYS635 | DYS576 | DYS643 | DYS627 |
| DYS19 | DYS392 | DYS481 | DYS460 | DYF387S1a/b |
| DYS385a/b | YGATAH4 | DYS549 | DYS612 | |

In some embodiments, the plurality of primers includes one or more primers including the nucleotide sequence of one or more additional STRs and SNPs for multiplexing as listed in WO 2015/126766, which is incorporated below.

TABLE 5

Examples of additional STRs and SNPs for mulitplexing

Identity informative SNPs

| rs1004357 | rs1554472 | rs2567608 | rs521861 | rs9606186 |
| rs1019029 | rs1872575 | rs2811231 | rs5746846 | rs985492 |
| rs1027895 | rs2073383 | rs2833736 | rs590162 | rs9866013 |
| rs10500617 | rs2175957 | rs315791 | rs6591147 | |
| rs10768550 | rs2255301 | rs3744163 | rs689512 | |
| rs12480506 | rs2270529 | rs4288409 | rs7205345 | |
| rs13134862 | rs2272998 | rs464663 | rs7229946 | |
| rs1358856 | rs2291395 | rs4789798 | rs7704770 | |
| rs1410059 | rs2292972 | rs4796362 | rs8070085 | |
| rs1478829 | rs2503107 | rs4847034 | rs9546538 | |

Autosomal STRs

| D1S1677 | D3S4529 | D18S853 | D10S1435 |
| D11S4463 | D6S1017 | D14S1434 | D5S2500 |
| D1S1627 | D1GATA113 | D2S1776 | |

In some embodiments, the plurality of primers includes one or more primers including the nucleotide sequence of STRs and SNPs listed in WO 2015/126766, which is incorporated below.

TABLE 6

STRs and SNPs for databanking and case work

Identity informative SNPs

| | | | | |
|---|---|---|---|---|
| rs1005533 | rs1357617 | rs2076848 | rs4530059 | rs763869 |
| rs10092491 | rs1360288 | rs2107612 | rs4606077 | rs8037429 |
| rs1015250 | rs1382387 | rs2111980 | rs560681 | rs8078417 |
| rs1024116 | rs1413212 | rs214955 | rs576261 | rs826472 |
| rs1028528 | rs1454361 | rs221956 | rs6444724 | rs873196 |
| rs1029047 | rs1463729 | rs2269355 | rs6811238 | rs876724 |
| rs1031825 | rs1490413 | rs2342747 | rs6955448 | rs891700 |
| rs10488710 | rs1493232 | rs2399332 | rs7041158 | rs901398 |
| rs10495407 | rs1498553 | rs251934 | rs717302 | rs907100 |
| rs1058083 | rs1523537 | rs279844 | rs719366 | rs914165 |
| rs10773760 | rs1528460 | rs2830795 | rs722098 | rs917118 |
| rs10776839 | rs159606 | rs2831700 | rs722290 | rs938283 |
| rs1109037 | rs1736442 | rs2920816 | rs727811 | rs964681 |
| rs1294331 | rs1821380 | rs321198 | rs729172 | rs987640 |
| rs12997453 | rs1886510 | rs338882 | rs733164 | rs9905977 |
| rs13182883 | rs1979255 | rs354439 | rs735155 | rs993934 |
| rs13218440 | rs2016276 | rs3780962 | rs737681 | rs9951171 |
| rs1335873 | rs2040411 | rs430046 | rs740598 | |
| rs1336071 | rs2046361 | rs4364205 | rs740910 | |
| rs1355366 | rs2056277 | rs445251 | rs7520386 | |

Autosomal STRs

| | | | | |
|---|---|---|---|---|
| D1S1656 | CSF1PO | vWA | D21S11 | D4S2408 |
| D2S441 | D7S820 | D13S317 | TPOX | D17S1301 |
| D2S1338 | D8S1179 | Penta E | SE33 | D9S1122 |
| D3S1358 | D10S1248 | D16S539 | Penta D | D6S1043 |
| FGA | TH01 | D18S51 | D22S1045 | Amelogenin |
| D5S818 | D12S391 | D19S433 | D20S482 | |

X STRs

| | | | | |
|---|---|---|---|---|
| DXS8378 | DXS8377 | DXS10101 | DXS10148 | DXS10146 |
| DXS7132 | DXS10135 | DXS10134 | DXS10079 | |
| HPRTB | DXS10074 | DXS7423 | DXS10103 | |

Y STRs

| | | | | |
|---|---|---|---|---|
| DYS456 | DYS393 | DYS437 | DYS533 | DYS449 |
| DYS389I/II | DYS391 | DYS438 | DYS518 | DYS522 |
| DYS390 | DYS439 | DYS448 | DYS570 | DYS505 |
| DYS458 | DYS635 | DYS576 | DYS643 | DYS627 |
| DYS19 | DYS392 | DYS481 | DYS460 | DYF387S1a/b |
| DYS385a/b | YGATAH4 | DYS549 | DYS612 | |

Phenotypic informative SNPs

| | | | | |
|---|---|---|---|---|
| N29insA | rs1805006 | rs1110400 | rs12203592 | rs2378249 |
| rs11547464 | rs1805007 | rs28777 | rs1042602 | rs12896399 |
| rs885479 | rs1805009 | rs16891982 | rs1800407 | rs1393350 |
| rs1805008 | Y152OCH | rs12821256 | rs2402130 | rs683 |
| rs1805005 | rs2228479 | rs4959270 | rs12913832 | |

Ancestry informative SNPs

| | | | | |
|---|---|---|---|---|
| rs10497191 | rs17642714 | rs2238151 | rs4471745 | rs7554936 |
| rs1079597 | rs1800414 | rs2593595 | rs459920 | rs7657799 |
| rs11652805 | rs1834619 | rs260690 | rs4833103 | rs57722456 |
| rs1229984 | rs1871534 | rs2814778 | rs4891825 | rs798443 |
| rs12439433 | rs1876482 | rs310644 | rs4918664 | rs7997709 |
| rs12498138 | rs1919550 | rs3737576 | rs671 | rs870347 |
| rs12913832 | rs192655 | rs3811801 | rs6754311 | rs917115 |
| rs1426654 | rs200354 | rs3814134 | rs6990312 | rs9522149 |
| rs1462906 | rs2024566 | rs3823159 | rs7226659 | |
| rs1572018 | rs2042762 | rs3827760 | rs7251928 | |
| rs16891982 | rs2166624 | rs3916235 | rs7326934 | |
| rs174570 | rs2196051 | rs4411548 | rs735480 | |

In some embodiments, the plurality of primers which may be subject to incorporation of a QCS and further ES sequences includes one or more primers including the nucleotide sequence of an Identity Informative SNP of ILLUMINA's FORENSEQ DNA Signature Prep kit. Identity informative SNP could be one or more of the group comprising rs10495407, rs1294331, rs1413212, rs1490413, rs560681, rs891700, rs1109037, rs12997453, rs876724, rs907100, rs993934, rs1355366, rs1357617, rs2399332, rs4364205, rs6444724, rs1979255, rs2046361, rs279844, rs6811238, rs13182883, rs159606, rs251934, rs338882, rs717302, rs13218440, rs1336071, rs214955, rs727811, rs321198, rs6955448, rs737681, rs917118, rs10092491, rs2056277, rs4606077, rs763869, rs1015250, rs10776839, rs1360288, rs1463729, rs7041158, rs3780962, rs735155, rs740598, rs826472, rs964681, rs10488710, rs1498553, rs2076848, rs901398, rs10773760, rs2107612, rs2111980, rs2269355, rs2920816, rs1058083, rs1335873, rs1886510, rs354439, rs1454361, rs4530059, rs722290, rs873196, rs1528460, rs1821380, rs8037429, rs1382387, rs2342747, rs430046, rs729172, rs740910, rs8078417, rs938283, rs9905977, rs1024116, rs1493232, rs1736442, 9951171, rs576261, rs719366, rs1005533, rs1031825, rs1523537, rs445251, rs221956, rs2830795, rs2831700, rs722098, rs914165, rs1028528, rs2040411, rs733164, rs987640.

In some embodiments, the plurality of primers which may be subject to incorporation of a QCS and further ES sequences includes one or more primers including the nucleotide sequence of an autosomal STR or ITR of ILLUMINA's FORENSEQ DNA Signature Prep kit. Autosomal STRs could be one or more of the group comprising D1S1656, TPDX, D2S441, D2S1338, D3S1358, D4S2408, FGA, D5S818, CSF1PO, D6S1043, D7S820, D8S1179, D9S1122, D10S1248, TH01, vWA, D12S391, D13S317, Penta D, Penta E, D16S539, D17S1301, D18S51, D19S433, D20S482, D21S11, D22S1045.

In some embodiments, the plurality of primers which may be subject to incorporation of a QCS and further ES sequences includes one or more primers including the nucleotide sequence of a Y Haplotype Marker of ILLUMINA's FORENSEQ DNA Signature Prep kit. Y haplotype markers could be one or more of the group comprising DYF387S1, DYS19, DYS385a-b, DYS389I, DYS389II, DYS390, DYS391, DYS392, DYS437, DYS438, DYS439, DYS448, DYS460, DYS481, DYS505, DYS522, DYS533, DYS549, DYS570, DYS576, DYS612, DYS635, DYS643, Y-GATA-H4.

In some embodiments, the plurality of primers which may be subject to incorporation of a QCS and further ES sequences includes one or more primers including the nucleotide sequence of an X Haplotype Marker of ILLUMINA's FORENSEQ DNA Signature Prep kit. X haplotype markers could be one or more of the group comprising DXS10074, DXS10103, DXS10135, DXS7132, DXS7423, DXS8378, HPRTB.

In some embodiments, the plurality of primers which may be subject to incorporation of a QCS and further ES sequences includes one or more primers including the nucleotide sequence of a Phenotype Informative SNP of ILLUMINA's FORENSEQ DNA Signature Prep kit. Phenotypic informative SNPs could be one or more of the group comprising rs28777, rs12203592, rs4959270, rs683, rs1042602, rs1393350, rs12821256, rs12896399, rs2402130, rs1800407, N29insA, rs1110400, rs11547464, rs1805005, rs1805006, rs1805007, rs1805008, rs1805009, rs201326893_Y152OCH, rs2228479, rs885479, rs2378249, rs2814778, rs3737576, rs7554936, rs10497191, rs1834619, rs1876482, rs260690, rs3827760, rs6754311, rs798443, rs12498138, rs1919550, rs1229984, rs3811801, rs4833103, rs7722456, rs870347, rs16891982, rs192655, rs3823159, rs917115, rs1462906, rs1871534, rs2196051, rs6990312, rs3814134, rs4918664, rs1079597, rs174570, rs2238151, rs671, rs1572018, rs2166624, rs7326934, rs7997709, rs9522149, rs200354, rs12439433, rs1426654, rs1800414, rs735480, rs12913832, rs459920, rs11652805, rs17642714, rs2593595, rs4411548, rs4471745, rs2042762, rs3916235, rs4891825, rs7226659, rs7251928, rs310644, rs2024566.

In some embodiments, the plurality of primers which may be subject to incorporation of a QCS and further ES sequences includes one or more primers including the nucleotide sequence of an Ancestry Informative SNP of ILLUMINA's FORENSEQ DNA Signature Prep kit.

Ancestry information SNPs could be one or more of the group comprising rs2814778, rs3737576, rs7554936, rs10497191, rs1834619, rs1876482, rs260690, rs3827760, rs6754311, rs798443, rs12498138, rs1919550, rs1229984, rs3811801, rs4833103, rs7657799, rs7722456, rs870347, rs16891982, rs192655, rs3823159, rs917115, rs1462906, rs1871534, rs2196051, rs6990312, rs3814134, rs4918664, rs1079597, rs174570, rs2238151, rs671, rs1572018, rs2166624, rs7326934, rs7997709, rs9522149, rs200354, rs12439433, rs1426654, rs1800414, rs735480, rs12913832, rs459920, rs11652805, rs17642714, rs2593595, rs4411548, rs4471745, rs2042762, rs3916235, rs4891825, rs7226659, rs7251928, rs310644, rs2024566.

Correction of Amplification Bias

In some embodiments, each pair of a plurality of primer pairs directed toward a particular target includes one of the forward or reverse primers or both including a QCS selected from the group consisting of QCS1, QCS2, QCS3, QCS4, QCS5, QCS6, QCS7, and QCS8, and the other primer, either forward or reverse, including a QCS selected from the group consisting of QCS1, QCS2, QCS3, QCS4, QCS5, QCS6, QCS7, and QCS8. In other embodiments, for a primer pair of a plurality of primer pairs, the forward primer could have no QCS while the reverse primer could include one of eight QCS or the reverse primer could have no QCS while the forward primer could have one of eight QCS. The QCS sequences could be the same or different. Table 6 lists the possible QCS options, whereas a forward primer could include one of eight different QCS options and the reverse primer could include one of eight different QCS options depending on what should be implemented to reduce amplification bias and correct distorted polynucleotide ratios which can occur when amplifying a STR that is repeated oa few number of times vs a STR that repeats itself a large number of time. For example, CSF1PO has observed alleles with AGAT repeated from 5 to 16 times. Implementing a QCS on one or both of the primers in the pair for amplification of CSF1PO can help correct bias observed when trying to amplify a smaller allele (5 repeats) and a larger allele (13) simultaneously, for example. The same can also be done for inter-reaction primers such as, for example, a biased amplification that might be the result of a STR repeat for one STR target and a different STR target, one having a smaller number of STR repeats and the other a larger number of repeats of a particular STR (FIG. 1).

TABLE 7

QCS sequence options for a primer pair

| Forward primer | Reverse primer |
|---|---|
| No QCS | No QCS |
| QCS1 | QCS1 |
| QCS2 | QCS2 |
| QCS3 | QCS3 |
| QCS4 | QCS4 |
| QCS5 | QCS5 |
| QCS6 | QCS6 |

TABLE 7-continued

QCS sequence options for a primer pair

| Forward primer | Reverse primer |
|---|---|
| QCS7 | QCS7 |
| QCS8 | QCS8 |

Minimize or Eliminate Primer-Dimers

In some embodiments, one or more primers from the plurality of primers includes one or more QCSs. In some embodiments, one or more primers from the plurality of primers includes a QCS sequence selected from QCS1, QCS2, QCS3, QCS4, QCS5, QCS6, QCS7 and QCS8 a second or more different primers from the plurality of primers also includes a QCS sequence selected from QCS1, QCS2, QCS3, QCS4, QCS5, QCS6, QCS7 and QCS8. Table 7 lists the different options for QCS combination of an exemplary first and second primer from a plurality of primers. In essence, one primer could have one of eight different QCS choices, a second primer could have a choice of one to eight different QCS choices, a third, fourth, fifth, etc. primer of a plurality of primers which could also include any of the eight QCS sequences. As such, if primer-dimers are observed one or both of the primers that is contributing to the primer dimer could include from one to eight different QCS in order to diminish or eliminate the observed primer-dimer.

TABLE 8

QCS sequence options for two primers in a plurality of primers

| Primer 1 | Primer 2 |
|---|---|
| No QCS sequence | No QCS sequence |
| QCS1 | QCS1 |
| QCS2 | QCS2 |
| QCS3 | QCS3 |
| QCS4 | QCS4 |
| QCS5 | QCS5 |
| QCS6 | QCS6 |
| QCS7 | QCS7 |
| QCS8 | QCS8 |

Kits and Systems

In another aspect, provided herein is a kit including an oligonucleotide composition provided herein. In some embodiments, the kit is for use in a DNA profiling method, such as a forensic DNA profiling method, a paternity testing method, or an ancestry analysis method.

In some embodiments, the kit includes an oligonucleotide composition that includes a plurality of primers, each primer including a TS and wherein the plurality of primers includes two or more QCS selected from QCS1, QCS2, QCS3, QCS4, QCS5, QCS6, QCS7, and QCS8. In some embodiments, one or more of the plurality of primers includes an ES.

In some embodiments, two or more primers of the plurality of primers are stored as a primer pool, e.g., in a single tube, or a single well of a multiwell plate. In some embodiments, all primers of the plurality of primers are stored in a single primer pool. In other embodiments, primers are stored in more than one primer pool, for example, two, three or four primers pools.

In some embodiments, two of more of the plurality of primers are stored separately, e.g., a primer is stored in a separate tube or a separate well of a multiwell plate.

In some embodiments, the kit includes instructions for using the components of the kit. In some embodiments, the instructions describe a method provided herein, e.g., a forensic DNA profiling method.

Sequencing Methodologies

In some embodiments, the method includes preparing a DNA sequencing library using the amplified target polynucleotides from the sample.

In some embodiments, the method includes sequencing the DNA sequencing library, e.g., by next generation sequencing.

In some embodiments, the methods for amplifying or sequencing target polynucleotides of interest provided herein, using the oligonucleotide compositions provided herein, yield higher quality sequencing data for one or more target polynucleotides of interest compared to a method using other oligonucleotide compositions, such as oligonucleotide compositions in which all primers lack a QCS or ES sequence, or oligonucleotide compositions including different pluralities of primers (e.g., each plurality of primers having a different TS), in which all primers share the same QCS (e.g., a fully randomized QCS).

In some embodiments, using an oligonucleotide composition provided herein, in a sequencing method provided herein increases the sequencing information obtained for one or more target polynucleotides of interest (e.g., in % of aligned reads, limit of detection and quantitative accuracy for target polynucleotide) by 1.5-fold, 2.0-fold, 2.5-fold, 3.0-fold, 3.5-fold, 4.0-fold, 4.5-fold, or 5.0-fold relative to a comparable method using another oligonucleotide composition, such as an such as oligonucleotide compositions in which all primers lack a QCS or ES sequence, or oligonucleotide compositions including different pluralities of primers (e.g., each plurality of primers having a different TS), in which all primers share the same QCS (e.g., a fully randomized QCS).

In some embodiments, using an oligonucleotide composition provided herein in a sequencing method provided herein can increase the sequencing information obtained for one or more target polynucleotides of interest to 50% or more, 60% or more, 70% or more, 80% or more, 90% or more, 95% or more, or 99% or more % of aligned reads, whereas using another oligonucleotide composition in which all primers lack a QCS or ES sequence or in which different pluralities of primers (e.g., with different TS) all share the same QCS (e.g., a fully randomized QCS) yields less than 50%, less than 40%, less than 30%, less than 20%, less than 10%, or less than 5% of aligned reads for the one or more target polynucleotides of interest.

In some embodiments, using an oligonucleotide composition provided herein in a sequencing method provided herein can increase the sequencing information obtained for one or more target polynucleotides of interest to 80% or more (e.g., % of aligned read from a sequencing library), whereas using another oligonucleotide composition in which different pluralities of primers (e.g., with different TS) all have a fully randomized QCS yields less than 50% (e.g., about 40%) of aligned reads for the one or more target polynucleotides of interest.

In another aspect, provided herein are methods for amplifying or sequencing a plurality of target polynucleotides in a sample including assembling an oligonucleotide composition provided herein. In some embodiments, the methods include sequencing the plurality of amplified target polynucleotides. In some embodiments, the oligonucleotide composition includes a plurality of primers, wherein each primer includes a target nucleic acid specific sequence (TS) and a quality control sequence (QCS), wherein the plurality of primers includes two or more QCS of QCS1, QCS2, QCS3, QCS4, QCS5, QCS6, QCS7, and QCS8. In some embodiments, the oligonucleotide composition includes one or more primers including a TS, a QCS, and an ES. In some embodiments, the oligonucleotide composition includes one or more primers including a TS and not including a QCS or an ES. In some embodiments, the oligonucleotide composition includes a plurality of primers including a TS and a QCS, wherein each primer includes a target nucleic acid specific sequence (TS) and a quality control sequence (QCS), wherein the plurality of primers includes two or more QCS of QCS1, QCS2, QCS3, QCS4, QCS5, QCS6, QCS7, and QCS8, and the composition includes one or more primers including a TS, a QCS, and an ES. In some embodiments, the oligonucleotide composition includes a plurality of primers including a TS and a QCS, wherein each primer includes a target nucleic acid specific sequence (TS) and a quality control sequence (QCS), wherein the plurality of primers includes two or more QCS of QCS1, QCS2, QCS3, QCS4, QCS5, QCS6, QCS7, and QCS8, the composition includes one or more primers including a TS, a QCS, and an ES, and the composition includes one or more primers including a TS and not including a QCS and an ES.

In some embodiments, sequencing a library including a plurality of target polynucleotides of interest that was produced by amplifying the target polynucleotides using an optimized primer pool or an oligonucleotide composition provided herein yields more than 50%, more than 60%, more than 70%, more than 80%, more than 90%, more than 95%, or more than 99% of aligned reads (% library output) for the target polynucleotides, whereas sequencing a library including the plurality of target polynucleotides of interest that was produced by amplifying the target polynucleotides using the initial primer pool (e.g., a primer pool of P-TS-QCS1 primers alone) yields less than 50%, less than 40%, less than 30%, less than 20%, less than 10%, less than 5%, less than 3%, less than 1%, or less than 0.1% of aligned reads (% library output) for the target polynucleotides.

In some embodiments, sequencing a library including a plurality of target polynucleotides of interst that was produced by amplifying the target polynucleotides using an optimized primer pool or an oligonucleotide composition provided herein yields more than 80% of aligned reads (% library output) for the target polynucleotides, whereas sequencing a library including the plurality of target polynucleotides of interest that was produced by amplifying the target polynucleotides using the initial primer pool (e.g., a primer pool of P-TS-QCS1 primers alone) yields less than 0.1% of aligned reads (% library output) for the target polynucleotides.

The present methods are not limited to any particular sequencing platform and are exemplified here in regards to SBS, or sequence by synthesis, type of parallel sequencing. Particularly applicable techniques are those wherein nucleic acids are attached at fixed locations in an array such that their relative positions do not change and wherein the array is repeatedly imaged. Examples in which images are obtained in different color channels, for example, coinciding with different labels used to distinguish one nucleotide base type from another are particularly applicable.

SBS techniques generally involve the enzymatic extension of a nascent nucleic acid strand through the iterative addition of nucleotides against a template strand. In traditional methods of SBS, a single nucleotide monomer may be provided to a target polynucleotide in the presence of a polymerase in each delivery. However, in the methods described herein, more than one type of nucleotide monomer can be provided to a target nucleic acid in the presence of a polymerase in a delivery.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate, or the like. In some examples where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Some examples include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11 (1), 3-11; Ronaghi, M, Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another example of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91 /06678 and W 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides. Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some examples can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a. second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some examples can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment, of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some examples can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:61 1-615 (2003), the disclosures of which are incorporated herein by reference in their entireties). In such embodiments, the target nucleic acid passes through a nanopore. The nanopore can be a synthetic pore or biological membrane protein, such as □-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nueleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some examples can utilize methods involving the real-time monitoring of DNA polymerase activity. Nucleotide incorporations can be detected through fluorescence resonance energy transfer (FRET) interactions between a fluorophore-bearing polymerase and y-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. j. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nanostructures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PGR as described in further detail below.

Primer Assembly and Optimization

The oligonucleotide compositions provided herein can, e.g., be assembled in an iterative process or in a parallel process.

In some embodiments, an oligonucleotide composition provided herein is assembled in an iterative process. Generally, in the iterative process, an initial pool of primers is designed, e.g., computationally, to amplify a plurality of target polynucleotides of interest. The primers in the initial pool can, e.g., each include a TS and a QCS. The QCS in the primers of the initial pool can be of the same type (e.g., QCS1, QCS2, QCS3, QCS4, QCS5, QCS6, QCS7, or QCS8) for each primer in the initial pool, or different primers in the initial pool can have different QCSs. In some embodiments, all primers of the initial pool comprise a QCS1, which is a fully randomized sequence. An oligonucleotide composition provided herein can be assembled, e.g., as an optimized pool of primers, using an iterative process provided herein, e.g., by a) testing the initial pool of primers for the ability of each primer (or primer pair) to amplify a target polynucleotide of interests from a sample; b) identifying separate subgroups of primers that are capable or not capable of amplifying a target polynucleotide; c) independently modifying each primer not capable of amplifying a target polynucleotide; d) retesting the modified primers, e.g., either alone or in a pool with other primers that were previously identified as being capable of amplifying a target polynucleotide, and e) identifying separate subgroups of modified primers that are capable or not capable of amplifying a target polynucleotide. An optimized primer pool can, e.g., be produced by combining unmodified and modified primers that were identified as being capable of amplifying a target polynucleotide.

Any modified primers that remain incapable of amplifying a target polynucleotide can, optionally, be further modified and retested in one or more additional rounds of primer optimization. Any further modified primers that are capable of amplifying a target polynucleotide can also be added to an optimized primer pool.

Independent primer optimization can be continued, e.g., until the optimized primer pool includes primers capable of amplifying each target polynucleotide of interest. Primer modification at each step of the iterative process can include, e.g., modifying a primer's QCS, adding an ES, or modifying a primer's TS. Each primer can be modified independently of any other primer. For example, one primer in a plurality or subgroup of primers can be modified by modifying the primer's QCS, and another primer in the plurality or subgroup of primers can be modified by adding an ES. In some embodiments, in a given step in the iterative process, all primers selected for modification are modified by modifying the primer's QCS. In some embodiments, in a given step in the iterative process all primers selected for modification are modified by modifying the primer's ES. The iterative processes provided herein can optionally include sequencing of the amplified target polynucleotides.

In another aspect, provided herein is a method for assembling an oligonucleotide composition provided herein, including a) providing an initial primer pool including a plurality of primers (P), wherein each primer includes a TS and a QCS (P-TS-QCS primer); b) amplifying target polynucleotides from a sample using the initial primer pool; c) identifying a subgroup of primers (e.g., first subgroup) in the initial primer pool capable of detectably amplifying the target polynucleotides or identifying a subgroup of primers (e.g., second subgroup) in the initial primer pool not capable of detectably amplifying the target polynucleotides or only capable of low-level amplification of the target polynucleotides; d) independently modifying one or more primers in the subgroup of primers (e.g., second subgroup) capable of no or only low-level amplification of the target polynucleotides, whereby modifying includes i) modifying a primers' TS to TS' (P-TS'-QCS); ii) modifying a primers' QCS to QCS' (P-TS-QCS'), or iii) adding an ES to a primer (P-TS-QCS-ES); e) optionally identifying a subgroup of modified primers (e.g., third subgroup) capable of detectably amplifying a target polynucleotide or identifying a subgroup of modified primers (e.g., fourth subgroup) capable of no or only low-level amplification of a target polynucleotide, and f) optionally, combining primers and modified primers capable of detectably amplifying a target polynucleotide to produce an optimized primer pool.

In some embodiments, the QCS in each primer of the initial primer pool is a QCS1 (each position in the QCS1 is fully randomized).

In some embodiments, a primer of a first subgroup of primers is a P-TS-QCS primer capable of amplifying the primer's target polynucleotide to detectable levels.

In some embodiments, a primer of a second subgroup of primers is a P-TS-QCS primer not capable of amplifying the primer's target polynucleotide to detectable levels, or only capable of amplifying the primer's target polynucleotide to low-levels.

In some embodiments, a primer of a third subgroup of primers is a modified P-TS-QCS primer (e.g., a modified primer of the second subgroup of primers) that is capable of amplifying the primer's target polynucleotide to detectable levels. The primer of the third subgroup can be modified, e.g., to include a modified TS (TS'), a modified QCS (QCS'), or an ES.

In some embodiments, a primer of a fourth subgroup of primers is a modified P-TS-QCS primer (e.g., a modified primer of the second subgroup of primers) that is not capable of amplifying the primer's target polynucleotide to detectable levels, or only capable of amplifying the primer's target polynucleotide to low-levels. The primer of the fourth subgroup can be modified, e.g., to include a modified TS (TS'), a modified QCS (QCS'), or an ES.

In some embodiments, a primer of a fifth subgroup of primers is a modified P-TS-QCS primer or a modified P-TS-QCS-ES primer (e.g., a further modified primer of the fourth subgroup of primers) that is capable of amplifying the primer's target polynucleotide to detectable levels. The primer of the fourth subgroup can be further modified, e.g., to include a modified TS (e.g., TS'), a further modified TS (e.g., TS"), a modified QCS (e.g., QCS'), a further modified QCS (e.g., QCS"), an ES or a modified ES (e.g., ES'), or a combination thereof.

In some embodiments, a primer of a sixth subgroup of primers is a modified P-TS-QCS primer or a modified P-TS-QCS-ES primer (e.g., a further modified primer of the fourth subgroup of primers) that is not capable of amplifying the primer's target polynucleotide to detectable levels, or only capable of amplifying the primer's target polynucleotide to low-levels. The primer of the fourth subgroup can be further modified, e.g., to include a modified TS (e.g., TS') a further modified TS (e.g., TS"), a modified QCS (e.g., QCS'), a further modified QCS (e.g., QCS"), an ES or a modified ES (e.g., ES'), or a combination thereof.

In some embodiments, steps d) and e) are repeated two or more times (e.g., 2, 3, 4, 5, 6, 7, 8, 9, 10 times or more) to further modify the primers of a subgroup of primers, e.g., primers of a subgroup that are not capable of amplifying the primers' target polynucleotide from a sample or that are only capable of amplifying the primers' target polynucleotide to low levels. Further modifications can, e.g., be made to the primers TS (e.g., to yield a TS', TS", TS'", or the like), the primers' QCS (e.g., to yield a QCS', QCS", QCS'", or the like), or the primers' ES (e.g., to yield an ES', ES", ES'", or the like). Further modified primers can subsequently be used to amplify target polynucleotides to characterize additional subgroups of primers with respect to their ability to amplify the primers' target polynucleotides from a sample.

In some embodiments, independently modifying the one or more primers in d) includes modifying the one or more primers in the same manner.

In some embodiments, independently modifying the one or more primers in d) includes introducing a first modification to one or more primers and introducing a second modification to one or more different primers. In some embodiments, the first and second modifications are the same. In some embodiments, the first and second modifications are different.

In some embodiments, independently modifying the one or more primers in d) includes modifying each of the one or more primer by either i) modifying the primers' TS to TS' (P-TS'-QCS); ii) modifying the primers' QCS to QCS' (P-TS-QCS'), or iii) adding an ES to the primers (P-TS-QCS-ES).

In some embodiments, independently modifying the one or more primers in d) includes modifying one or more primers by modifying the primers' TS to TS' (P-TS'-QCS) and modifying one or more other primers by modifying the primers' QCS to QCS' (P-TS-QCS'), or by adding an ES to the primers (P-TS-QCS-ES).

In some embodiments, independently modifying the one or more primers in d) includes modifying one or more primers by modifying the primers' QCS to QCS' (P-TS-QCS') and modifying one or more other primers by modifying the primers' TS to TS' (P-TS'-QCS) or by adding an ES to the primers (P-TS-QCS-ES).

In some embodiments, independently modifying the one or more primers in d) includes modifying one or more primers by adding an ES to the primers (P-TS-QCS-ES) and modifying one or more other primers by modifying the primers' TS to TS' (P-TS'-QCS) or by modifying the primers' QCS to QCS' (P-TS-QCS').

In some embodiments, modifying a primer's QCS to QCS' includes replacing the primer's QCS with a QCS of a different type, e.g., replacing a QCS1 with a QCS2. In some embodiments, modifying a primer's QCS includes replacing the primer's QCS with a different QCS of the same type, e.g., replacing a QCS2 (e.g., QCS2(1) including one partially randomized position) with a different QCS2 (e.g., QCS2(2) including two partially randomized positions).

In some embodiments, adding an ES to a primer includes adding an ES to the 5'-end or the 3'-end of the QCS. In some embodiments, adding an ES to a primer includes adding an ES to both the 5'-end and the 3'-end of the QCS. In some embodiments, the ESs added on the 5'-end and the 3'-end of the QCS are the same ES. In some embodiments, the ESs added on the 5'-end and the 3'-end of the QCS are different ESs.

In some embodiments, the method includes e) using the modified primers of d) to amplify the modified primers' target polynucleotides of interest from the sample and identifying a subgroup of primers (e.g., third subgroup) resulting in detectable amplification of the primers' target polynucleotide or identifying a subgroup of primers (e.g., fourth subgroup) resulting in no detectable amplification or only low-level amplification of the primers' target polynucleotide from the sample.

In some embodiments, the method includes repeating d) and e) one or more times using the subgroup of primers of e) (e.g., fourth subgroup), which result in no detectable amplification or only low-level amplification of the primers' target polynucleotides, to obtain further subgroups of primers (e.g., fifth subgroup, sixth subgroup) that include one or more additional modifications, e.g., in a primer's TS or QCS sequence, or with respect to the presence or absence of an ES.

In some embodiments, the method includes producing an optimized primer pool. In some embodiments, the optimized primer pool includes one or more primers from the first subgroup of primers (P-TS-QCS). In some embodiments, the optimized primer pool includes one or more primers from the third subgroup of primers (e.g., P-TS-QCS', P-TS'-QCS, P-TS-QCS-ES). In some embodiments, the optimized primer pool includes one or more primers from the fifth subgroup of primers (e.g., P-TS'-QCS', P-TS'-QCS-ES, P-TS-QCS'-ES). In some embodiments, the optimized primer pool includes one or more primers from the first subgroup of primers and one or more primers from the third subgroup of primers. In some embodiments, the optimized primer pool includes one or more primers form the first subgroup of primers and one or more primers from the fifth subgroup of primers. In some embodiments, the optimized primer pool includes one or more primers from the third subgroup of primers and one or more primers from the fifth subgroup of primers. In some embodiments, the optimized primer pool includes one or more primers from the first subgroup of primers, one or more primers from the third subgroup of primers, and one or more primers from the fifth subgroup of primers.

In some embodiments, the methods provided herein comprise sequencing the plurality of target polynucleotides of interest following amplification of the target polynucleotides using an optimized primer pool or an oligonucleotide composition provided herein to produce a DNA sequencing library.

Figure 4:
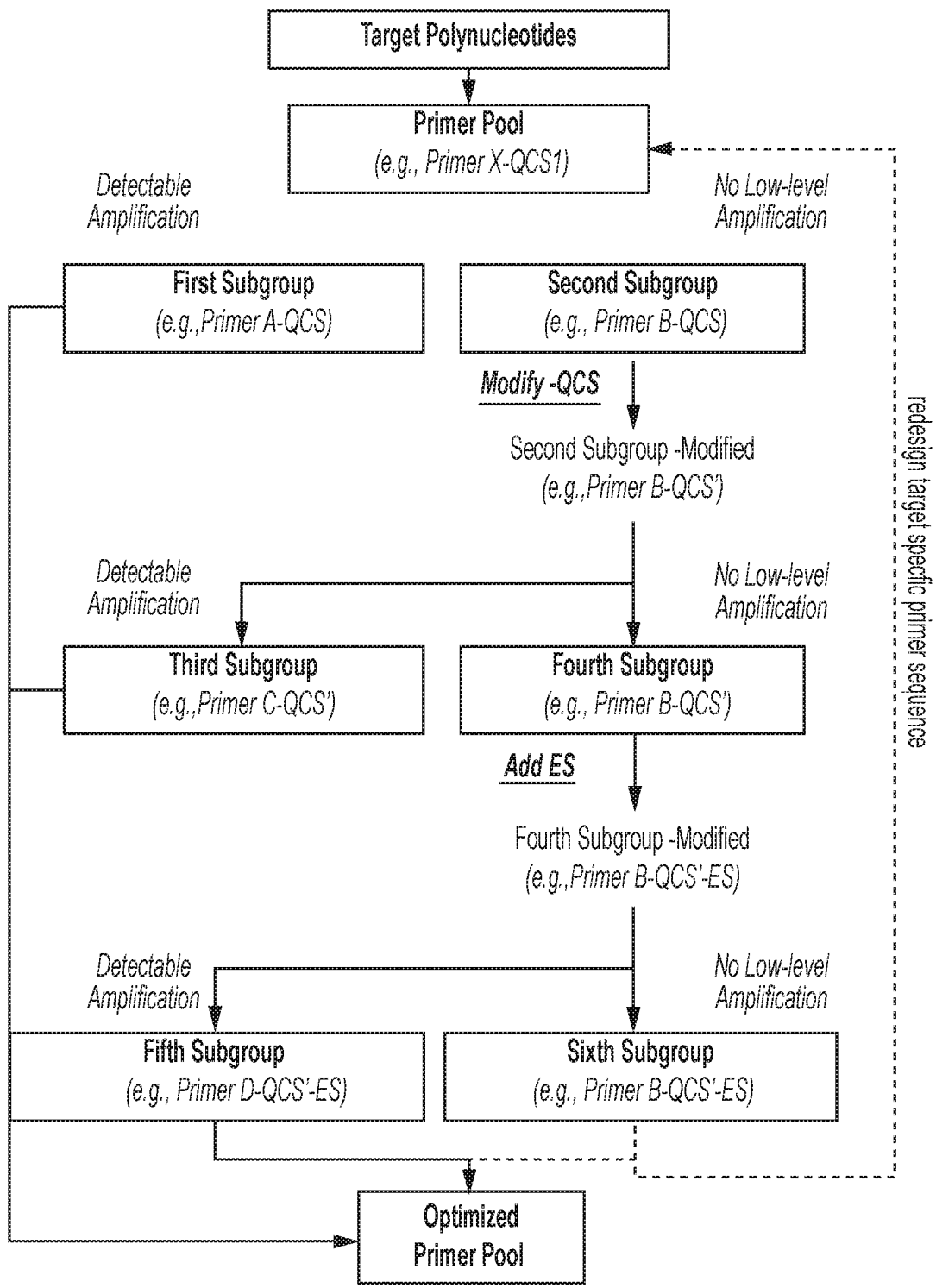
FIG. 4 shows a flow chart illustrating an exemplary iterative process for assembling an oligonucleotide composition provided herein.

An exemplary iterative method for assembling an oligonucleotide composition provided herein is illustrated in FIG. 4. In the method of FIG. 4, an initial pool of primers is designed, e.g., computationally to amplify a preselected set of target polynucleotides of interest from a sample. Primer3 software is used to design candidate primers for each target matching the assay PCR conditions. These candidates are scored and filtered based on their predicted interactions (e.g. dimer formation and off-target amplification) with each other in a multiplex PCR. Each primer (P) in the initial pool includes a TS and a QCS (e.g., each primer includes a fully randomized QCS, QCS1). The initial primer pool is then tested for the ability of individual primers to amplify a target polynucleic acid of interest from the sample. Primers that can amplify a target polynucleotide of interest from the sample are assigned to a first subgroup of primers (P-TS-QCS). P-TS-QCS primers resulting in no amplification or only low-levels of amplification of a target polynucleotide from the sample are assigned to a second subgroup of primers. Primers of the second subgroup of primers are then modified in their QCS (P-TS-QCS'). For example, a P-TS-QCS primer of subgroup two including a QCS1 can be modified to replace the QCS1 with a QCS2. The modified primers of the second subgroup (P-TS-QCS') are subsequently tested for the ability of individual primers to amplify a target polynucleotide of interest from the sample. Testing of the P-TS-QCS' primers can, e.g., be performed in a primer pool in the presence of the P-TS-QCS primers of the first subgroup. P-TS-QCS' primers that can amplify a target polynucleotide of interest from the sample are assigned to a third subgroup of primers. P-TS-QCS' primers resulting in no amplification or only low-level amplification of a target polynucleotide of interest from the sample are assigned to a fourth subgroup of primers. Primers of the fourth subgroup of primers are subsequently modified to incorporate an ES (e.g., on the 5'-end or the 3'-end of the QCS, or on both ends). The modified primers of the fourth subgroup (P-TS-QCS'-ES) are subsequently tested for the ability of individual primers to amplify a target polynucleotide of interest from the sample.

Testing of the P-TS-QCS'-ES primers can, e.g., be performed in a primer pool in the presence of the P-TS-QCS primers of the first subgroup, or the P-TS-QCS' primers of the third subgroup, or both. P-TS-QCS'-ES primers that can amplify a target polynucleotide of interest from the sample are assigned to a fifth subgroup of primers. P-TS-QCS'-ES primers resulting in no amplification or only low-level amplification of a target polynucleotide of interest from the sample are assigned to a sixth subgroup of primers. Primers of the sixth subgroup of primers can be optionally subjected to further optimization steps, which can, e.g., involve the redesign of the TS-sequence of the primer to a modified TS sequence (TS'). The TS'-primer (e.g., P-TS'-QCS) can be subjected to another iteration of the primer pool optimization method shown in FIG. 1. Alternatively, primers of the sixth subgroup can be added to an optimized primer pool. An exemplary optimized primer pool, e.g., as shown in FIG. 1, can include primers of some or all of the first subgroup of primers (P-TS), the third subgroup of primer (P-TS-QCS), and the fifth subgroup of primers (P-TS-QCS-ES).

In some embodiments, provided herein is a method for amplifying a plurality of target polynucleotides in a sample, including a) selecting a plurality of target polynucleotides of interest; b) designing an initial primer pool including a plurality of primers to amplify the plurality of polynucleotides, wherein each primer includes a target nucleic acid specific sequence (TS) and a first quality control sequence (QCS1), wherein each nucleic acid position in the QCS1 is fully randomized; c) analyzing the plurality of primers in a first amplification reaction to identify a first subgroup of primers resulting in detectable amplification of target nucleic acids in the sample and to identify a second subgroup of primers resulting in no detectable or minimally detectable amplification of the target nucleic acid in the sample; d) modifying the second subgroup of primers to replace the QCS1 with a QCS selected from the group consisting of QCS2, wherein one or more nucleic acid positions are partially randomized, QCS3, wherein one or more nucleic acid positions are fixed, QCS4, wherein all nucleic acid positions are fixed, QCS5, wherein one or more nucleic acid positions are fully randomized and one or more nucleic acid positions are partially randomized, QCS6, wherein one or more nucleic acid positions are fully randomized and one or more nucleic acid positions are fixed, QCS7, wherein one or more nucleic acid positions are partially randomized and one or more nucleic acid position are fixed, and QCS8, wherein one or more nucleic acid positions are fully randomized, one or more nucleic acid positions are partially randomized, and one or more nucleic acid positions are fixed; e) analyzing the modified second subgroup of primers in a second amplification reaction to identify a third subgroup of primers resulting in detectable amplification of the target nucleic acid in the sample and to identify a fourth subgroup of primers resulting in no detectable or minimally detectable amplification of the target nucleic acid in the sample; f) optionally modifying a primer from the fourth subgroup of primers to introduce an extension sequence (ES) flanking the 5'-end (5'ES) or the 3'-end (3'ES) of the QCS in the primer; g) optionally analyzing the modified fourth subgroup of primers in an amplification reaction to identify a fifth subgroup of primers resulting in detectable amplification of the target nucleic acid in the sample, and h) amplifying the plurality of target nucleic acids in the sample using an optimized primer pool including a combination of primers from the first, third, or fifth subgroup of primers.

In some embodiments, the method includes iteratively modifying primers from the first, second, third, or fourth subgroup of primers until primers have been identified that can detectably amplify each of the plurality of target nucleic acids of interest.

In some embodiments, the method includes modifying a primer from the first, second, or third subgroup of primers to add an extension sequence (ES) flanking the 5'-end (5'ES) or the 3'-end (3'ES) of the QCS in the primer. In primers including an adaptor sequence (AS) the 5'ES is positioned between the AS on the 5'-end of the primer and the QCS. The 3'ES is typically positioned between the QCS and the TS.

In some embodiments, adding a 5'ES to a primer in a plurality of primers, e.g., of the first, second or third subgroup, includes selecting the 5'ES. In some embodiments, designing the 5'ES includes identifying all primers in the plurality of primers that include a 3'-end which is complementary to a sequencing library adaptor (e.g., an Illumina adapter), and selecting the shortest nucleic acid sequence that is not complementary to a nucleic acid sequence in the identified primers as the ES to be added to the primer in the plurality of primers.

In some embodiments, adding the 3'ES to a primer in a plurality of primers, e.g., of the first, second or third subgroup, includes, optionally, selecting the length of the ES (e.g., 4 nucleic acids); discarding possible 3'ESs that are at least partly complementary to a nucleic acid sequence upstream of the target polynucleotide sequence recognized by the TS of a primer in the plurality of primers; identifying a primer in the plurality of primers whose 3'-ends at least partly complements the 5'-end of another primer in the plurality of primers; select an ES that complements the least number of potential dimer partners in the plurality of primers as the 3'ES, and add the 3'ES into the identified primer.

In some embodiments, the method includes sequencing the amplified plurality of target nucleic acids.

In some embodiments, sequencing a plurality of target nucleic acids using an optimized primer pool yields more than 50%, more than 60%, more than 70%, more than 80%, more than 90%, more than 95%, or more than 99% of aligned sequence reads, and sequencing the plurality of target nucleic acids using the initial primer pool yields less than 50%, less than 40%, less than 30%, less than 20%, less than 10%, less than 5%, less than 3%, less than 1%, or less than 0.1% of aligned sequence reads.

In some embodiments, the optimized primer pool includes one or more "primers selected from D16S359, D6S1043, DYS570, D19S433, PentaD, DYS576, AmelPP, DXS10135, D13S317, DYS389, D20S482, DXS10074, rs1805009, rs10776839, rs2831700, rs1042602, and rs1058083, DYS392, D22S1045, DYS19, DYS456, DYS439, and DYS635.

Examples of modified primer sequences containing QCS are provided in SEQ ID NO: 403-415 in Table 9. The sequences labeled as SEQ ID NO: 403-415 comprise the adapter sequence (shown in lowercase), the QCS (shown as NNNNN) and the gene-specific sequence (shown in uppercase italics).

TABLE 9

Example primer sequences modified with QCS

| SEQ ID | Sequence | Primer Name |
|---|---|---|
| SEQ ID NO: 403 | tacacgacgctcttccgatctNNNNN*CAAAGAAGTCAAAACAGAGGGATCA* | DYS392_F4_T |
| SEQ ID NO: 404 | tacacgacgctcttccgatctNNNNN*CAAAGGCAGATCCCAAGCTCT* | D16S539_F2_T |

TABLE 9-continued

Example primer sequences modified with QCS

| SEQ ID | Sequence | Primer Name |
|---|---|---|
| SEQ ID NO: 405 | tacacgacgctcttccgatctNNNNNCAATAGTGTGCAAGGATGGGTG | D61043_F1_T |
| SEQ ID NO: 406 | tacacgacgctcttccgatctNNNNNCAACCTAAGCTGAAATGCAGATATTC | DYS570_F1_ |
| SEQ ID NO: 407 | cttggcacccgagaattccaNNNNNAGGAGGTTGAGGCTGCAAAA | D19S433_R |
| SEQ ID NO: 408 | tacacgacgctcttccgatctNNNNNGCATGGTGAGGCTGAAGTAG | PentaD_F3_T |
| SEQ ID NO: 409 | tacacgacgctcttccgatctNNNNNGCARCTAGAATATAAGCAGGCAGGA | DYS456_F4_T |
| SEQ ID NO: 410 | tacacgacgctcttccgatctNNNNNGCAGTCTCATTTCCTGGAGATGAAGG | DYS576_F2_T |
| SEQ ID NO: 411 | tacacgacgctcttccgatctNNNNNCCCTGGGCTCTGTAAAGAA | AmelPP_F_T |
| SEQ ID NO: 412 | cttggcacccgagaattccaNNNNNGGAACACAATTATCCCTGAGTAGCAG | DYS389I_II_R3_Sm |
| SEQ ID NO: 413 | cttggcacccgagaattccaNNNNNGGACAGCCTCCATAWCCACATG | D20S482_R2-Sm |
| SEQ ID NO: 414 | cttggcacccgagaattccaNNNNNGCATCCRTGACTCTCTGGAC | D13S317_R2_Sm |
| SEQ ID NO: 415 | tacacgacgctcttccgatctNNNNNTGAAACTAAAGTCAAATGGGCTAC | DXS10135_F |

Examples of modified primer sequences containing QCS-ES are provided in SEQ ID NO: 416-428 in Table 10. The sequences labeled as SEQ ID NO: 416-428 comprise the adapter sequence (shown in lowercase), aSpacer-ES (shown in bold), the QCS (shown as random nucleotides N or non-random nucleotides B, D, or H), the gSpacer-ES (shown in bold underlined) and the gene-specific sequence (shown in uppercase italics). The non random nucleotides in the QCS are according to the IUPAC codes (B denotes a C or G or T; D denotes a A or G or T; H denotes a A or C or T).

target in the PCR multiplex reaction. The designed primers can be scoring and filtered by the software based on predicted interactions (e.g., primer dimer formation, off target amplification, etc.) that could occur in an amplification reaction. Primers could be split into subpools for experimental testing and determination of primer dimer formation occurrence, for example by aligning sequencing reads, running amplification products on a gel for primer dimer visualization, or any other qualitative or quantitative methodology known in that art. Primers that perform poorly, for

TABLE 10

Example primer sequences modified with QCS-ES

| SEQ ID | SEQUENCE | PRIMER NAME |
|---|---|---|
| SEQ ID NO: 416 | tacacgacgctcttccgatctTACGBNNND<u>CGCA</u>CAAAGAAGTCAAAACAGAGGGATCA | DYS392_F4_T |
| SEQ ID NO: 417 | tacacgacgctcttccgatctTACGBNNND<u>CGCT</u>CAAAGGCAGATCCCAAGCTCT | D16S539_F2_T |
| SEQ ID NO: 418 | tacacgacgctcttccgatctTACGBNNND<u>CGCT</u>CAATAGTGTGCAAGGATGGGTG | D61043_F1_T |
| SEQ ID NO: 419 | tacacgacgctcttccgatctTACGBNNND<u>CGCT</u>CAACCTAAGCTGAAATGCAGATATTC | DYS570_F1_T |
| SEQ ID NO: 420 | cttggcacccgagaattccaACGNNNNH<u>CCGG</u>AGGAGGTTGAGGCTGCAAAA | D19S433_R |
| SEQ ID NO: 421 | tacacgacgctcttccgatctTACGBNNND<u>CGCT</u>GCATGGTGAGGCTGAAGTAG | PentaD_F3_T |
| SEQ ID NO: 422 | tacacgacgctcttccgatctTACGBNNND<u>CGCT</u>GCARCTAGAATATAAGCAGGCAGGA | DYS456_F4_T |
| SEQ ID NO: 423 | tacacgacgctcttccgatctTACGBNNND<u>CGCT</u>GCAGTCTCATTTCCTGGAGATGAAGG | DYS576_F2_T |
| SEQ ID NO: 424 | tacacgacgctcttccgatctTACGBNNND<u>CGCT</u>CCCTGGGCTCTGTAAAGAA | AmelPP_F_T |
| SEQ ID NO: 425 | cttggcacccgagaattccaACGNNNNH<u>CCGC</u>GGAACACAATTATCCCTGAGTAGCAG | DYS389I_II_R3_Sm |
| SEQ ID NO: 426 | cttggcacccgagaattccaACGNNNNH<u>CCGC</u>GGACAGCCTCCATAWCCACATG | D20S482_R2-Sm |
| SEQ ID NO: 427 | cttggcacccgagaattccaACGNNNNH<u>CCGC</u>GCATCCRTGACTCTCTGGAC | D13S317_R2_Sm |
| SEQ ID NO: 428 | tacacgacgctcttccgatctTACGBNNND<u>CGCC</u>TGAAACTAAAGTCAAATGGGCTAC | DXS10135_F |

Briefly, optimizing primer pools can be an iterative process, for example as shown in the flowchart in FIG. 4. A commercially available primer design software such as Primer3 can be used to design candidate primers for each example that form primer dimers, could be either replaced with other primer candidates or they could be modified with additional sequences that might reduce primer dimer formation; for example by incorporating the QCS and/or ES sequences described herein. The new designs could be retested, assayed for primer dimer formation, redesigned if needed, reassayed, etc. until a group of primers with optimized characteristics is finished.

In some embodiments, an oligonucleotide composition provided herein is assembled in a parallel process. In a parallel process, different pools of primers can be tested in parallel for the ability of each primer in each pool to amplify a target polynucleotide of interest from a sample. The primers in the different pools can be designed to amplify the same plurality of target polynucleotides of interest, or overlapping pluralities of target polynucleotides of interest. For any given target polynucleotide, the primers designed to amplify the target polynucleotide can differ in different pools, e.g., with respect to their TS, QCS, or the presence or absence of an ES. For example, a primer for target polynucleotide A (P(A)) can include a QCS1 in a first pool (P(A)-TS-QCS1), a QCS2 in a second pool (P(A)-TS-QCS2), and an ES in a third pool (P(A)-TS-QCS1-ES). Each primer pool can include a plurality of primers for some or all target polynucleotides of interest, wherein each primer includes a TS, a QCS, optionally an ES, wherein the plurality of primers include two or more QCSs of QCS1, QCS2, QCS3, QCS4, QCS5, QCS6, QCS7 and QCS8. An optimized primer pool can, e.g., be selected from among the different pools of primers tested in parallel, e.g., as the primer pool amplifying the largest fraction of target polynucleotides of interest. Alternatively, after an initial round of testing, some or all of the primer pools tested in parallel can be further optimized, e.g., using an iterative process described herein. In some embodiments, an optimized primer pool can be produced by combining primers from different pools capable of amplifying a target polynucleotide from a sample.

Figure 5:
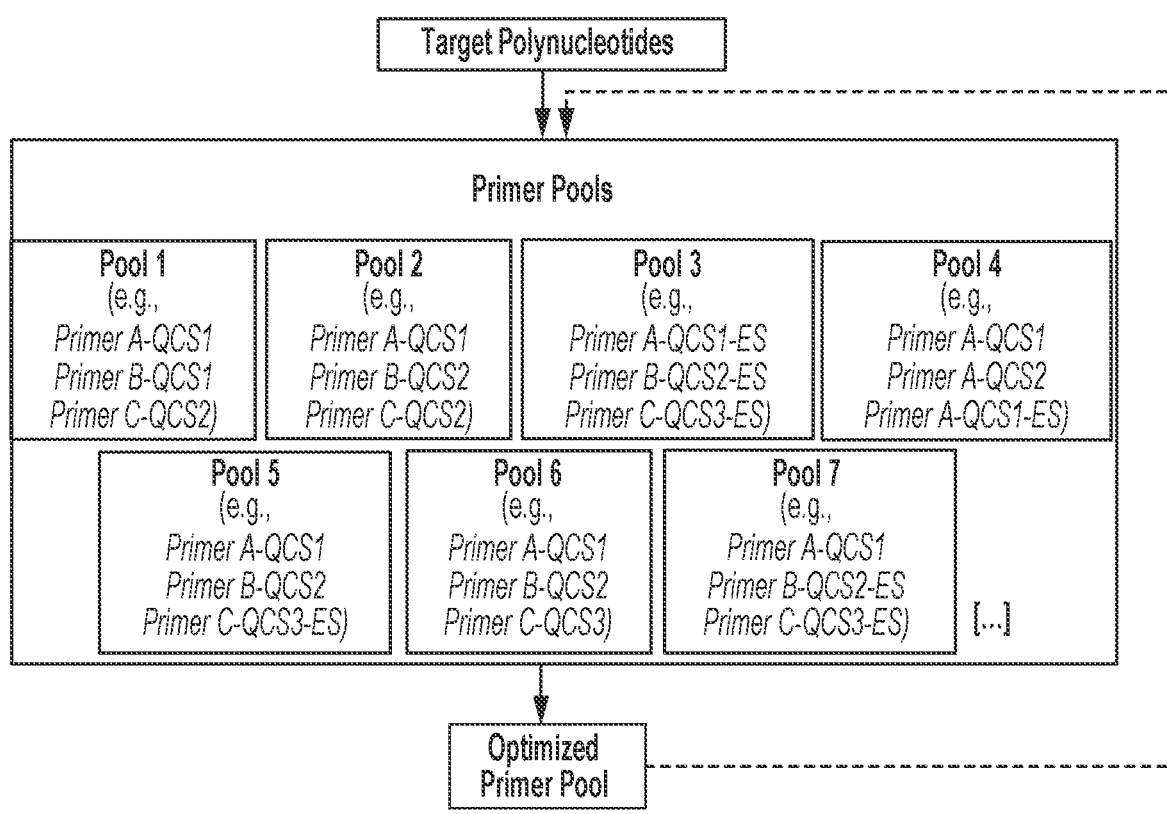
FIG. 5 shows a flow chart illustrating an exemplary parallel process for assembling an oligonucleotide composition provided herein.

An exemplary parallel process for assembling the compositions provided herein is illustrated in FIG. 5.

In some embodiments, the methods provided herein can include producing a sequencing library from target polynucleotides amplified from a sample using an optimized primer pool, or an oligonucleotide composition provided herein.

The exemplary embodiments described herein provide detail for illustrative purposes and are subject to many variations in structure and design. It should be emphasized, however, that the present invention is not limited to a particularly disclosed embodiment shown or described. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting. The terms "a," "an," and "the" herein do not denote a limitation of quantity, but rather denote the presence of at least one of the referenced object. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Furthermore, as will be appreciated by one skilled in the art, aspects of the present disclosure may be embodied as a system, method, or computer program product. Accordingly, aspects of the present invention may take the form of an entirely hardware embodiment or an embodiment combining software and hardware aspects that may all generally be referred to herein as a "circuit," "module" or "system." In addition, aspects of the present disclosure may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM) or similar DVD-ROM and BD-ROM, an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

At least some of the present disclosure is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1

QCS-ES Modified Primers Reduce Dimers

A plurality of primers which formed primer dimers when QCS sequences only were incorporated were subjected to further incorporation of an ES sequence. The primers forming a set of seven primer dimers as follows were redesigned using ES sequences.

| ES Implemented Primer | Primer Dimer Formation Resolved |
|---|---|
| DYS392_F4_T | DYS392-fwd: rs2831700-rev |
| D16S539_F2_T | |
| D61043_F1_T | |
| DYS570_F1_T | |
| D19S433-rev | DYS576-fwd: D19S433-rev |
| PentaD_F3_T | Any primer: DXS10074-rev |
| DYS456_F4_T | |
| DYS576_F2_T | |
| AmelPP_F_T | Amelogenin-fwd: rs1805009-rev |
| DYS389I_II_R3_Sm | rs10776839-fwd: any |
| D20S482_R2_Sm | |
| D13S317_R2_Sm | rs1042602-fwd: D13S317-rev |
| DXS10135-F | Any primer: rs1058083-rev |

FIG. 6A shows primer dimer formation when a QCS labeled forward Amelogenin primer and rs1805009 reverse primer were used in a PCR reaction. FIG. 6B shows that the implementation of ES sequence on forward Amelogenin primer prevented the dimer formation with rs1805009 reverse primer when used in a PCR reaction.

Three primer mixes were created: 1) core primer mix (unaffected by dimerization), 2) core primer mix plus the primers affected by dimerization in their QCS form and 3) core primer set plus the primers affected by dimerization in their QCS+ES form. The final primer concentration in each primer mix consisted of 4 nM of each STR primer and 1 nM of each SNP primer.

One ng of control DNA 2800M was used in a 15 µl PCR reaction containing PCR1 buffer and FEM Enzyme Mix from the FORENSEQ DNA Signature Prep kit (Illumina), as well as the appropriate primer mix. PCR amplification was performed as follows: 98° C. for 3 min, 3 cycles of 98° C. for 2 min, 54° C. for 12 min (with a 0.2° C./s ramp down), 72° C. for 4 min and a final hold at 10° C. Upon completion of thermocycling, 6 µl of primer removal reagent (5 µl of Single-Stranded Binding protein (SSB, 2 µg/µl, Epicenter, E0160-2), 0.67 µl of RecJ (30 U/µl, NEB, M0264L) and 0.33 µl of storage solution (50 mM Tris-HCl, pH 7.5, 100 mM NaCl, 50% glycerol and water) was added to the 15 µl PCR reaction. After thorough mixing by pipetting samples were incubated at 37° C. for 60 min, 95° C. for 10 min, 10° C. for 5 min and a final hold at 10° C.

A second round of PCR reactions was prepared by adding 26 µl of PCR2 Reaction Mix followed by 2 µl of each index primers (FORENSEQ DNA Signature Prep Kit, Illumina) to a PCR reaction tube. PCR amplification was performed as follows: 95° C. for 3 min, 34 cycles of 95° C. for 30 s, 66° C. for 30 s and 72° C. for 1 min, then 72° C. for 5 min and a final hold at 10° C. Sequencing libraries were purified as per manufacturer's instructions in the FORENSEQ DNA Signature Prep guide, with the exception of the first incubation at room temperature being performed for 8 min (instead of 5 min).

The quality and yield of each library was assessed by running the libraries on the FRAGMENT ANALYZER Automated CE System (Advanced Analytical) using High Sensitivity NGS Fragment Analysis Kit as per the manufacturer's recommendation. Libraries were normalized to 1.33 nM each, based on yields obtained by a smear analysis between 5 and 1000 bp. Libraries were pooled and sequenced on a MiSeq instrument (Illumina) according to manufacturer's recommended protocol, using a 351×51 bp run.

Figure 7:
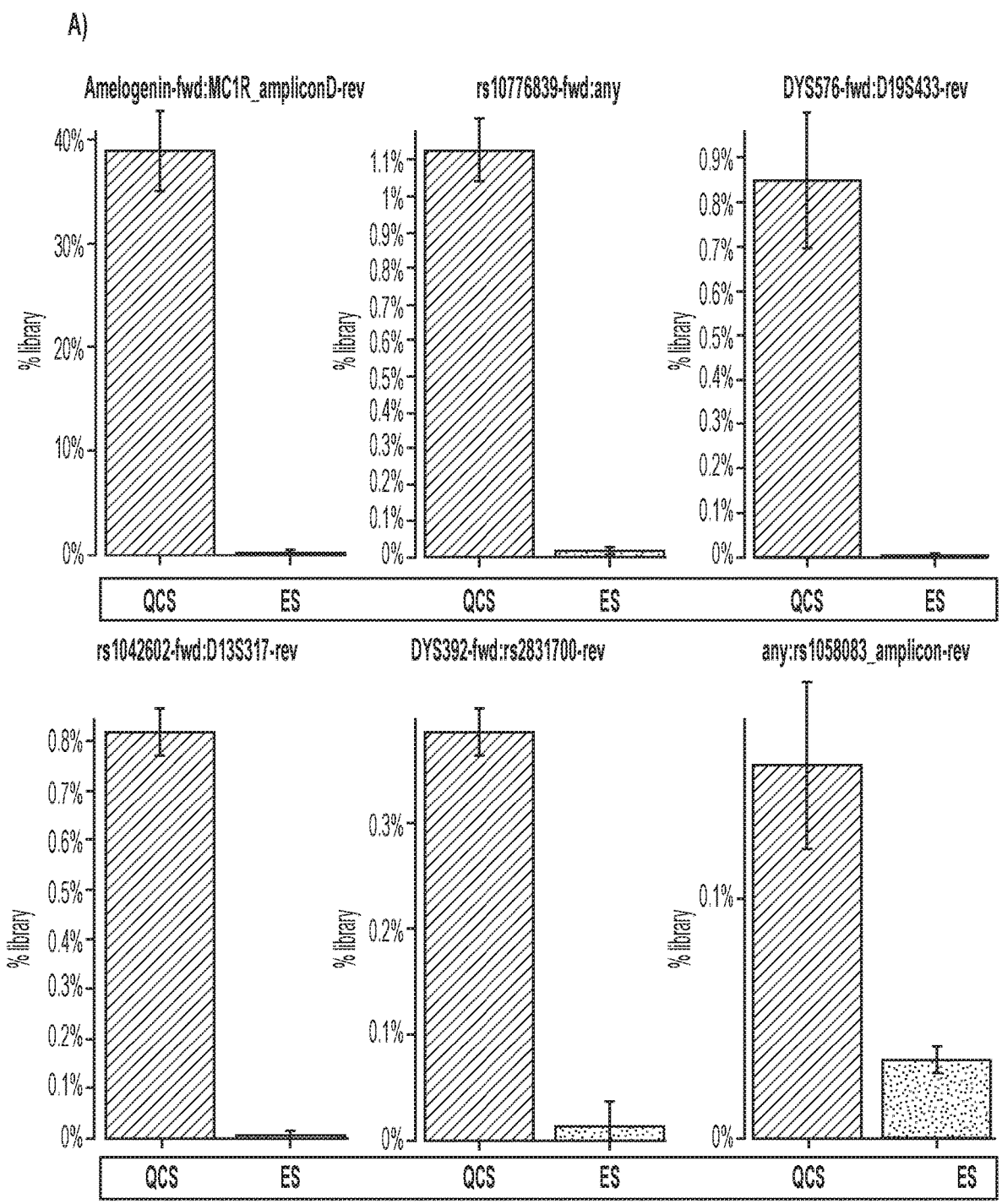
FIG. 7 shows the relative percentage of a library preparation (Y axis) that is primer dimers as a result of A) one or more random QCS containing primers (left column) and primers with QCS sequences and extension sequences (right column), and B) the percent of library that results in aligned sequence reads (Y axis) when only QCS sequences are used to disrupt primer dimers (left column) vs. QCS sequences in addition to extension sequences (right column).
Figure 7:
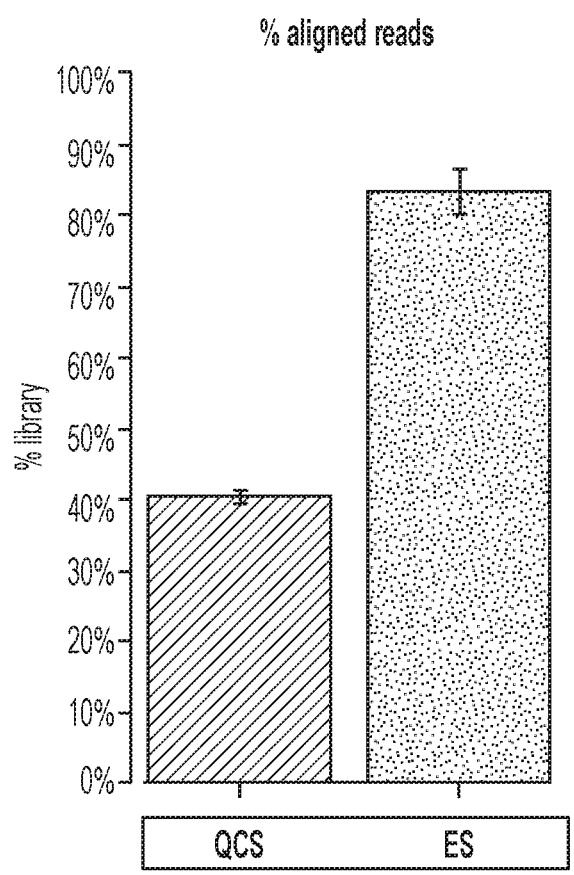

FIG. 7A shows the percentage of sequencing libraries showing primer-dimers when QCS primers were used (left column) as compared to the QCS+ES primers were used (right column) for 6 known primer dimer complexes. Primer dimers were calculated by the number of reads assigned to that dimer over the total number of reads in the library (expressed in on the y-axis). The primer dimer formations resolved were for the primers DYS392-fwd: rs2831700-rev, DYS576-fwd:D19S433-rev, any primer:DXS10074-rev, Amelogenin-fwd:rs1805009-rev, rs10776839-fwd:any primer, rs1042602-fwd:D13S317-rev and any:rs1058083-rev. Addition of ES sequences resulted in reduction of primer-dimerization.

FIG. 7B shows the percentage of aligned reads when QCS primers were used (left column) as compared to the QCS+ES primers were used (right column). Read alignment was calculated as the number of reads aligned to the reference over the total number of reads in the library. As the number of primer dimers decreases through the use of ES, read alignment increases.

Example 2

QCS-ES Modified Primers Reduce Primer Dimers at Low Concentrations of Input Template Primer-dimer formation can be an issue even at relatively low primer concentrations. To demonstrate that the QSC+ES primers reduces primer dimers even at low input template concentration, the experiment of Example 1 was repeated using 100 pg of control DNA 2800M.

Figure 8:
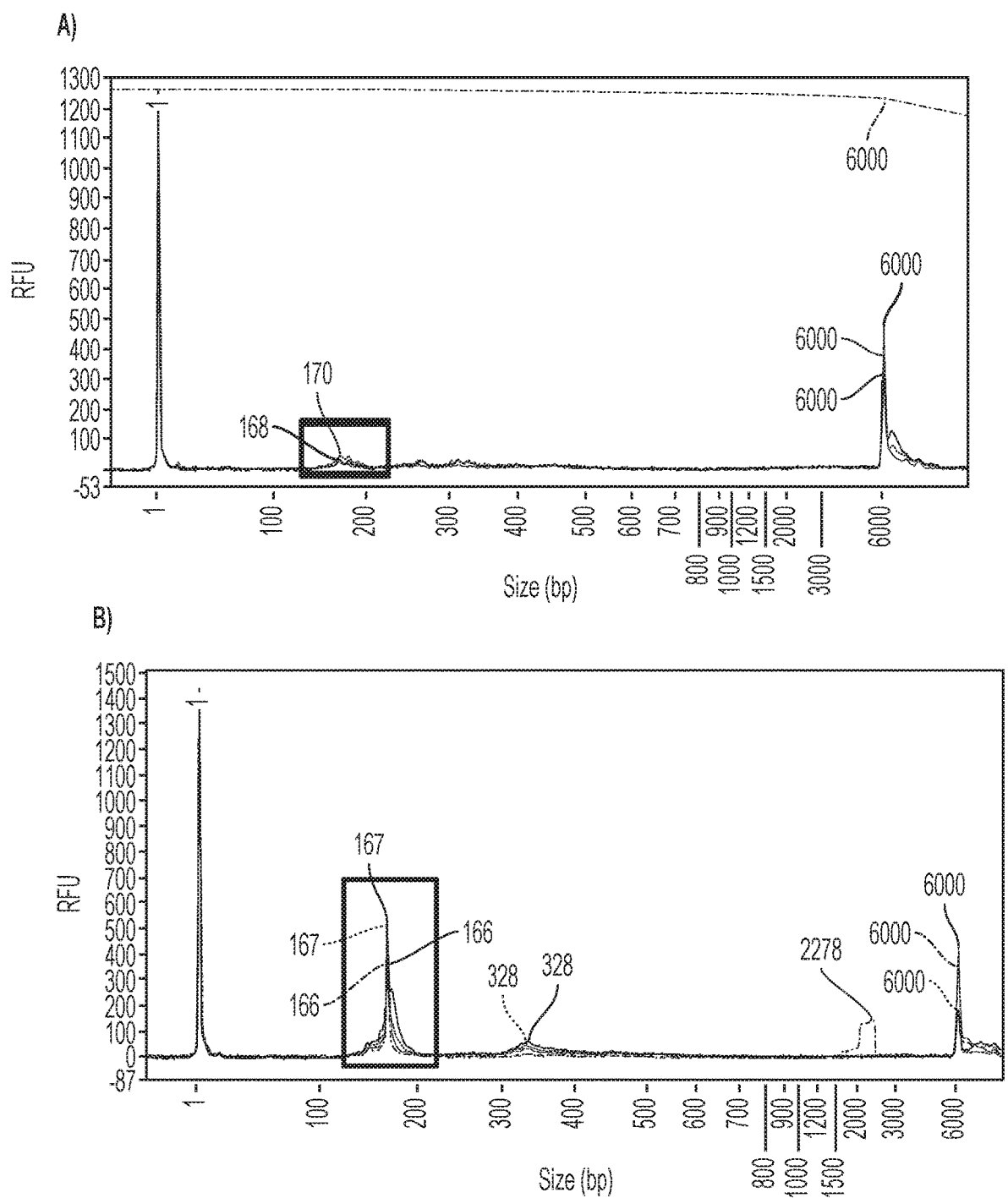
FIG. 8 shows the capillary electrophoresis traces for libraries prepared using low input DNA.
Figure 8:
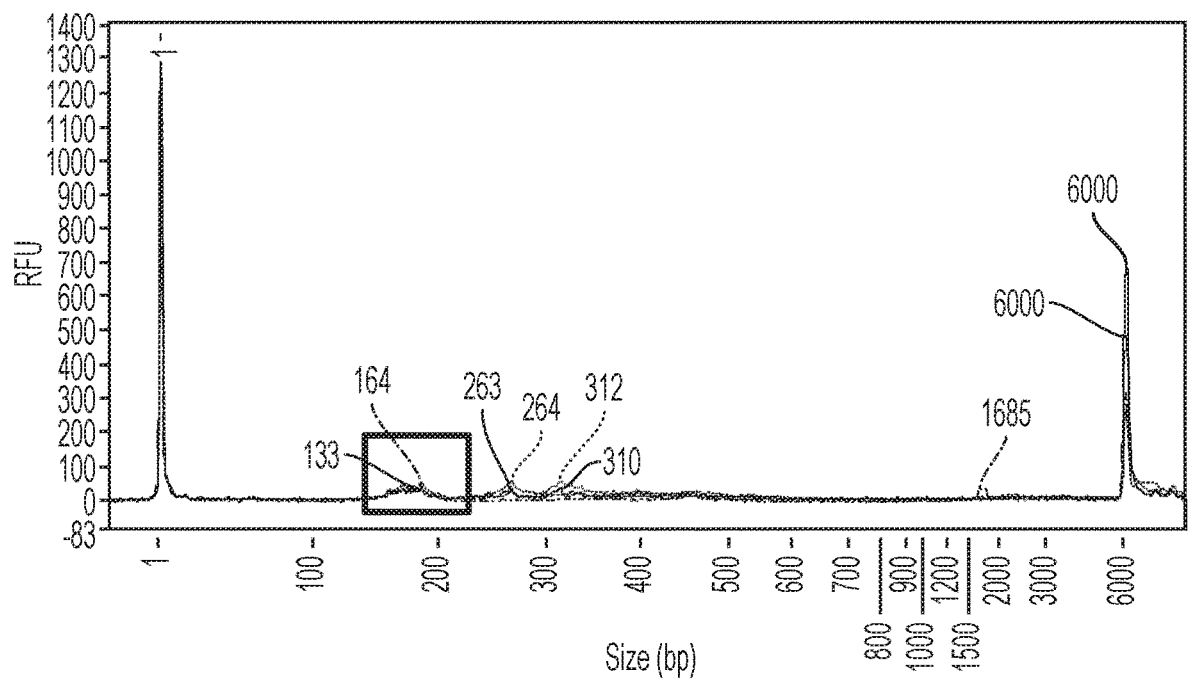

FIG. 8 shows FRAGMENT ANALYZER Automated CE System (Advanced Analytical) traces of libraries prepared using the three primer mixes described for Example 1 and 100 pg of input DNA. FIG. 8A shows an exemplary Fragmant Analyzer trace for the core primer mix, no known primer dimers seen as evidenced by no demonstrable peaks in the black box. FIG. 8B shows the FRAGMENT ANALYZER Automated CE System (Advanced Analytical) trace for the core primer mix plus the primers affected by dimerization in their QCS form showing significant dimers as evidenced by the numerous peaks in the black box. FIG. 8C shows the FRAGMENT ANALYZER Automated CE System (Advanced Analytical) trace for the core primer mix plus the primers affected by dimerization in their QCS+ES form. There are little to no primer dimer peaks visible in the black box when the QCS+ES primer mix is used with the core primers, in contrast to what is seen in FIG. 8B.

Example 3

QCS-ES Modified Primers Reduce Dimers at Reduced Primer Concentrations

Primer-dimer formation could be more pronounced when the primer concentration is limited. To demonstrate that the QSC+ES primers reduce primer dimers even at low primer concentration, the experiment of Example 1 was repeated using reduced primers and 1 ng of control DNA 2800M. The final primer concentration in each primer mix consist of 2 nM for each STR primer and 0.5 nM for each SNP primer.

Figure 9:
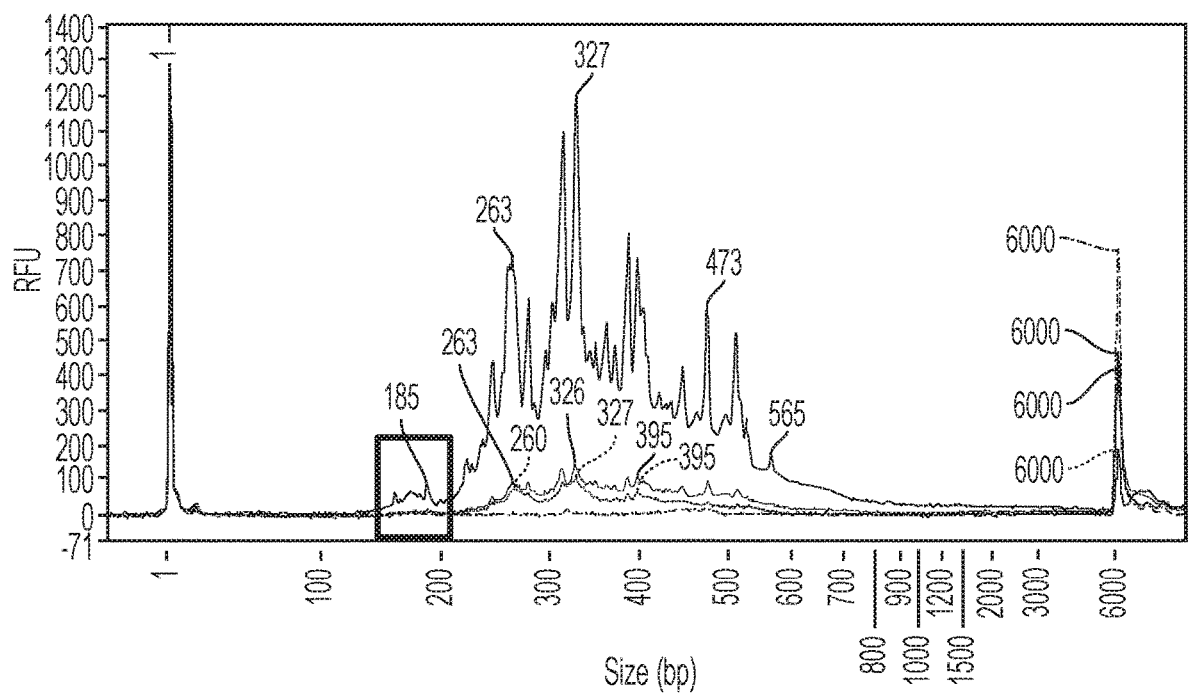
FIG. 9 shows the capillary electrophoresis traces for libraries prepared using low primer concentrations.

FIG. 9 shows exemplary FRAGMENT ANALYZER Automated CE System (Advanced Analytical) traces of libraries prepared using the three primer mixes described for Example 1 with the exception that each primer mix consists of 2 nM of each STR primer and 0.5 nM of each SNP primer and 1 ng input DNA. FIG. 9A shows a FRAGMENT ANALYZER Automated CE System (Advanced Analytical) trace for the core primer mix with no demonstrable primer dimers in the black box. FIG. 9B shows a FRAGMENT ANALYZER Automated CE System (Advanced Analytical) trace for the core primer mix plus the primers affected by dimerization in their QCS form showing significant amounts of primer dimers in the black box. FIG. 9C shows a FRAGMENT ANALYZER Automated CE System (Advanced Analytical) trace for the core primer mix plus the primers affected by dimerization in their QCS+ES form. There are minimal to no primer dimer peaks in the black box when the QSC+ES primer mix is used with the core primers as compared to FIG. 9B.

Example 4

Design of gSpacer and aSpacer

Figure 10:
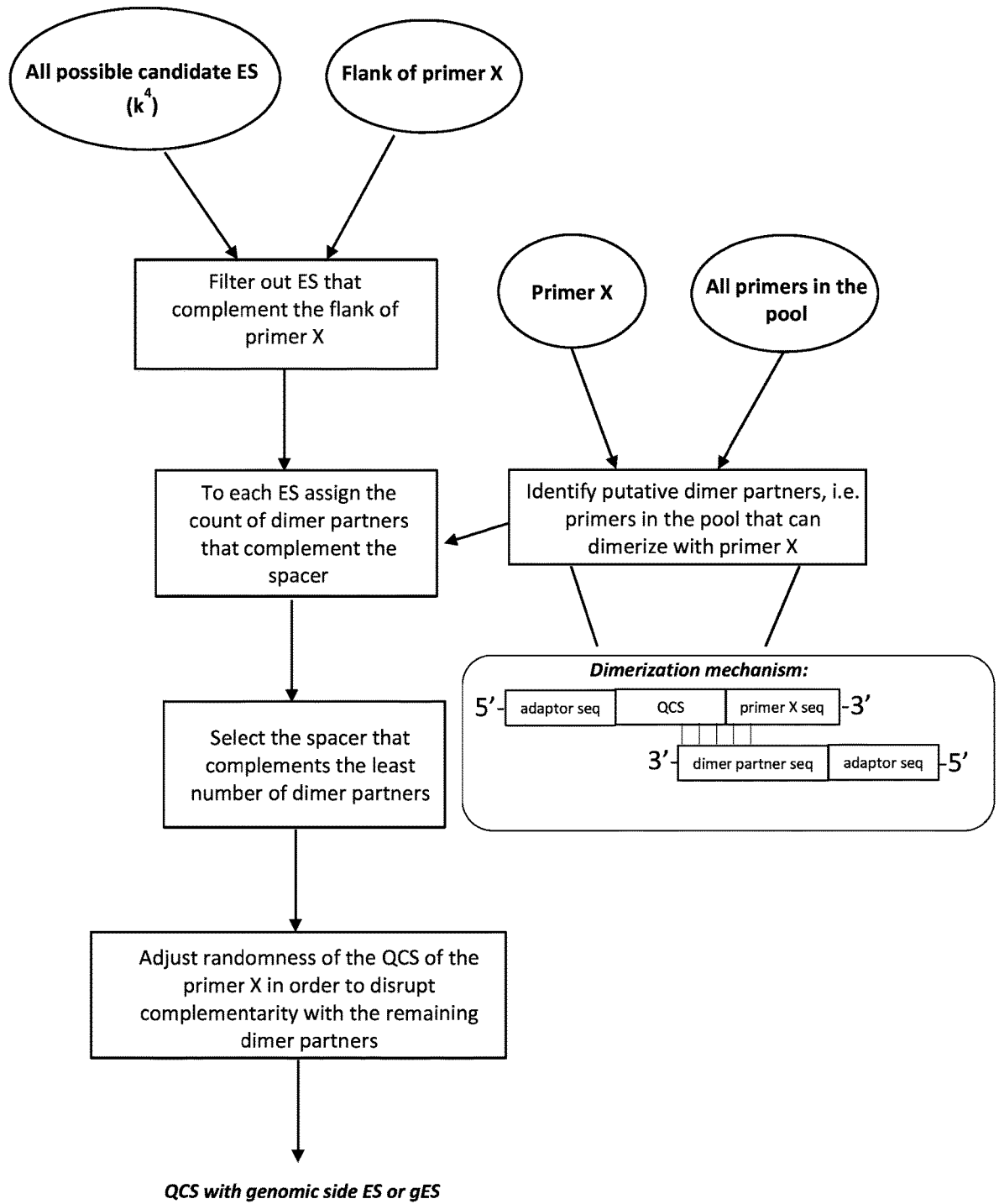
FIG. 10 demonstrates an exemplary decision tree on how to determine when an extension sequence or ES should be included in any primer sequence on the genomic sequence side of the primer (gES).

FIG. 10 shows an exemplary flow diagram for designing a gSpacer (the ES on the TS side of a QCS). To design an effective gSpacer for a primer of interest in a pool of primers (referred to as primer X in FIG. 10), possible stable interactions between the TS sequence of primer X, its QCS, and sequences of other primers in the pool that are conducive to forming primer-dimers are predicted. The gSpacer should disrupt all such stable interactions between primer X, its QCS and other primers in the pool. The gSpacer should not extend the complementarity of the TS sequence of primer X to its intended annealing site and alter the annealing temperature of primer X. In addition, the gSpacer should not in itself provide a sequence that, together with the QCS of primer X, results in new stable interactions with other primers in the pool.

First, the sequences of primers predicted to form a stable interaction with the TS sequence of primer X and its QCS are examined and those k-mers (all possible oligomers of length k, where k is the intended length of a gSpacer, for example, 4 nucleotides) that do not disrupt such interactions are excluded. Next, the sequence of the genomic flank upstream of the primer X annealing site are examined and any k-mers that extend complementarity of primer X to its annealing site are excluded. The gSpacers that passed the selection of the first two steps of the procedure are ranked according to; (A) their similarity to sequences of primers in the pool capable of forming a stable interaction with primer X; and (B) the number of primers in the pool that complement the gSpacer in question and form a novel dimer. In some embodiments, the randomness of the QCS of primer X is reduced to disrupt interactions conducive to forming new primer-dimers.

Figure 12:
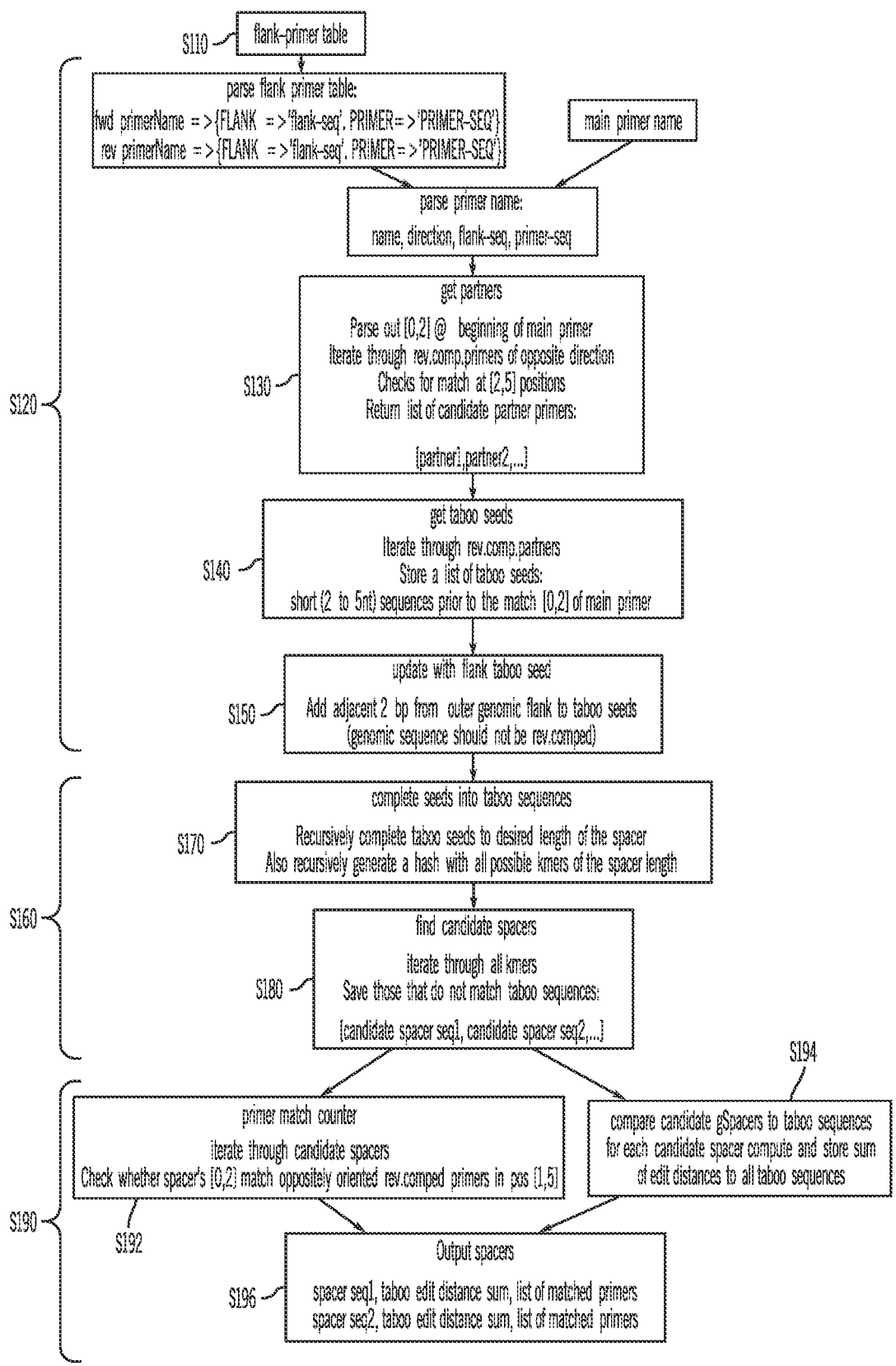
FIG. 12 shows an exemplary flow diagram of determining an extension sequence, according to embodiments of the invention.

A flow diagram in FIG. 12 shows steps of embodiments of the invention. In step S110, primer sequences can be received. In step S120, taboo seeds are determined from the primer sequences. This includes step 130 determining putative dimer partners. At this step we are looking for primers with orientation opposite to the main primer and also with sequences that can potentially allow formation of sequencable dimers with our main primer. In some embodiments, the main primer is a primer that forms UMI-mediated dimers at an unacceptably high level, so that there is a need to modify the primer by adding spacers in order to reduce abundance of the dimers. Currently to identify partners the three first bases of the main primer (i.e. bases adjacent to UMI of the main primer), called anchor sequences. Primers in the opposite orientation are looked for that have a perfect anchor match. Ordinarily during dimer formation complementarity to bases after the anchor match (called anchor overhang sequence) is provided by the UMI of the main primer (see illustrations below). If anchor match and anchor overhang form a complementarity region of 5 bases or longer (but not extending beyond UMI) then such primer pairs can be considered to be putative dimer partners. For example, these are some of putative partners of DXS10074-rev main primer (SEQ ID NOS 429-436 disclosed below, respectively, in order of appearance):

```
DYS448-fwd      5'-AATAGAGATCGCGAGACAGAAAGG
                                    |||||
                AGACTCCCCGTGACTCTGGTATTTNNNNN-5' DXS10074-rev rs12821256-fwd  5'-TGTGTGGCAGAAGTTGAAAATTA
                                   ||||||
                AGACTCCCCGTGACTCTGGTATTTNNNNN-5' DXS10074-rev
```

-continued

```
RS1498553-fwd    5'-ATAAATCAGACCAGGATGAAAGTTC
                                    |||||||
                 AGACTCCCCGTGACTCTGGTATTTNNNNNN-5' DXS10074-rev RS3780962-fwd    5'-AATAATCCTCAAAAACAAAGAAACATGG
                                    ||||||||
                 AGACTCCCCGTGACTCTGGTATTTNNNNNN-5' DXS10074-rev
```

On the other hand, these primers are currently not considered to be putative partners of DXS10074-rev (SEQ ID NOS 437-440 disclosed below, respectively, in order of appearance):

```
DYS505-fwd       5'-TCTGGCGAAGTAACCCAAAC
                                    ||||
                 AGACTCCCCGTGACTCTGGTATTTNNNNNN-5' DXS10074-rev RS1800414-fwd    5'-AAAACATGAAGATAACAAATCCCAA
                                    ||||||||
                 AGACTCCCCGTGACTCTGGTATTTNNNNNN-5' DXS10074-rev
```

Here annealing with DYS505-fwd forms a complementarity stretch of less than 5 bases, so we do not consider such interaction to be dangerous and/or solvable with the gSpacer approach (also see Restrictions on minimum taboo seed length). While complementarity with RS1800414-fwd is longer than 5 bases, it is not actually completed at the 3'-end, so we also do not consider this to be dangerous and/or solvable with gSpacer. (Note that if the 3'-end of the anchor overhang would actually complement the adaptor part of DXS10074-rev primer, then such interaction is going to be addressing by aSpacer, see below).

Step S120 can include step S140 of determining taboo seeds from the putative dimer partner determination. Predicting putative dimer partners allows us to compile a list of taboo seeds—the sub-sequences that turn kmers to be inappropriate as spacers. For example, looking at DYS448-fwd: DXS10074-rev putative dimer (see illustration above) we can see that gSpacers of DXS10074-rev should not end with CC, because such spacers would not prevent formation of 5 nt perfect complementarity region with DYS448-fwd (that ends with AAAGG). Therefore, CC subsequence is a taboo seed, and kmers ending with CC are taboo sequences that should be excluded from gSpacer space. As another example, looking at rs12821256-fwd:DYS10074-rev putative dimer we can see that gSpacers should not end with TAA, as attaching such spacer to DXS10074-rev would create a 6 nt complementarity stretch with rs12821256-fwd (that ends with AAATTA). So TAA is also added to the list of taboo seeds. Restrictions on minimum taboo seed length: In principle we could have had 1 nt taboo seeds, as disrupting complementarity with the ending of the gSpacer could be sufficient to reduce dimer formation. From the two examples above (DYS448-fwd:DXS10074-rev and rs12821256-fwd:DXS10074-rev), 'C' and 'A' could be 1 nt taboo seeds. This however would exclude half of all possible gSpacers as any kmer ending with 'C' or 'A' would be considered a taboo sequence. So with 1 nt taboo seeds we very quickly loose gSpacer space and end up with no spacers at all. This is a part of the reason why DYS505-fwd: DXS10074-rev type of interactions are not practically solvable with gSpacer approach.

Next, step S120 can include step S150 of adding to the list of taboo seeds a sequence based on the genomic flank of the main primer. For example, an adjacent 2 base pairs from the outer genomic flank can be added to taboo seeds. We do not want gSpacer to extend complementarity of gene specific portion of the primer to genomic DNA. Therefore spacers should not include sequence of the genomic flank of the main primer, ideally not even partially. The current approach is to consider a two-nucleotide sequence of genomic flank immediately adjacent to the primer to be a taboo seed. Therefore currently all kmers ending with 2 nt of genomic flank are excluded from gSpacer space.

Step S160 includes making a list of candidate gSpacers. This can include step S170 completing taboo seeds into taboo sequences. The taboo seed can be as short as 2 bases and the gSpacer length can be as long as desired. In order to facilitate the procedure of filtering out taboo seed containing kmers from gSpacer space (next step) we first complete seeds into sequences that are of the same length as gSpacers that we want to design. For example, if we want to design a four-nt long gSpacer, a 3 nt taboo seed GGG would be completed into AGGG, TGGG, CGGG and GGGG taboo sequences.

The taboo seed can also have a length as short as 1 base, although in practice, with Forensics primer pool, kmer space could quickly run out if the kmers were filtered based on a match to 1 nt taboo seeds. Setting taboo seed of length to 2nt is a practical decision for relatively large multiplex PCR primer pools, but if one deals with a very small primer pool with a handful of primers, then they can consider setting minimum taboo seed length to 1 base.

Step S160 can include step S180 determining gSpacer candidates from the gSpacer space. For example, in some embodiments, after obtaining a list of kmers that contain taboo seeds, a gSpacer space (i.e. all possible kmers of length 4 nt) can be generated and can be reduced to candidate gSpacers by removing kmers that contained the seeds.

In steps described above, candidate gSpacers can be ensured to match neither putative dimer partners nor the genomic flank of the main partner. The addition of a gSpacer can create an opportunity of forming dimers with those primers that happen to match the gSpacer sequence itself. Thus, step S190 includes screening for the candidate gSpacers that minimize the likelihood of such interactions from taking place.

In step S192, the new interactions are counted with candidate gSpacers and primers in the primer pool. While step S194 is helpful in choosing the best candidate spacers through a different mechanism. By this point the fact that none of the candidate gSpacers match any of taboo sequences (this can be done during step S180) can be verified, such that step S194 can include choosing a spacer that not only does not match taboo sequences precisely, but as far as possible removed (using edit distance as a metric) from taboo sequences.

In step S192, a primer match counter can be used to count how many oppositely oriented primers match our candidate spacer. Additionally or alternatively, candidate gSpacers can be ranked by the number of primers of the opposite orientation that match its sequence (the smaller number of primers matched—the better). This computation can include tallying counts of primers with orientation opposite to the main primer that have a 3 nucleotide match to the 5' end (i.e., the left end of gSpacer, which can be the same as "the first three bases of gSpacer") of the gSpacer within 8 last nucleotides of these primer's (i.e., at their 3' ends, the same as right ends). A user can select from the list of ranked spacers a spacer that allows for the smallest number of such novel gSpacer-mediated dimers (it will be printed at the top of the list) and then manually adjust randomness in the UMI to allow these predicted dimers. Currently a complementarity to the first three bases of the spacer is required for a primer to be considered a match to gSpacer. The range can be [1,5] that can be checked for possible novel dimer-producing interactions between the candidate spacers and primers with opposite orientation in the pool. In cases of closed ranges (such as here, numbers enclosed in [ ]), it can denote a range where both the start and the end of the range are inclusive, i.e. they are in 0-based counting. In this example, [1,5] can mean that we are looking for the gSpacer anchor matches (the gSpacer anchor is 3nt long) starting anywhere from the 2nd last nucleotide of the possible dimer partner sequence through starting at the 6th last nucleotide (i.e., match starting at the 6th nucleotide means that, the nucleotides 6th, 7th, and 8th last nucleotides of the primer dimer partner complement the gSpacer anchor).

Step S192 can include checking whether a spacer's [0,2] match oppositely oriented reverse complementary primers beginning in position [1,5]. The addition of gSpacer serves as the gSpacer anchor sequence, which can means three first nucleotides of a gSpacer, i.e. the nucleotides in the range [0,2], which is adjacent to the UMI sequence. That is, for the gSpacer anchor, range [0,2] can mean that the gSpacer anchor comprises 1st, 2nd and 3rd first nucleotides of the main primer (i.e. it's 5' or left end). A range referring to spans checking for anchor matches can mean checking for the beginning of the match. So checking for a match in [2,5] range means that the match can begin at the 3rd nucleotide, and in such case 3rd, 4th and 5th last nucleotides of the dimer partner primer (i.e it's 3' or right end) complement the gSpacer anchor sequence. And the match can begin as far as in the 6th nucleotide, and in such case 6th, 7th, and 8th last nucleotides of the dimer partner would complement the anchor sequence.

The gSpacers can be computed in step S194 by the sum of distances (edit distance) between its sequence and taboo sequences (the bigger distance—the better). This distance can be an alignment metric for measuring the difference between two sequences, such as a Levenshtein distance. Both steps S192 and S194 can compute metrics that allow for a subsequent ranking of spacers during following step described here. Step S190 can include step S196 outputting the results of the candidate gSpacers. In an embodiment, top 20 candidate gSpacers (using either metric) can be printed to standard output together with such metrics as the number of primers matched (i.e. potential new dimer partners) and the sum of distances between gSpacer length and taboo sequences. The very last line of the output can contain the best candidate gSpacer (as judged by the least number primers matched and the biggest distance from taboo sequences).

Figure 11:
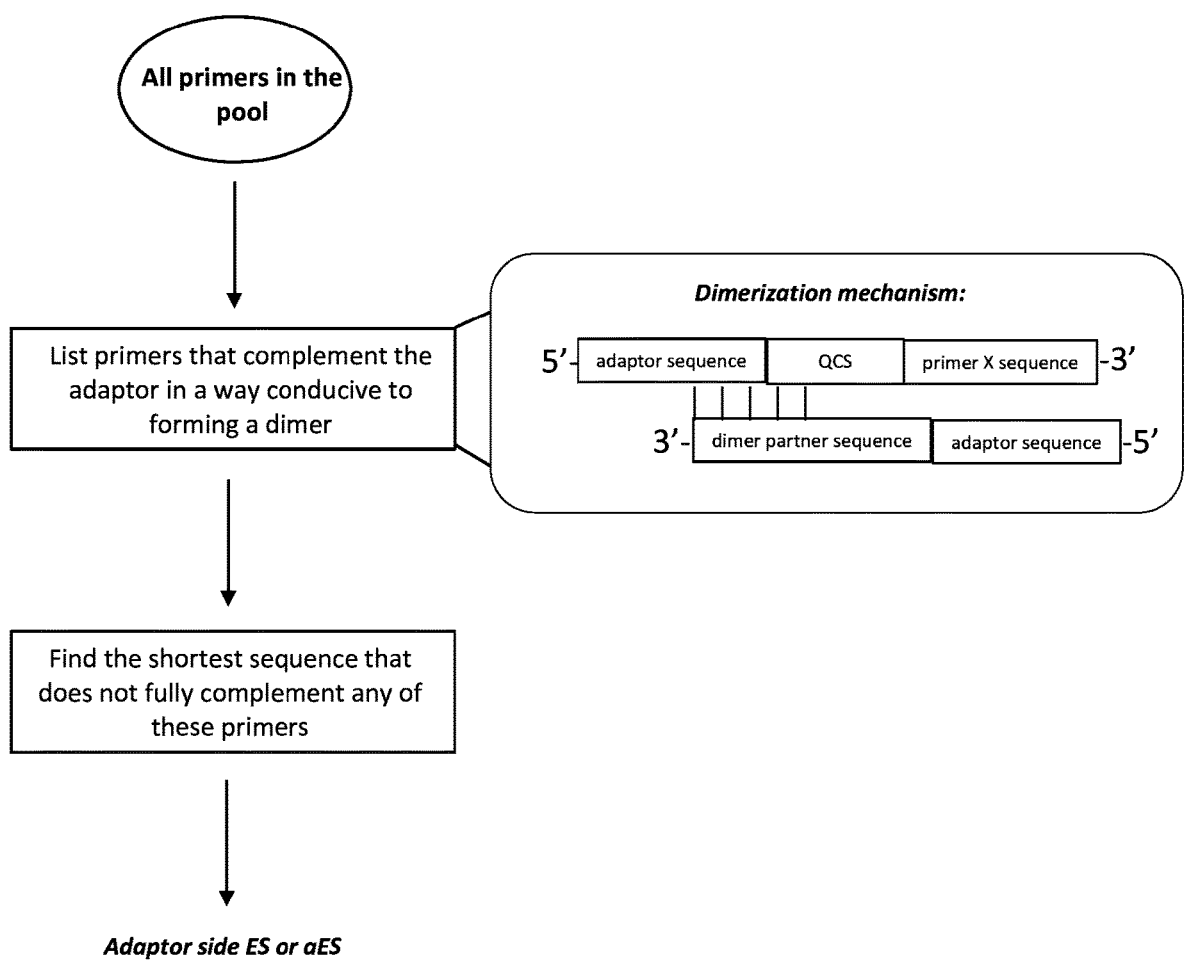
FIG. 11 demonstrates an exemplary decision tree on how to determine when an extension sequence or ES should be included in any primer sequence on the adaptor sequence side of the primer (aES).

FIG. 11 shows an exemplary flow diagram for designing an aSpacer (the ES on the adaptor side of a QCS). The type of a primer-dimer disrupted by an aSpacer is shown on the inset pane. For this type of a primer-dimer, a primer Y has a complementarity at its 3'-end to the adaptor sequence of a primer X. Since a primer X contains a QCS, complementarity of the primer Y and the adaptor can be extended by the QCS. In some instances, TS primer designs can have short substrings (e.g. 1-3 nt) at their 3'-end that complement the adaptor of primer X. In such cases, a fully randomized QCS of a primer X can extend this complementarity and lead to a stable interaction between primers Y and X, potentially resulting in a primer-dimer during PCR. In order to design an aSpacer for primer X, a sequence that does not fully complement any primer in the pool that has a complementarity at its 3'-end to the adaptor sequence of primer X is chosen. In other embodiments, an aSpacer can be chosen to disrupt interaction between the adaptor of a primer X, its QCS and a single selected primer or several selected primers from the pool of primers.

Some gene specific primer sequences have one or more base complementarity to the ending of an adaptor sequence, for example an Illumina adapter sequence. The UMI sequence can extend this complementarity, as UMIs are adjacent to the adaptor sequence in UMI primers. aSpacers are meant to disrupt UMI mediated adaptor complementarity extension (SEQ ID NOS 441-444 disclosed below, respectively, in order of appearance).

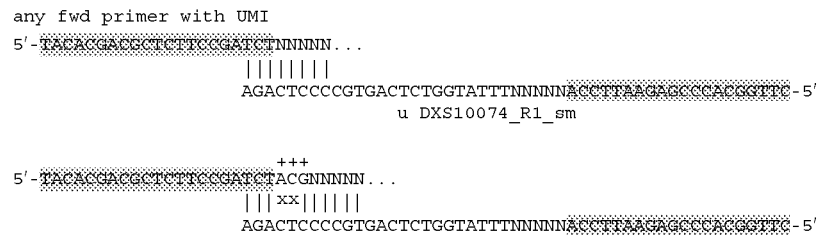

The diagram above shows how incorporation of ACG aSpacer disrupts formation of dimers with DXS10074-rev. Adaptors for forward and reverse primers are highlighted in purple and yellow, respectively. The UMI sequence is highlighted with yellow and aSpacer sequence is marked with '+' characters.

Incorporating not-so-randomness into UMI of SUMIs

Spacer sequences are chosen in such a way that they match as few primers in the multiplex as possible. But it may not be possible to find a spacer that doesn't complement any of the primers in the mix. For example, CGCG sequence is very rare in the genome and can be a good spacer. Yet, the first three bases of such gSpacer anchor would complement PentaE-rev primer sequence and so PentaE-rev primer theoretically can form a dimer with primers carrying CGCG gSpacer. In order to be able to use CGCG spacer and at the same time prevent PentaE-rev primer from forming the dimer, we can reduce randomness of UMI in SUMIs. In the example of PentaE-rev interaction changing last nucleotide in UMI from N to D (which is 'A', "G' or 'T', but not 'C) is going to reduce PentaE-rev dimer with SUMI primers (SEQ ID NOS 445-448 disclosed below, respectively, in order of appearance).

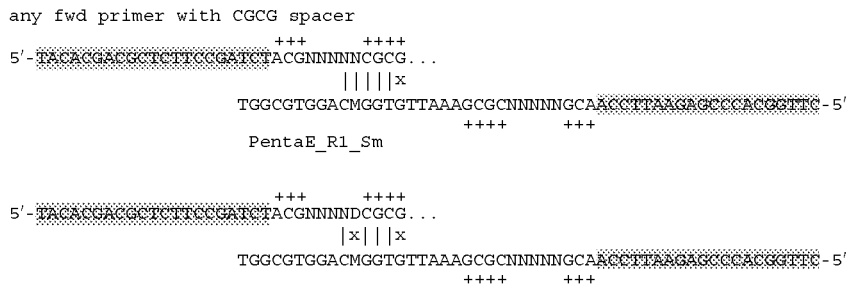

Thus, in some embodiments, in addition to selecting the best-ranked spacers that introduce a level of instability in the interaction between the main primer and putative primer dimer partners, applying a level of not-so-randomness to the molecular tag of the main primer further increases instability of the interaction between the main primer and other primers. If a primer is found that complements the first three nucleotides of the candidate spacer anywhere beginning in the primer's [1,5] last nucleotides (i.e. at it's 3' or right end), then, according to some embodiments, the randomness of the UMI can be adjusted to allow use of such spacer. So the threshold can be a requirement for a perfect match of the Spacer's [0,2] nucleotides within the last eight nucleotides of the primer (in this step, matches that began at the very last nucleotide are less relevant, but being conservative the [0,5] range could be checked for possible interactions, and, conversely, more loose and narrowed checks to just [2,5] range could be checked. Thus, instead of the molecular tag having four possibilities for each of the nucleotides at each of five positions, the molecular tag could be designed to have one or more position with fewer than four possible nucleotides.

Thus, embodiments of the invention can include a computer-implemented method of determining a nucleotide spacer sequence for disrupting primer dimer formation. This method can include receiving a set of primer sequences. The method can also include determining, using at least one microprocessor, a plurality of candidate spacers between an adapter sequence and a gene-specific portion of the primer sequence. The determined plurality of candidate spacers can include sequences that disrupt stable interactions between sequences of the set of primer sequences. The method can include ranking, using at least one microprocessor, candidate spacers that meet a predetermined threshold value of stable interactions in the extension sequences. The method can include outputting a set of the ranked spacers that meet the predetermined threshold.

In the method, the plurality of spacers can be in between a molecular tag portion and one of the adapter sequence and the gene-specific portion of the primer sequence.

In the method, the step of determining spacer sequences can include determining a gene-specific side sequence that flanks a first side of the molecular tag.

The step of determining spacer sequences can also include determining an adapter side sequence that flanks a second side of the molecular tag.

The step of determining the candidate spacers can include determining, using at least one microprocessor, taboo seeds based on sequences that complement the primer; and removing sequences that include the taboo seeds from the candidate spacers. The step of determining the candidate spacers can include updating the taboo seed flank with adjacent base pair sequences from the outer genomic flank.

The step of ranking the list of candidate spacers can be based on alignment edit distances between the candidate spacers and the taboo sequences.

The step of ranking the list of primers can include checking whether a portion of the spacer sequences matches oppositely reversed complimentary primers. The step of ranking can further include designing the molecular tag to be less than completely random depending on the ranking of the set of the ranked spacers.

What is claimed is:

1. An oligonucleotide composition, comprising a plurality of primer pairs, each primer pair comprising a target nucleic acid specific sequence (TS) and wherein the plurality of primer pairs comprises a respective different plurality of TSs such that each primer pair of the plurality of primer pairs comprises a different TS of the respective different plurality of TSs, and wherein each primer pair of the plurality of primer pairs comprises a forward primer and a reverse primer, the forward primer and the reverse primer each comprising a quality control sequence (QCS), wherein the QCS of the forward primer comprises a forward primer QCS and the QCS of the reverse primer comprises a reverse primer QCS selected from the group consisting of
a first QCS (QCS1), wherein each nucleic acid position is fully randomized,
a second QCS (QCS2), wherein one or more nucleic acid positions are partially randomized,
a third QCS (QCS3), wherein one or more nucleic acid positions are fixed,
a fourth QCS (QCS4), wherein all nucleic acid positions are fixed,
a fifth QCS (QCS5), wherein one or more nucleic acid positions are fully randomized and one or more nucleic acid positions are partially randomized,
a sixth QCS (QCS6), wherein one or more nucleic acid positions are fully randomized and one or more nucleic acid positions are fixed,
a seventh QCS (QCS7), wherein one or more nucleic acid positions are partially randomized and one or more nucleic acid positions are fixed, and
an eighth QCS (QCS8), wherein one or more nucleic acid positions are fully randomized, one or more nucleic acid positions are partially randomized, and one or more nucleic acid positions are fixed; and wherein each forward primer and reverse primer of the plurality of primer pairs has a unique QCS relative to each other and to other primer pairs of the plurality and wherein the plurality of primer pairs comprises two or more different QCSs selected from the group consisting of QCS1, QCS2, QCS3, QCS4, QCS5, QCS6, QCS7, and QCS8, wherein the QCS of forward primers of the plurality of primer pairs is flanked by an extension sequence (ES) such that the ES is positioned on both sides of the QCS, wherein the ES comprises a fixed sequence that is a same sequence among the forward primers.

2. The oligonucleotide composition of claim 1, wherein the plurality of primer pairs comprises 3, 4, 5, 6, 7, or 8 QCSs selected from the group consisting of QCS1, QCS2, QCS3, QCS4, QCS5, QCS6, QCS7, and QCS8.

3. The oligonucleotide composition of claim 1, wherein one or more primers comprises an adaptor sequence (AS) on a 5'-end of the QCS.

4. The oligonucleotide composition of claim 3, wherein, for a portion of the forward primers, the ES is between the AS and the QCS (AES) or in between the QCS and the TS (TES).

5. The oligonucleotide composition of claim 1, wherein the ES comprises a sequence of between 2 and 5 bases.

6. The oligonucleotide composition of claim 1, wherein QCS1, QCS2, QCS3, QCS4, QCS5, QCS6, QCS7, or QCS8 comprises a sequence of 3-12 bases.

7. The oligonucleotide composition of claim 1, wherein the plurality of primer pairs comprises between about 4 primers and about 5000 primers.

8. The oligonucleotide composition of claim 7, wherein the plurality of primer pairs comprises between about 4 primers and about 550 primers.

9. The oligonucleotide composition of claim 7, wherein at least one forward primer of the plurality of primer pairs comprises a QCS selected from the group consisting of QCS1, QCS2, QCS3, QCS4, QCS5, QCS6, QCS7, and QCS8, and wherein at least one reverse primer of the plurality of primer pairs comprises a QCS selected from the group consisting of QCS1, QCS2, QCS3, QCS4, QCS5, QCS6, QCS7, and QCS8.

10. The oligonucleotide composition of claim 1, wherein the TS of one or more primers is complementary to a region flanking a short tandem repeat (STR) region.

11. The oligonucleotide composition of claim 1, wherein the plurality of primer pairs comprises one or more primers to amplify short tandem repeats or single nucleotide polymorphisms selected from the group consisting of D16S359, D61043, DYS570, D19S433, PentaD, DYS576, AmelPP, DXS10135, D13S317, DYS389, D20S482, DXS10074, rs1805009, rs10776839, rs2831700, rs1042602, rs1058083, DYS392, D22S1045, DYS19, DYS456, DYS439, and DYS635.

12. The oligonucleotide composition of claim 1, wherein the forward primer QCS and the reverse primer QCS of each primer pair are of a same QCS type such that the forward primer and the reverse primer have a same level of randomness.

13. The oligonucleotide composition of claim 1, wherein, among different forward primers of the plurality of primer pairs, two or more different QCSs selected from the group consisting of QCS1, QCS2, QCS3, QCS4, QCS5, QCS6, QCS7, and QCS8 are present in the oligonucleotide composition, and among different reverse primers of the plurality of primer pairs, two or more different QCSs selected from the group consisting of QCS1, QCS2, QCS3, QCS4, QCS5, QCS6, QCS7, and QCS8 are present in the oligonucleotide composition.

14. The oligonucleotide composition of claim 3, wherein the forward primers of the plurality of primer pairs all have a universal AS, and wherein the QCS is not part of or complementary to the universal AS.

15. The oligonucleotide composition of claim 1, wherein the QCS is positioned within 4-6 nucleotides of the TS.

16. An oligonucleotide composition, comprising a plurality of primer pairs, each primer pair comprising a target nucleic acid specific sequence (TS) and wherein the plurality of primer pairs comprises a respective different plurality of TSs such that each primer pair of the plurality of primer pairs comprises a different TS of the respective different plurality of TSs, and wherein each primer pair of the plurality of primer pairs comprises a forward primer and a reverse primer, the forward primer and the reverse primer each comprising a quality control sequence (QCS), wherein the QCS of the forward primer comprises a forward primer QCS and the QCS of the reverse primer comprises a reverse primer QCS selected from the group consisting of
 a first QCS (QCS1), wherein each nucleic acid position is fully randomized,
 a second QCS (QCS2), wherein one or more nucleic acid positions are partially randomized,
 a third QCS (QCS3), wherein one or more nucleic acid positions are fixed,
 a fourth QCS (QCS4), wherein all nucleic acid positions are fixed,
 a fifth QCS (QCS5), wherein one or more nucleic acid positions are fully randomized and one or more nucleic acid positions are partially randomized,
 a sixth QCS (QCS6), wherein one or more nucleic acid positions are fully randomized and one or more nucleic acid positions are fixed,
 a seventh QCS (QCS7), wherein one or more nucleic acid positions are partially randomized and one or more nucleic acid positions are fixed, and
 an eighth QCS (QCS8), wherein one or more nucleic acid positions are fully randomized, one or more nucleic acid positions are partially randomized, and one or more nucleic acid positions are fixed; and wherein each forward primer and reverse primer of the plurality of primer pairs has a unique QCS relative to each other and to other primer pairs of the plurality and wherein the plurality of primer pairs comprises two or more different QCSs selected from the group consisting of QCS1, QCS2, QCS3, QCS4, QCS5, QCS6, QCS7, and QCS8, wherein the QCS of forward primers of the plurality of primer pairs is flanked by an extension sequence (ES) such that the ES is positioned on both sides of the QCS, wherein the ES is a fixed sequence that is a same sequence among a subset of forward primers of a same QCS type.

17. The oligonucleotide composition of claim 16, wherein the QCS is positioned within 4-6 nucleotides of the TS.

18. The oligonucleotide composition of claim 16, wherein one or more primers comprises an adaptor sequence (AS) on a 5'-end of the QCS.

19. The oligonucleotide composition of claim 18, wherein, for a portion of the forward primers, the ES is between the AS and the QCS (AES) or in between the QCS and the TS (TES).

20. The oligonucleotide composition of claim 18, wherein the forward primers of the plurality of primer pairs all have a universal AS, and wherein the QCS is not part of or complementary to the universal AS.

21. The oligonucleotide composition of claim 16, wherein the forward primer QCS and the reverse primer QCS of each primer pair are of a same QCS type such that the forward primer and the reverse primer have a same level of randomness.

22. The oligonucleotide composition of claim 16, wherein the ES comprises a sequence of between 2 and 5 bases.

23. The oligonucleotide composition of claim 16, wherein QCS1, QCS2, QCS3, QCS4, QCS5, QCS6, QCS7, or QCS8 comprises a sequence of 3-12 bases.

* * * * *

SEQUENCE LISTING

<160> NUMBER OF SEQ ID NOS: 468

<210> SEQ ID NO 1
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ccctgggctc tgtaaagaa                                              19

<210> SEQ ID NO 2
<211> LENGTH: 24
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 2
atcagagctt aaactgggaa gctg                                         24

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
acagtaactg ccttcataga tag                                          23

<210> SEQ ID NO 4
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
gtgtcagacc ctgttctaag ta                                           22

<210> SEQ ID NO 5
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
tgattttcct ctttggtatc cttatgtaat                                   30

<210> SEQ ID NO 6
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
acaacatttg tatctttatc tgtatcct                                     28

<210> SEQ ID NO 7
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
tttgtatttc atgtgtacat tcgtatc                                      27
```

```
<210> SEQ ID NO 8
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
acctatcctg tagattattt tcactgtg                                           28

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
ctctgagtga caaattgaga cctt                                               24

<210> SEQ ID NO 10
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
ttaacttctc tggtgtgtgg agatg                                              25

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
tttggtgcac ccattacccg                                                    20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
aggaggttga ggctgcaaaa                                                    20

<210> SEQ ID NO 13
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 13
caccaaatat tggtaattaa atgtttacta tagac					35

<210> SEQ ID NO 14
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
taaagggtat gatagaacac ttgtc					25

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
caaaggcaga tcccaagctc t					21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
tgtgtgtgca tctgtaagca t					21

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
tggtgtgtat tccctgtgcc					20

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gcagtccaat ctgggtgaca					20

<210> SEQ ID NO 19
<211> LENGTH: 28
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 19
ccaatctggt cacaaacata ttaatgaa                                           28

<210> SEQ ID NO 20
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
tttcccttgt cttgttatta aaggaac                                            27

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ttcccattgg cctgttcctc                                                    20

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ctgtacacag ggcttccgag                                                    20

<210> SEQ ID NO 23
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
gctgagtgat ttgtctgtaa ttg                                                23

<210> SEQ ID NO 24
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gaactcacag attaaactgt aaccaaaata aaattag                                 37
```

<210> SEQ ID NO 25
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
caatagtgtg caaggatggg tg                                              22

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
tctgtggttc tccagcttac                                                 20

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
cttagggaac cctcactgaa tg                                              22

<210> SEQ ID NO 28
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
gtccttgtca gcgtttattt gc                                              22

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ttgggttgag ccataggcag                                                 20

<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
gcatccgtga ctctctggac                                               20

<210> SEQ ID NO 31
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gttatgggac ttttctcagt ctccat                                        26

<210> SEQ ID NO 32
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gagactaata ggaggtagat agactgg                                       27

<210> SEQ ID NO 33
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gagactgtat tagtaaggct tctc                                          24

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
cctggactga gccatgctcc                                               20

<210> SEQ ID NO 35
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
cagtcctgtg ttagtcagga ttc                                           23

<210> SEQ ID NO 36
<211> LENGTH: 22
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
tcaagggtca actgtgtgat gt                                          22

<210> SEQ ID NO 37
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
cttctgaaag cttctagttt acct                                        24

<210> SEQ ID NO 38
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
ttgcttattt gtgggggtat ttca                                        24

<210> SEQ ID NO 39
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
aagaattctc ttatttgggt tattaattg                                   29

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
aaattgtgga caggtgcggt                                             20

<210> SEQ ID NO 41
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
ccatgtaaaa atacatgcat gtgtttattt atac                             34
```

<210> SEQ ID NO 42
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
tgattaaaaa gaatgaaggt aaaaatgtgt ataac                                35

<210> SEQ ID NO 43
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
ccaaatgttt atgattaatc ttttaaattg gagc                                 34

<210> SEQ ID NO 44
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
gtaacaaggg ctacaggaat catgag                                          26

<210> SEQ ID NO 45
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
tcatccactg aaatgactga aaaatag                                         27

<210> SEQ ID NO 46
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
aggtacataa cagttcaata gaaag                                           25

<210> SEQ ID NO 47
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 47
gagttattca gtaagttaaa ggattgcag                                29

<210> SEQ ID NO 48
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
gggagccagt ggatttggaa acag                                    24

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
gcatggtgag gctgaagtag                                         20

<210> SEQ ID NO 50
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
ctaacctatg gtcataacga ttttt                                   25

<210> SEQ ID NO 51
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
gatgataaga ataatcagta tgtgacttgg                              30

<210> SEQ ID NO 52
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
ataggttaga tagagatagg acagatgata                              30

<210> SEQ ID NO 53
<211> LENGTH: 22

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
ccctaccgct atagtaactt gc                                          22

<210> SEQ ID NO 54
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
cacgtctgta attccagctc cta                                         23

<210> SEQ ID NO 55
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ggaagcgtgt actagagttc ttcag                                       25

<210> SEQ ID NO 56
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ggacagcctc catatccaca tg                                          22

<210> SEQ ID NO 57
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
ttcctactgc cccaccttta ttg                                         23

<210> SEQ ID NO 58
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
```

```
tttatggtct cagtgcccct caga                                              24
```

<210> SEQ ID NO 59
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59

```
tcataatcac atatcacatg agc                                               23
```

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60

```
aaacagaacc agggggaatga a                                                21
```

<210> SEQ ID NO 61
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61

```
tgaaactaaa gtcaaatggg gctac                                             25
```

<210> SEQ ID NO 62
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62

```
taagggggtga cacctctctg gata                                             24
```

<210> SEQ ID NO 63
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63

```
cccagcctac atctaccact tcatg                                             25
```

<210> SEQ ID NO 64
<211> LENGTH: 28
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 64
ctaatgttcg tatggacctt tggaaagc                                         28

<210> SEQ ID NO 65
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
gtctccagta cccagctagc ttag                                             24

<210> SEQ ID NO 66
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
tctcccaacc tgccctttat ca                                               22

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
tttgggctga cacagtggct                                                  20

<210> SEQ ID NO 68
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
ttgatcaaca caggaggttt gacc                                             24

<210> SEQ ID NO 69
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
tataccactt tgatgttgac actagtttac                                       30

<210> SEQ ID NO 70
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
cctgtctatg gtctcgattc aat                                           23

<210> SEQ ID NO 71
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
tgcatgacag agggagattc t                                             21

<210> SEQ ID NO 72
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72 agagggaaa tagtagaatg aggatg                                         26

<210> SEQ ID NO 73
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
gccaaactct attagtcaac gttc                                          24

<210> SEQ ID NO 74
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
ctggttctct agctcacata cagt                                          24

<210> SEQ ID NO 75
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
```

```
tttacccta acaagaaaaa aagaagaa                                              28
```

<210> SEQ ID NO 76
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76

```
cagtgtgaga agtgtgagaa gtgc                                                 24
```

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77

```
gacaccatgc caaacaacaa c                                                    21
```

<210> SEQ ID NO 78
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78

```
atctatctat tccaattaca tagtcc                                               26
```

<210> SEQ ID NO 79
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79

```
tcattatacc tacttctgta tccaactctc                                           30
```

<210> SEQ ID NO 80
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80

```
ggaacacaat tatccctgag tagcag                                               26
```

<210> SEQ ID NO 81
<211> LENGTH: 29
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 81
ggtagcataa tagaaatttt atgagtgggg                                      29

<210> SEQ ID NO 82
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
gaagacagac ttcaatatca cagaacatcg                                      30

<210> SEQ ID NO 83
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
gtgtatctat tcattcaatc atacaccc                                        28

<210> SEQ ID NO 84
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
ctccctggtt gcaagcaatt gcc                                             23

<210> SEQ ID NO 85
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
ccaaaattag tggggaatag ttgaac                                          26

<210> SEQ ID NO 86
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
gtcgagatca caccattgca tttc                                            24
```

```
<210> SEQ ID NO 87
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
gcctggcttg gaattctttt accc                                          24

<210> SEQ ID NO 88
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
tttaagtctt taatctatct tgaattaata gattc                              35

<210> SEQ ID NO 89
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
ctttaagagg agtctgctaa aaggaatg                                      28

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
tcaccagaag gttgcaagac                                               20

<210> SEQ ID NO 91
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
tctggcgaag taacccaaac                                               20

<210> SEQ ID NO 92
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 92
tcgagtcagt tcaccagaag g                                          21

<210> SEQ ID NO 93
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
ggaaccagtg agagccg                                               17

<210> SEQ ID NO 94
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
ctcagagtgc tgaacccag                                             19

<210> SEQ ID NO 95
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
gtatttattc atgatcagtt cttaactcaa cc                              32

<210> SEQ ID NO 96
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
ctacctaata tttatctata tcattctaat tatgtctctt c                    41

<210> SEQ ID NO 97
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
ctctaaaggt ttttttggt ggcataag                                    28

<210> SEQ ID NO 98
<211> LENGTH: 32
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic primer"

<400> SEQUENCE: 98
gattaataca acaaaaattt ggtaatctga aa                                    32

<210> SEQ ID NO 99
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
caacctaagc tgaaatgcag atattc                                          26

<210> SEQ ID NO 100
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
gttatgaaac gtaaatgaa tgatgactag                                       30

<210> SEQ ID NO 101
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
gcagtctcat ttcctggaga tgaagg                                          26

<210> SEQ ID NO 102
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
cttgggctga ggagttcaat c                                               21

<210> SEQ ID NO 103
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
gccagtaaga ataaaattac agcatgaag                                       29
```

<210> SEQ ID NO 104
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
gaataatcta ccagcaacaa tggct                                         25

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
tgcccaatgg aatgctctct                                               20

<210> SEQ ID NO 106
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
gctccatctc aaacaacaaa aacacaaaaa atg                                33

<210> SEQ ID NO 107
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
gggtcattga acctcatgct ctg                                           23

<210> SEQ ID NO 108
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108 cccccaaaa ttctactgaa gtaaa                                          25

<210> SEQ ID NO 109
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
taacaggata aatcacctat ctatgtat                                              28

<210> SEQ ID NO 110
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
gctgaggaga atttccaaat tta                                                   23

<210> SEQ ID NO 111
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
cccgcaaact aactaggata aatctcta                                              28

<210> SEQ ID NO 112
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
cgacatggga aatgtcagat cataagac                                              28

<210> SEQ ID NO 113
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
ccagggagtg aaaaatcctt ttatcatc                                              28

<210> SEQ ID NO 114
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
gaggatgaag gttagagcca gacct                                                 25

<210> SEQ ID NO 115
<211> LENGTH: 28
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
tgtggaataa actgaaggct aaagaaaa                                              28

<210> SEQ ID NO 116
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
caagccctat gccaaggata taacaatg                                              28

<210> SEQ ID NO 117
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
gaggttttac tgtattagga gttcccac                                              28

<210> SEQ ID NO 118
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
cagatgtgag atgataattt cgttctcc                                              28

<210> SEQ ID NO 119
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
ttgttcttct ccatcccatt tcaccc                                                26

<210> SEQ ID NO 120
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
cttgtacatt cccttatctg ctatgtgg                                              28
```

<210> SEQ ID NO 121
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
ctctctttgg agttttatgt gttgctac                                    28

<210> SEQ ID NO 122
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
ctctgatgat gtgcaagaaa ggtaggta                                    28

<210> SEQ ID NO 123
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
tcagactatg ttttaaggag actatgagg                                   29

<210> SEQ ID NO 124
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
ctaagtatct accaatgtgc tacgtacc                                    28

<210> SEQ ID NO 125
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
cacgtggatg atatggtttc tcaagg                                      26

<210> SEQ ID NO 126
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 126
agcacctata tattatacct gaaagcat                                              28

<210> SEQ ID NO 127
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
cccatgattt tcttgtggtg agaatttc                                              28

<210> SEQ ID NO 128
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 128
caccctctgt actttaattt gacttccc                                              28

<210> SEQ ID NO 129
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
gtttttcttc attcccatgt tgtgtac                                               27

<210> SEQ ID NO 130
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130
cactcttctg aatcctggtc aacaac                                                26

<210> SEQ ID NO 131
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 131
caagttatat catagagtct acgacccc                                              28

<210> SEQ ID NO 132
<211> LENGTH: 28

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
ctgcaactat cagtctctgc ccttattc                                       28

<210> SEQ ID NO 133
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133
gatgtgtctc aaactgttta ttgtgagg                                       28

<210> SEQ ID NO 134
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134
gaactcattt atccagagac ctgttctc                                       28

<210> SEQ ID NO 135
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
cataatacaa cctgtctttg gagttact                                       28

<210> SEQ ID NO 136
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
gtgaccagta gttctatgag caagtatg                                       28

<210> SEQ ID NO 137
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 137
```
ccacattgta tggtttttag gcaccatg                                          28

<210> SEQ ID NO 138
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
ctaataagtg ggacagttaa gagaaggc                                          28

<210> SEQ ID NO 139
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 139
caagacaagc gattgaaaga agtggat                                           27

<210> SEQ ID NO 140
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
ccttgtcaat ctttctacca gagggtaa                                          28

<210> SEQ ID NO 141
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 141
gaatcatagc ttgtgttggt caggg                                             25

<210> SEQ ID NO 142
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
gaattacaag tatttgcatc ccagcct                                           27

<210> SEQ ID NO 143
<211> LENGTH: 28
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 143
gaccaacttg gctttaacag atgcaaat                                              28

<210> SEQ ID NO 144
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
tccttacctt taagactttt cctatttg                                              28

<210> SEQ ID NO 145
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
cattatctcg tcatacttcc ctgtcttg                                              28

<210> SEQ ID NO 146
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
gcatcaaatt caccagtgaa attattga                                              28

<210> SEQ ID NO 147
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
atgagtacat tattcaactg ttttggag                                              28

<210> SEQ ID NO 148
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
cagccatgtt gtaaacattt ttacggtc                                              28

<210> SEQ ID NO 149
```

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 149
gcacattcta agaactggtg attctatc                                          28

<210> SEQ ID NO 150
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 150
gctagaaaaa gctgagatag ctgtgaag                                          28

<210> SEQ ID NO 151
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 151
ccttgaagct cattctttgt tgtccc                                            26

<210> SEQ ID NO 152
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 152
ctggacacca gaccaaaaac aaataacc                                          28

<210> SEQ ID NO 153
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 153
gtaattagag ggcagtgagg cttttaa                                           27

<210> SEQ ID NO 154
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 154
```

```
ctccagaagc tactgggata ttaattag                                              28
```

<210> SEQ ID NO 155
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155

```
tgagccaaat cagcaatata ataggact                                              28
```

<210> SEQ ID NO 156
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 156

```
cctagaacca caattatctg tctttggc                                              28
```

<210> SEQ ID NO 157
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157

```
ccattgattc tctacagttc tgcaggta                                              28
```

<210> SEQ ID NO 158
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 158

```
ctccacactt tatacaggtg aaatctga                                              28
```

<210> SEQ ID NO 159
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 159

```
cattttctc tccttctgtc tcaccttc                                               28
```

<210> SEQ ID NO 160
<211> LENGTH: 28
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 160
gcttctcttt cccttatgta tctctctc                                              28

<210> SEQ ID NO 161
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 161
ggcttttgaa gaaaaacact aacctgtc                                              28

<210> SEQ ID NO 162
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 162
cacctatggg ctcttcttat ttctcc                                                26

<210> SEQ ID NO 163
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 163
catttgatag ccatttgggt tgtttcca                                              28

<210> SEQ ID NO 164
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 164
ccatcacact atcctgacat gaacaaat                                              28

<210> SEQ ID NO 165
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 165
gaagatttgc atcccagtga aagcac                                                26
```

```
<210> SEQ ID NO 166
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 166
gcacttcata aagaatcagt caggatgc                                            28

<210> SEQ ID NO 167
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 167
ggagaatcag gaaatagtca cttcctac                                            28

<210> SEQ ID NO 168
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 168
catttgacct tctagccaaa tgaagtac                                            28

<210> SEQ ID NO 169
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 169
ggaatttctg agaataacat tgcctctc                                            28

<210> SEQ ID NO 170
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 170
catatgttgg gggagctaaa cctaatga                                            28

<210> SEQ ID NO 171
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 171
cactgtgacc acagcatctt ttaactc                                27

<210> SEQ ID NO 172
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
gggtaaagaa atattcagca catccaaa                               28

<210> SEQ ID NO 173
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 173
gagtatccct tatctaaaat gctggtcc                               28

<210> SEQ ID NO 174
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 174 cttttctct taccggaact tcaacgac                                28

<210> SEQ ID NO 175
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
cctcattaat atgaccaagg ctcctctg                               28

<210> SEQ ID NO 176
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
tgactctaat tggggatgtg gtaattag                               28

<210> SEQ ID NO 177
<211> LENGTH: 25
<212> TYPE: DNA
<213> ORGANISM: Artificial Sequence -continued

```
<220> FEATURE:
<221> NAME/KEY: source
<223> OTHER INFORMATION: /note="Description of Artificial Sequence:
      Synthetic primer"

<400> SEQUENCE: 177
gacctaacct ggagaaaacc ggaga                                           25

<210> SEQ ID NO 178
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 178
gtttctcttc tctgaacctt tgtctcag                                        28

<210> SEQ ID NO 179
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179
gcaaacacac aaagataggt tcgagttt                                        28

<210> SEQ ID NO 180
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180
catatcaagt gctttctgtt gacatttg                                        28

<210> SEQ ID NO 181
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 181
ctgaaaagtg ctacgtaaga ggtcattg                                        28

<210> SEQ ID NO 182
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 182
catctgagtg tgagaagagc ctcaa                                           25
```

<210> SEQ ID NO 183
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 183
cccagcaaaa acttcttttc tccagtaa                                         28

<210> SEQ ID NO 184
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 184
gctaggaaag ttttctctct ggttcaca                                         28

<210> SEQ ID NO 185
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 185
gaatatctat gagcaggcag ttagcag                                          27

<210> SEQ ID NO 186
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 186
ctaatcagtg tcactatgtg tgagctat                                         28

<210> SEQ ID NO 187
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 187
catcatacag actcaaggag cttagctg                                         28

<210> SEQ ID NO 188
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 188
ctttccaagc cttggaaaac acagaaaa                                              28

<210> SEQ ID NO 189
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
gtaccttata aatcacggag tgcagac                                               27

<210> SEQ ID NO 190
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 190
caagtggtaa gagatgactg aggtcaa                                               27

<210> SEQ ID NO 191
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 191
cttcttctct tagaaggaca ctggtcag                                              28

<210> SEQ ID NO 192
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 192
gttatggagg attggtaaga accagag                                               27

<210> SEQ ID NO 193
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 193
gagctgttta agggtaaagg ggtagtta                                              28

<210> SEQ ID NO 194
<211> LENGTH: 28
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 194
gcagacaaaa ccatgacaat gatcttag                                          28

<210> SEQ ID NO 195
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 195
cccatgatga aacagtttgc actaaatg                                          28

<210> SEQ ID NO 196
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 196
ctcaattttc ttgtccctgc tttcatg                                           27

<210> SEQ ID NO 197
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 197
ttagaaattc cagatagagc taaaactg                                          28

<210> SEQ ID NO 198
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 198
gttaggaaaa gaacccaggt gtttt                                             25

<210> SEQ ID NO 199
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 199
gcaaaagtaa atacaaaggc atacttt                                           27
```

```
<210> SEQ ID NO 200
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 200
caatgcaaaa gaaaggtcct tactcgac                                        28

<210> SEQ ID NO 201
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 201
catttctaaa ctctaaaaca aacatttg                                        28

<210> SEQ ID NO 202
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 202
ggtccttaac ctattaaatt ttaatgag                                        28

<210> SEQ ID NO 203
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 203
gactttcaat ttatgtcagc atttaaaa                                        28

<210> SEQ ID NO 204
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 204
cctcttggtt gcattggatt ctcattg                                         27

<210> SEQ ID NO 205
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"

<400> SEQUENCE: 205
tctccatgaa acttgggtta attttgc                                27

<210> SEQ ID NO 206
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206
tgtctggaag ttcgtcaaat tgcag                                  25

<210> SEQ ID NO 207
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207
gtagcataaa acattccaaa aattcaat                               28

<210> SEQ ID NO 208
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
tgctttaaag atacaggtta tctgtattac                             30

<210> SEQ ID NO 209
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 209
ctctccgtta ctttcttcct gcctttt                                26

<210> SEQ ID NO 210
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 210
gatcctgaga ttcacctcta gtccct                                 26

<210> SEQ ID NO 211
<211> LENGTH: 26

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 211
ccgtaccagg tacctagcta tgtact                                          26

<210> SEQ ID NO 212
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 212
ctttctgttt tgtccatctg aaattct                                         27

<210> SEQ ID NO 213
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 213
caaagttaag tatcaccatc cagctgg                                         27

<210> SEQ ID NO 214
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 214
atagggatag ctgataagaa acatgacc                                        28

<210> SEQ ID NO 215
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 215
cttaataaga cgctgcatct gccca                                           25

<210> SEQ ID NO 216
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 216
```
tccaggagac atttgttcat ataagtga                                              28

<210> SEQ ID NO 217
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 217
agacactttt cagtatccat ttagaaac                                              28

<210> SEQ ID NO 218
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 218
gtttcacatg tgcatgcttt tgggt                                                 25

<210> SEQ ID NO 219
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 219
ccaaagctat tctctctttt gggtgc                                                26

<210> SEQ ID NO 220
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 220
gaaagttcac ttcagatgtt caaagcc                                               27

<210> SEQ ID NO 221
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 221
gggtttcagt ctgcaacaag atcttg                                                26

<210> SEQ ID NO 222
<211> LENGTH: 28
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 222
tggagatcaa tatttagcct taacatat                                            28

<210> SEQ ID NO 223
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 223
gactgtttct catcctgtta ttatttgt                                            28

<210> SEQ ID NO 224
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 224
aacacacaga aacatcaagc tgagc                                               25

<210> SEQ ID NO 225
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225
ttcctgacat tctccttctt ctatctg                                             27

<210> SEQ ID NO 226
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 226
tatgacgcct ggattttcac aacaac                                              26

<210> SEQ ID NO 227
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
cagagactat ggatggtatt taggtcaa                                            28

<210> SEQ ID NO 228
```

```
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228
actttgtgtg gctgagagag agaaa                                           25

<210> SEQ ID NO 229
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229
tgagtgttct ctgtattttc ttactctaag                                      30

<210> SEQ ID NO 230
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230 attttggtc attgttgaca cttcacc                                          27

<210> SEQ ID NO 231
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 231
ggtgttaggg agacaggcat gaatg                                           25

<210> SEQ ID NO 232
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
tgaaactttt caactctcct accgcc                                          26

<210> SEQ ID NO 233
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 233
```
gttaaaattg ccactaatta tgtgtttt                                        28

<210> SEQ ID NO 234
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 234
aactgatcct atgcagcaag atctttg                                         27

<210> SEQ ID NO 235
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 235
gatgcttgca aacaaagact gaaaagg                                         27

<210> SEQ ID NO 236
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 236
gtctgtgtgt cctctgagat gatgaatg                                        28

<210> SEQ ID NO 237
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 237
gggaggaaga aaacagagag tcttga                                          26

<210> SEQ ID NO 238
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 238
agtttgttgg cttcttttga gaagtatc                                        28

<210> SEQ ID NO 239
<211> LENGTH: 28
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 239
ggcagatgaa gtagtagata tctggctg                                            28

<210> SEQ ID NO 240
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 240
gttcagtgtc aattttgacc agatatt                                             27

<210> SEQ ID NO 241
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 241
agacatagga cacaccattt tattgtct                                            28

<210> SEQ ID NO 242
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
tcaaaatatt tggctaaact attgccgg                                            28

<210> SEQ ID NO 243
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 243
ctggagttat taataaattg gattatatag c                                        31

<210> SEQ ID NO 244
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
ttacctgttt tccttttgtg attccac                                             27
```

```
<210> SEQ ID NO 245
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
accaagtcaa gagctctgag agacat                                        26

<210> SEQ ID NO 246
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 246
acagtgaatg atattcagaa tattgtgc                                      28

<210> SEQ ID NO 247
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 247
gaacaaggtc aagatatcag ctttcacc                                      28

<210> SEQ ID NO 248
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 248
aggtcataca atgaatggtg tgatgt                                        26

<210> SEQ ID NO 249
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 249
atccacccat gagaaatata tccacaa                                       27

<210> SEQ ID NO 250
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 250
acaattcaaa ttaatgtaaa aactgcaagt g                                31

<210> SEQ ID NO 251
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 251
tagttctagt gtgggatctg actcc                                       25

<210> SEQ ID NO 252
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 252
gaacatctgt tcaggtttct ctccatc                                     27

<210> SEQ ID NO 253
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 253
gaaaggacta aattgttgaa cactggt                                     27

<210> SEQ ID NO 254
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 254
tgtgtgtttt aaagccaggt ttgtt                                       25

<210> SEQ ID NO 255
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 255
gatggactgg aactgaggat tttca                                       25

<210> SEQ ID NO 256
<211> LENGTH: 29
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 256
agctttagaa aggcatatcg tattaactg                                    29

<210> SEQ ID NO 257
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 257
ttatagtgag taaaggacag gcccc                                        25

<210> SEQ ID NO 258
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 258
acacatctgt tgacagtaat gaaatatcc                                    29

<210> SEQ ID NO 259
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 259
gtttaaactt ggataccatc cccaagac                                     28

<210> SEQ ID NO 260
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 260
atgagattgc tgggagatgc agatg                                        25

<210> SEQ ID NO 261
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 261
cacatttccc tcttgcggtt acatac                                       26
```

<210> SEQ ID NO 262
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 262
gacaagcctc gcttgagttt tcttt                                          25

<210> SEQ ID NO 263
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 263
tgtgagagtg tcaccgaatt caacg                                          25

<210> SEQ ID NO 264
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 264
aaatagcaat ggctcgtcta tggttag                                        27

<210> SEQ ID NO 265
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 265
tgctaagtaa ggtgagtggt ataatca                                        27

<210> SEQ ID NO 266
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 266
ataaatatga tgtggctact ccctcat                                        27

<210> SEQ ID NO 267
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

-continued

<400> SEQUENCE: 267
gctacacctc catagtaata atgtaagag                                        29

<210> SEQ ID NO 268
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 268
tgaagcagct agagaactct gtacgt                                           26

<210> SEQ ID NO 269
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 269
ttttgtctct gttatattag tcacctatct c                                     31

<210> SEQ ID NO 270
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 270
atagccctgc attcaaatcc caagtg                                           26

<210> SEQ ID NO 271
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 271 tccatttta taccactgca ctgaag                                            26

<210> SEQ ID NO 272
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 272
gcagtaaaac attttcatca aatttcca                                         28

<210> SEQ ID NO 273
<211> LENGTH: 27
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 273
tctgggtgca aactagctga atatcag                                              27

<210> SEQ ID NO 274
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 274
gaaaatctgg aggcaattca tgatgcc                                              27

<210> SEQ ID NO 275
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 275
atacaatgat gatcacacgg gaccct                                               26

<210> SEQ ID NO 276
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 276
ccatgaagat ggagtcaaca ttttaca                                              27

<210> SEQ ID NO 277
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 277
tcctaacccc tagtacgtta gatgtg                                               26

<210> SEQ ID NO 278
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 278
gaggtgattt ctgtgaggaa cgtcg                                                25
```

<210> SEQ ID NO 279
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 279
gtacattcac ttaacaggct ctctttcc                          28

<210> SEQ ID NO 280
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 280
aattcatgag ctggtgtcca aggag                             25

<210> SEQ ID NO 281
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 281
ataacagtct ccagagtata ttagcttag                         29

<210> SEQ ID NO 282
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 282
gttcctctgg gatgcaacat gagag                             25

<210> SEQ ID NO 283
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 283
gaaaggatga agagggtgga tattggag                          28

<210> SEQ ID NO 284
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

-continued

Synthetic primer"

<400> SEQUENCE: 284
ccaaacctca tcatctctta cctggatt                                          28

<210> SEQ ID NO 285
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 285
gtccaaagtc aagtgcaagt atagttgg                                          28

<210> SEQ ID NO 286
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 286
acaatctttt ctgaatctga acagcttc                                          28

<210> SEQ ID NO 287
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 287
caaaggaagg catttcctaa tgatcttc                                          28

<210> SEQ ID NO 288
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 288
ctttgctttg cttttcttct tcagggaa                                          28

<210> SEQ ID NO 289
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 289
ctgcttcaag tgtatataaa ctcacagt                                          28

<210> SEQ ID NO 290
<211> LENGTH: 28

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 290
cctaggaaag cagtaactaa ttcaggag                                        28

<210> SEQ ID NO 291
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 291
gcaatttgtt cacttttagt ttcgtagc                                        28

<210> SEQ ID NO 292
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 292
ggcctaatat gcatgtgttc atgtctct                                        28

<210> SEQ ID NO 293
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 293
cagagtttct catctacgaa agaggagt                                        28

<210> SEQ ID NO 294
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 294
atcctagacc tccaggtgga atgatc                                          26

<210> SEQ ID NO 295
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 295
```

```
cttggctgtc tcaatatttt ggagtaag                                      28
```

```
<210> SEQ ID NO 296
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 296
gagtaaatga gctgtggttt ctctctta                                      28
```

```
<210> SEQ ID NO 297
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 297
ctttccatgt ggacccttta acattcag                                      28
```

```
<210> SEQ ID NO 298
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 298
gcatagtgag ctgttgatag agcttttg                                      28
```

```
<210> SEQ ID NO 299
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 299
ctagaacaaa atcattggct ctcctagt                                      28
```

```
<210> SEQ ID NO 300
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 300
gtctggtgag tactggctga atgtaaa                                       27
```

```
<210> SEQ ID NO 301
<211> LENGTH: 28
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic primer"

<400> SEQUENCE: 301
ccagaggatg ctgctaaaca ttctacaa                                    28

<210> SEQ ID NO 302
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 302
gctcatgcct ggaattcacc tttatttt                                    28

<210> SEQ ID NO 303
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 303
ctaactagac atttgggcca ccttactt                                    28

<210> SEQ ID NO 304
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 304
gtctatggtg cctatagaat gtacaggt                                    28

<210> SEQ ID NO 305
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 305
ccctctcaag tttgtgagca aatatcac                                    28

<210> SEQ ID NO 306
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 306
ctctatcttg ctgcaatgga ctttcc                                      26

<210> SEQ ID NO 307

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 307
cctagaaaca gattttgaag ggctcttg                                        28

<210> SEQ ID NO 308
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 308
aaatgagggg catagggata aggga                                           25

<210> SEQ ID NO 309
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 309
cctagaaatc tgatacgtta tcctatga                                        28

<210> SEQ ID NO 310
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 310
aggagagata tattcaacat gaacccaa                                        28

<210> SEQ ID NO 311
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 311
gaacatctct gaccagaaat ttccagta                                        28

<210> SEQ ID NO 312
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 312
```

```
gtgtagtgaa atccttagac ttaggtaa                                          28
```

<210> SEQ ID NO 313
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 313

```
aatacatgaa aaagtaatac atggggca                                          28
```

<210> SEQ ID NO 314
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 314

```
attaaatgtt tacttctatc tacaagga                                          28
```

<210> SEQ ID NO 315
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 315

```
cattttgtga aatgcaaagg gcaaatct                                          28
```

<210> SEQ ID NO 316
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 316

```
gctgagaggc ttaattccat caagatga                                          28
```

<210> SEQ ID NO 317
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 317

```
cccatcctaa acttagtttt atgggcag                                          28
```

<210> SEQ ID NO 318
<211> LENGTH: 27
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 318
gtaacacatt ctctttggga agctagc                                        27

<210> SEQ ID NO 319
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 319
cttagcttca gtgaaaatgg ttcctctc                                       28

<210> SEQ ID NO 320
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 320
ctttcttagc tcctctccat ttctcttc                                       28

<210> SEQ ID NO 321
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 321
gtctatgcag tgcttcactg aggattat                                       28

<210> SEQ ID NO 322
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 322
ctctatctgc tcagagcctg cttaaaag                                       28

<210> SEQ ID NO 323
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 323
ggaaaggata cagtgttgag caagatag                                       28

```
<210> SEQ ID NO 324
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 324
gccaacttga ttctctttca aatgcttg                                          28

<210> SEQ ID NO 325
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 325
agatggggtt taccatgttt cccag                                             25

<210> SEQ ID NO 326
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 326
gtacagtagt tagtttccag actgatga                                          28

<210> SEQ ID NO 327
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 327
gtaaatatct aactgtgttt ccctcagt                                          28

<210> SEQ ID NO 328
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 328
gaaccaaaag gaattaagag actagggg                                          28

<210> SEQ ID NO 329
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 329
ctgcttttac ggcttcttcc tttcttc                                27

<210> SEQ ID NO 330
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 330
cccacatcct tcccatttat aggcaa                                 26

<210> SEQ ID NO 331
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 331
tacatgatcc taagggcagc aggaa                                  25

<210> SEQ ID NO 332
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 332
gtttggtgca tcctctttct ctctc                                  25

<210> SEQ ID NO 333
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 333
gactgtagtc accccttctc caaca                                  25

<210> SEQ ID NO 334
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 334
agagtgaaat acatagaaaa gaaacttaaa g                           31

<210> SEQ ID NO 335
<211> LENGTH: 28
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 335
atttgcgaga aacagataaa tattgaag                                       28

<210> SEQ ID NO 336
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 336
acaggaacaa agaatttgtt cttcatgg                                       28

<210> SEQ ID NO 337
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 337
ccttggattg tctcaggatg ttgca                                          25

<210> SEQ ID NO 338
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 338
ctgggatgtt tgttttggct ttgtg                                          25

<210> SEQ ID NO 339
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 339
attggtagta cactaatgga tatatgtgag                                     30

<210> SEQ ID NO 340
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 340
gaataaagtg aggaaaacac ggagttg                                        27
```

```
<210> SEQ ID NO 341
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 341
gagagaggca gaaaggaggg atgaa                                         25

<210> SEQ ID NO 342
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 342
tactctgtct tcagtagctg tttcttgg                                      28

<210> SEQ ID NO 343
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 343
ttagactcac caagatcaag atgaatgc                                      28

<210> SEQ ID NO 344
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 344
atctcaataa agctgttcaa aacagaaag                                     29

<210> SEQ ID NO 345
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 345
taaagaaaat gccatgggct gtaccc                                        26

<210> SEQ ID NO 346
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 346
attgtgcagc agaacagagt gtagtg                                               26

<210> SEQ ID NO 347
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 347
attctttgca tagctcacga aatttccc                                             28

<210> SEQ ID NO 348
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 348
aaaatgagac ctcgtatctt tgcagc                                               26

<210> SEQ ID NO 349
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 349
aaatgcagaa ctgccaaaag aaaccc                                               26

<210> SEQ ID NO 350
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 350
gagaatctgt gaatgccagg gtctg                                                25

<210> SEQ ID NO 351
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 351
atggattcat gtttcagaca tctaatt                                              27

<210> SEQ ID NO 352
<211> LENGTH: 28
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 352
atcactagaa agaaaagagt tcctattc                                           28

<210> SEQ ID NO 353
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 353
gaagtttaaa agagtgggaa catgggg                                            27

<210> SEQ ID NO 354
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 354
ctacgtaagc aaaaatgatc acgcac                                             26

<210> SEQ ID NO 355
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 355
aacctgatgg ccctcattag tcctt                                              25

<210> SEQ ID NO 356
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 356
caccagattt ctaggaatag catgtgag                                           28

<210> SEQ ID NO 357
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 357
aagagcatag tgaggggtta gacct                                              25
```

```
<210> SEQ ID NO 358
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 358
ctttatattt agtgtagaga tcagtctcc                                         29

<210> SEQ ID NO 359
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 359 tgagtcctttt acctaatctt ggttgtc                                          27

<210> SEQ ID NO 360
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 360
aatccaaagc aactctcttt tcaccac                                           27

<210> SEQ ID NO 361
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 361
tttactggaa ccctgatttt gttgga                                            26

<210> SEQ ID NO 362
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 362
tgccactgat atatcagtac ctgagt                                            26

<210> SEQ ID NO 363
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 363
acaatctcaa tccccttaa tgttttc                                    27

<210> SEQ ID NO 364
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 364
gtgggcagag agagtaagag aacct                                     25

<210> SEQ ID NO 365
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 365
caaaccagat tctggcagaa tagttagc                                  28

<210> SEQ ID NO 366
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 366
cttctctccc atcctccttc tccac                                     25

<210> SEQ ID NO 367
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 367
agatcaaggg atctgtggga caataac                                   27

<210> SEQ ID NO 368
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 368
ggggagtgat ttcaagcatc ctgatt                                    26

<210> SEQ ID NO 369
<211> LENGTH: 27

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 369
catgagtttg aggtaagatg aaggaga                                             27

<210> SEQ ID NO 370
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 370
tctctctcat cctagtgaat gccatc                                              26

<210> SEQ ID NO 371
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 371
gggtgatgat ctaccttgca ggtata                                              26

<210> SEQ ID NO 372
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 372
ctcaaggccc tgggtctgaa attac                                               25

<210> SEQ ID NO 373
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 373
acatctccag ttaataattt ccactaac                                            28

<210> SEQ ID NO 374
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 374
```
tggattgctc aacaaatagt gctaaaa 27

<210> SEQ ID NO 375
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 375
catgcgacat ccaggtagct aaaatac 27

<210> SEQ ID NO 376
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 376
atggataaaa atggaacttt caagagaa 28

<210> SEQ ID NO 377
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 377
gttttatgta aagcttcgtc atatggct 28

<210> SEQ ID NO 378
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 378
gttccaactt agtcataaag ttccctgg 28

<210> SEQ ID NO 379
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 379
gggtcttgat gttgtattga tgaggaag 28

<210> SEQ ID NO 380
<211> LENGTH: 28
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 380
cctaacagaa agtcactgtt tgtatctg                                              28

<210> SEQ ID NO 381
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 381
tcactctggc ttgtactctc tctgtg                                                26

<210> SEQ ID NO 382
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 382
ggctggtttc agtctggaga ctttattt                                              28

<210> SEQ ID NO 383
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 383
cttcacctcg atgacgatga tgatgat                                               27

<210> SEQ ID NO 384
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 384
gacaataaca gcacaaagga tggaaaag                                              28

<210> SEQ ID NO 385
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 385
gaaccagacc acacaatatc accac                                                 25

<210> SEQ ID NO 386
```

```
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 386
tctacctctt tgatgtcccc ttcgatag                                       28

<210> SEQ ID NO 387
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 387
cagagtttct catctacgaa agaggagt                                       28

<210> SEQ ID NO 388
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 388
cccagctttg aaaagtatgc ctagaact                                       28

<210> SEQ ID NO 389
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 389
ctgcttcaag tgtatataaa ctcacagt                                       28

<210> SEQ ID NO 390
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 390
ttgtttcatc cactttggtg ggtaaaag                                       28

<210> SEQ ID NO 391
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 391
```
taattaagct ctgtgtttag ggttttt        27

<210> SEQ ID NO 392
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 392
caattctttg ttctttaggt cagtatat        28

<210> SEQ ID NO 393
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 393
tactcttcct cagtcccttc tctgc        25

<210> SEQ ID NO 394
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 394
tgagacagag catgatgatc atggc        25

<210> SEQ ID NO 395
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 395
gcacaagtct aggaactact ttgcac        26

<210> SEQ ID NO 396
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 396
gaagtatttg aaccatacgg agccc        25

<210> SEQ ID NO 397
<211> LENGTH: 26
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic primer"

<400> SEQUENCE: 397
tgaggaacac atccaaacta tgacac                                        26

<210> SEQ ID NO 398
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 398
tttctcgccc tcatcatctg caatg                                         25

<210> SEQ ID NO 399
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 399
tcagttgatt tcatgtgatc ctcacag                                       27

<210> SEQ ID NO 400
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 400
gaataaagtg aggaaaacac ggagttg                                       27

<210> SEQ ID NO 401
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 401
attaccttct ttctaataca agcatatg                                      28

<210> SEQ ID NO 402
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 402
acaggaacaa agaatttgtt cttcatgg                                      28

<210> SEQ ID NO 403
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 403
tacacgacgc tcttccgatc tnnnnncaaa gaagtcaaaa cagagggatc a          51

<210> SEQ ID NO 404
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 404
tacacgacgc tcttccgatc tnnnnncaaa ggcagatccc aagctct              47

<210> SEQ ID NO 405
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 405
tacacgacgc tcttccgatc tnnnnncaat agtgtgcaag gatgggtg             48

<210> SEQ ID NO 406
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 406
tacacgacgc tcttccgatc tnnnnncaac ctaagctgaa atgcagatat tc         52

<210> SEQ ID NO 407
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:

```
    Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 407
cttggcaccc gagaattcca nnnnnaggag gttgaggctg caaaa            45

<210> SEQ ID NO 408
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 408
tacacgacgc tcttccgatc tnnnnngcat ggtgaggctg aagtag           46

<210> SEQ ID NO 409
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 409
tacacgacgc tcttccgatc tnnnnngcar ctagaatata agcaggcagg a     51

<210> SEQ ID NO 410
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 410
tacacgacgc tcttccgatc tnnnnngcag tctcatttcc tggagatgaa gg    52

<210> SEQ ID NO 411
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 411
```
tacacgacgc tcttccgatc tnnnnnccct gggctctgta aagaa         45

<210> SEQ ID NO 412
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 412
cttggcaccc gagaattcca nnnnnggaac acaattatcc ctgagtagca g         51

<210> SEQ ID NO 413
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 413
cttggcaccc gagaattcca nnnnnggaca gcctccataw ccacatg         47

<210> SEQ ID NO 414
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 414
cttggcaccc gagaattcca nnnnngcatc crtgactctc tggac         45

<210> SEQ ID NO 415
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 415
tacacgacgc tcttccgatc tnnnnntgaa actaaagtca aatggggcta c         51

<210> SEQ ID NO 416
<211> LENGTH: 59
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 416
tacacgacgc tcttccgatc ttacgbnnnd cgcacaaaga agtcaaaaca gagggatca      59

<210> SEQ ID NO 417
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 417
tacacgacgc tcttccgatc ttacgbnnnd cgctcaaagg cagatcccaa gctct          55

<210> SEQ ID NO 418
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 418
tacacgacgc tcttccgatc ttacgbnnnd cgctcaatag tgtgcaagga tgggtg         56

<210> SEQ ID NO 419
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 419
tacacgacgc tcttccgatc ttacgbnnnd cgctcaacct aagctgaaat gcagatattc     60

<210> SEQ ID NO 420
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
```

<222> LOCATION: (24)..(27)
<223> OTHER INFORMATION: a, c, t, g, unknown or other

<400> SEQUENCE: 420
cttggcaccc gagaattcca acgnnnnhcc ggaggaggtt gaggctgcaa aa            52

<210> SEQ ID NO 421
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 421
tacacgacgc tcttccgatc ttacgbnnnd cgctgcatgg tgaggctgaa gtag          54

<210> SEQ ID NO 422
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 422
tacacgacgc tcttccgatc ttacgbnnnd cgctgcarct agaatataag caggcagga     59

<210> SEQ ID NO 423
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 423
tacacgacgc tcttccgatc ttacgbnnnd cgctgcagtc tcatttcctg gagatgaagg    60

<210> SEQ ID NO 424
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 424
tacacgacgc tcttccgatc ttacgbnnnd cgctccctgg gctctgtaaa gaa           53

<210> SEQ ID NO 425
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (24)..(27)
<223> OTHER INFORMATION: a, c, t, g, unknown or other

<400> SEQUENCE: 425
cttggcaccc gagaattcca acgnnnnhcc gcggaacaca attatccctg agtagcag    58

<210> SEQ ID NO 426
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (24)..(27)
<223> OTHER INFORMATION: a, c, t, g, unknown or other

<400> SEQUENCE: 426
cttggcaccc gagaattcca acgnnnnhcc gcggacagcc tccatawcca catg    54

<210> SEQ ID NO 427
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (24)..(27)
<223> OTHER INFORMATION: a, c, t, g, unknown or other

<400> SEQUENCE: 427
cttggcaccc gagaattcca acgnnnnhcc gcgcatccrt gactctctgg ac    52

<210> SEQ ID NO 428
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (27)..(29)
<223> OTHER INFORMATION: a, c, t, g, unknown or other

<400> SEQUENCE: 428
tacacgacgc tcttccgatc ttacgbnnnd cgcctgaaac taaagtcaaa tggggctac    59

<210> SEQ ID NO 429
<211> LENGTH: 24
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 429
aatagagatc gcgagacaga aagg                                          24

<210> SEQ ID NO 430
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(5)
<223> OTHER INFORMATION: a, c, t, g, unknown or other

<400> SEQUENCE: 430
nnnnntttat ggtctcagtg cccctcaga                                     29

<210> SEQ ID NO 431
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 431
tgtgtggcag aagttgaaaa tta                                           23

<210> SEQ ID NO 432
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(5)
<223> OTHER INFORMATION: a, c, t, g, unknown or other

<400> SEQUENCE: 432
nnnnntttat ggtctcagtg cccctcaga                                     29

<210> SEQ ID NO 433
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 433
ataaatcaga ccaggatgaa agttc                                         25

<210> SEQ ID NO 434
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic primer"
<220> FEATURE:
<221> NAME/KEY: modified_base
<222> LOCATION: (1)..(5)
<223> OTHER INFORMATION: a, c, t, g, unknown or other

<400> SEQUENCE: 434
nnnnntttat ggtctcagtg ccccctcaga                                              29

<210> SEQ ID NO 435
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 435
aataatcctc aaaaacaaag aaacatgg                                                28

<210> SEQ ID NO 436
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(5)
<223> OTHER INFORMATION: a, c, t, g, unknown or other

<400> SEQUENCE: 436
nnnnntttat ggtctcagtg ccccctcaga                                              29

<210> SEQ ID NO 437
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 437
tctggcgaag taacccaaac                                                         20

<210> SEQ ID NO 438
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(5)
<223> OTHER INFORMATION: a, c, t, g, unknown or other

<400> SEQUENCE: 438
nnnnntttat ggtctcagtg ccccctcaga                                              29

<210> SEQ ID NO 439
<211> LENGTH: 25
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 439
aaaacatgaa gataacaaat cccaa                                          25

<210> SEQ ID NO 440
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (1)..(5)
<223> OTHER INFORMATION: a, c, t, g, unknown or other

<400> SEQUENCE: 440
nnnnntttat ggtctcagtg cccctcaga                                      29

<210> SEQ ID NO 441
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 441
tacacgacgc tcttccgatc tnnnnn                                         26

<210> SEQ ID NO 442
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 442
cttggcaccc gagaattcca nnnnntttat ggtctcagtg cccctcaga                49

<210> SEQ ID NO 443
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (25)..(29)
<223> OTHER INFORMATION: a, c, t, g, unknown or other

<400> SEQUENCE: 443
```
tacacgacgc tcttccgatc tacgnnnnn                                    29

<210> SEQ ID NO 444
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 444
cttggcaccc gagaattcca nnnnntttat ggtctcagtg cccctcaga              49

<210> SEQ ID NO 445
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (25)..(29)
<223> OTHER INFORMATION: a, c, t, g, unknown or other

<400> SEQUENCE: 445
tacacgacgc tcttccgatc tacgnnnnnc gcg                               33

<210> SEQ ID NO 446
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (24)..(28)
<223> OTHER INFORMATION: a, c, t, g, unknown or other

<400> SEQUENCE: 446
cttggcaccc gagaattcca acgnnnnncg cgaaattgtg gmcaggtgcg gt          52

<210> SEQ ID NO 447
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (25)..(28)
<223> OTHER INFORMATION: a, c, t, g, unknown or other

<400> SEQUENCE: 447
tacacgacgc tcttccgatc tacgnnnndc gcg                               33

<210> SEQ ID NO 448
<211> LENGTH: 52
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (24)..(28)
<223> OTHER INFORMATION: a, c, t, g, unknown or other

<400> SEQUENCE: 448
cttggcaccc gagaattcca acgnnnnncg cgaaattgtg gmcaggtgcg gt          52

<210> SEQ ID NO 449
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 449
tacacgacgc tcttccgatc tnnnnngcar ctagaatata agcaggcagg a           51

<210> SEQ ID NO 450
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (21)..(25)
<223> OTHER INFORMATION: a, c, t, g, unknown or other

<400> SEQUENCE: 450
cttggcaccc gagaattcca nnnnntttat ggtctcagtg cccctcaga              49

<210> SEQ ID NO 451
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
actctttccc tacacgacgc tcttccgatc t                                 31

<210> SEQ ID NO 452
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(25)
<223> OTHER INFORMATION: a, c, t, g, unknown or other

<400> SEQUENCE: 452
```

```
cttggcaccc gagaattcca nnnnntttat ggtctcagtg cccctcagat cggaagagcg    60
tcgtgta                                                              67
```

<210> SEQ ID NO 453
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (53)..(57)
<223> OTHER INFORMATION: a, c, t, g, unknown or other

<400> SEQUENCE: 453

```
actctttccc tacacgacgc tcttccgatc tgaggggcac tgagaccata aannnnntgg    60
aattctcggg tgccaag                                                   77
```

<210> SEQ ID NO 454
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454

```
actggagttc cttggcaccc gagaattcca                                     30
```

<210> SEQ ID NO 455
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (53)..(57)
<223> OTHER INFORMATION: a, c, t, g, unknown or other

<400> SEQUENCE: 455

```
actctttccc tacacgacgc tcttccgatc tgaggggcac tgagaccata aannnnntgg    60
aattctcggg tgccaaggaa ctccagt                                        87
```

<210> SEQ ID NO 456
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (31)..(35)
<223> OTHER INFORMATION: a, c, t, g, unknown or other

<400> SEQUENCE: 456

```
actggagttc cttggcaccc gagaattcca nnnnntttat ggtctcagtg cccctcagat    60
cggaagagcg tcgtgtaggg aaagagt                                        87
```

```
<210> SEQ ID NO 457
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 457
tacacgacgc tcttccgatc tnnnnngcar ctagaatata agcaggcagg a            51

<210> SEQ ID NO 458
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 458
cttggcaccc gagaattcca tttatggtct cagtgcccct caga                   44

<210> SEQ ID NO 459
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 459
tacacgacgc tcttccgatc thbhhhgcar ctagaatata agcaggcagg a            51

<210> SEQ ID NO 460
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 460
cttggcaccc gagaattcca tttatggtct cagtgcccct caga                   44

<210> SEQ ID NO 461
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (25)..(29)
<223> OTHER INFORMATION: a, c, t, g, unknown or other

<400> SEQUENCE: 461
tacacgacgc tcttccgatc tacannnnna gcggcarcta gaatataagc aggagga     58

<210> SEQ ID NO 462
```

```
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 462
cttggcaccc gagaattcca tttatggtct cagtgcccct caga            44

<210> SEQ ID NO 463
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (26)..(28)
<223> OTHER INFORMATION: a, c, t, g, unknown or other

<400> SEQUENCE: 463
tacacgacgc tcttccgatc tacahnnnba gcggcarcta gaatataagc aggcagga    58

<210> SEQ ID NO 464
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 464
cttggcaccc gagaattcca tttatggtct cagtgcccct caga            44

<210> SEQ ID NO 465
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (22)..(26)
<223> OTHER INFORMATION: a, c, t, g, unknown or other

<400> SEQUENCE: 465
tacacgacgc tcttccgatc tnnnnnccct gggctctgta aagaa           45

<210> SEQ ID NO 466
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 466
cttggcaccc gagaattcca taaggaactg cccagggtca c               41

<210> SEQ ID NO 467
<211> LENGTH: 52
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (26)..(28)
<223> OTHER INFORMATION: a, c, t, g, unknown or other

<400> SEQUENCE: 467
tacacgacgc tcttccgatc tacgbnnndc gctccctggg ctctgtaaag aa          52

<210> SEQ ID NO 468
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 468
cttggcaccc gagaattcca taaggaactg cccagggtca c                      41
```